US012098381B2

(12) United States Patent
Pederson et al.

(10) Patent No.: US 12,098,381 B2
(45) Date of Patent: Sep. 24, 2024

(54) COMPOSITIONS AND METHODS FOR DIFFERENTIAL CAS9 GENE LABELING AND/OR EDITING

(71) Applicants: University of Massachusetts, Boston, MA (US); University of Central Florida Research Foundation, Inc., Orlando, FL (US)

(72) Inventors: Thoru Pederson, Worcester, MA (US); Scot Andrew Wolfe, Winchester, MA (US); Hanhui Ma, Shrewsbury, MA (US); Metewo Selase Kosi Enuameh, Gaithersburg, MD (US); Nicola Anne Kearns, Somerville, MA (US); Ryan Michael Jude Genga, Framingham, MA (US); Rene Maehr, Newton, MA (US); Shaojie Zhang, Oviedo, FL (US); Ardalan Naseri, Orlando, FL (US); Manuel Garber, Winchester, MA (US)

(73) Assignee: University of Massachusetts, Boston, MA (US)

( * ) Notice: Subject to any disclaimer, the term of this patent is extended or adjusted under 35 U.S.C. 154(b) by 541 days.

(21) Appl. No.: 17/200,398

(22) Filed: Mar. 12, 2021

(65) Prior Publication Data

US 2021/0340566 A1    Nov. 4, 2021

Related U.S. Application Data

(63) Continuation of application No. 14/571,818, filed on Dec. 16, 2014, now abandoned.

(60) Provisional application No. 61/917,003, filed on Dec. 17, 2013.

(51) Int. Cl.
| | | |
|---|---|---|
| *C12N 15/85* | (2006.01) | |
| *C12N 5/0735* | (2010.01) | |
| *C12N 5/074* | (2010.01) | |
| *C12N 9/22* | (2006.01) | |
| *C12N 15/63* | (2006.01) | |
| *C12N 15/86* | (2006.01) | |
| *C12N 15/90* | (2006.01) | |
| *C12Q 1/6841* | (2018.01) | |

(52) U.S. Cl.
CPC ........... *C12N 15/86* (2013.01); *C12N 5/0606* (2013.01); *C12N 5/0696* (2013.01); *C12N 9/22* (2013.01); *C12N 15/63* (2013.01); *C12N 15/907* (2013.01); *C12Q 1/6841* (2013.01); *C12N 2501/65* (2013.01); *C12N 2501/70* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubesnstein et al. | ......... 435/7.9 |
| 3,850,752 A | 11/1974 | Schuurs et al. | ............. 435/7.93 |
| 3,939,350 A | 2/1976 | Kronick et al. | ............. 250/365 |
| 3,996,345 A | 12/1976 | Ullman et al. | ................ 436/537 |
| 4,275,149 A | 6/1981 | Litman et al. | ............... 435/7.91 |
| 4,277,437 A | 7/1981 | Maggio | .......................... 422/401 |
| 4,366,241 A | 12/1982 | Tom et al. | .................... 435/7.91 |
| 2016/0289673 A1* | 10/2016 | Huang | .................. C12N 15/111 |

FOREIGN PATENT DOCUMENTS

| | | |
|---|---|---|
| EP | 1298205 A1 | 4/2003 |
| WO | WO/2005/053512 | 6/2005 |
| WO | WO/2011/057078 | 5/2011 |
| WO | WO/2012/075027 | 6/2012 |

OTHER PUBLICATIONS

Addis, R. C. et al. (2013) "Induced regeneration—the progress and promise of direct reprogramming for heart repair," *Nature Medicine* 19(7), 829-836.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Anton, T. et al. (2014) "Visualization of specific DNA sequences in living mouse embryonic stem cells with a programmable fluorescent CRISPR/Cas system," *Nucleus* 5(2), 163-172.
Benson, G. (1999) "Tandem repeats finder: a program to analyze DNA sequences," *Nucleic Acids Research* 27(2), 573-580.
Bhaya, D. et al. (2011) "CRISPR-Cas Systems in Bacteria and Archaea: Versatile Small RNAs for Adaptive Defense and Regulation," *Annual Review of Genetics* 45(1), 273-297.
Bikard, D et al. (2013) "Programmable repression and activation of bacterial gene expression using an engineered CRISPR-Cas system," *Nucleic Acids Research* 41(15), 7429-7437.
Buganim, Y. et al. (2013) "Mechanisms and models of somatic cell reprogramming," *Nature Reviews Genetics* 14(6), 427-439.
Bultmann, S. et al. (2012) "Targeted transcriptional activation of silent oct4 pluripotency gene by combining designer TALEs and inhibition of epigenetic modifiers," *Nucleic Acids Research* 40(12), 5368-5377.
Cabili, M. N. et al. (2011) "Integrative annotation of human large intergenic noncoding RNAs reveals global properties and specific subclasses," *Genes & Development* 25(18), 1915-1927.
Cattoglio, C. et al. (2007) "Hot spots of retroviral integration in human CD34+ hematopoietic cells," *Blood* 110(6), 1770-1778.

(Continued)

*Primary Examiner* — Celine X Qian
(74) *Attorney, Agent, or Firm* — Medlen & Carroll, LLP

(57) ABSTRACT

The present disclosure relates to methods of and systems for modifying the transcriptional regulation of stem or progenitor cells to promote their differentiation or reprogramming of somatic cells. Further, the labeling and editing of human genomic loci in live cells with three orthogonal CRISPR/Cas9 components allow multicolor detection of genomic loci with high spatial resolution, which provides an avenue for barcoding elements of the human genome in the living state.

9 Claims, 33 Drawing Sheets

Specification includes a Sequence Listing.

(56) References Cited

OTHER PUBLICATIONS

Chambers, I. et al. (2003) "Functional expression cloning of Nanog, a pluripotency sustaining factor in embryonic stem cells," *Cell* 113(5), 643-655.
Charpentier, E. et al. (2013) "Biotechnology: Rewriting a genome," *Nature* 495(7439), 50-51.
Chen, B. et al. (2013) "Dynamic imaging of genomic loci in living human cells by an optimized CRISPR/Cas system," *Cell* 155(7), 1479-1491.
Chen, X. et al. (2010) "Quantitative Organellar Proteomics Analysis of Rough Endoplasmic Reticulum from Normal and Acute Pancreatitis Rat Pancreas," *Journal of Proteome Research* 9(2), 885-896.
Cheng, A. W. et al. (2013) "Multiplexed activation of endogenous genes by CRISPR-on, an RNA-guided transcriptional activator system," *Cell Research* 23(10), 1163-1171.
Cheng, X. et al. (2012) "Self-Renewing Endodermal Progenitor Lines Generated from Human Pluripotent Stem Cells," *Cell Stem Cell* 10(4), 371-384.
Cho, S. W. et al. (2013) "Targeted genome engineering in human cells with the Cas9 RNA-guided endonuclease," *Nature Biotechnology* 31(3), 230-232.
Ciuffi, A. et al. (2006) "Integration Site Selection by HIV-Based Vectors in Dividing and Growth-Arrested IMR-90 Lung Fibroblasts," *Molecular Therapy* 13(2), 366-373.
Cobaleda, C. et al. (2007) "Conversion of mature B cells into T cells by dedifferentiation to uncommitted progenitors," *Nature* 449(7161), 473-477.
Cong, L. et al. (2013) "Multiplex genome engineering using CRISPR/Cas systems," *Science* 339(6121), 819-823.
Cong, L .et al. (2012) "Comprehensive interrogation of natural TALE DNA-binding modules and transcriptional repressor domains," *Nature Communications* 3, 968.
D'Amour, K. A. et al. (2005) "Efficient differentiation of human embryonic stem cells to definitive endoderm," *Nature Biotechnology* 23(12), 1534-1541.
D'Amour, K. A. et al. (2006) "Production of pancreatic hormone-expressing endocrine cells from human embryonic stem cells," *Nature Biotechnology* 24(11), 1392-1401.
Dekker, J. et al. (2013) "Exploring the three-dimensional organization of genomes: interpreting chromatin interaction data," *Nature Reviews Genetics* 14(6), 390-403.
Esvelt, K. M. et al. (2013) "Orthogonal Cas9 proteins for RNA-guided gene regulation and editing," *Nature Methods* 10(11), 1116-1121.
Eymery, A. et al. (2010) "Heat shock factor 1 binds to and transcribes satellite II and III sequences at several pericentromeric regions in heat-shocked cells," *Experimental Cell Research* 316(11), 1845-1855.
Gao, X. et al. (2013) "Reprogramming to Pluripotency Using Designer TALE Transcription Factors Targeting Enhancers," *Stem Cell Reports* 1(2), 183-197.
Gifford, Casey A. et al. (2013) "Transcriptional and epigenetic dynamics during specification of human embryonic stem cells," *Cell* 153(5), 1149-1163.
Gilbert, L. A. et al. (2014) "Genome-Scale CRISPR-Mediated Control of Gene Repression and Activation," *Cell* 159(3), 647-661.
Gilbert, L. A. et al. (2013) "CRISPR-mediated modular RNA-guided regulation of transcription in eukaryotes," *Cell* 154(2), 442-451.
Gouon-Evans, V. et al. (2006) "BMP-4 is required for hepatic specification of mouse embryonic stem cell-derived definitive endoderm," *Nature Biotechnology* 24(11), 1402-1411.
Green, M. D. et al. (2011) "Generation of anterior foregut endoderm from human embryonic and induced pluripotent stem cells," *Nature Biotechnology* 29(3), 267-272.
Haug, U. et al. (2007) "Mutant-Enriched PCR and Allele-Specific Hybridization Reaction to Detect K-ras Mutations in Stool DNA: High Prevalence in a Large Sample of Older Adults," *Clinical Chemistry* 53(4), 787-790.
Hay, D. C. et al. (2004) "Oct-4 Knockdown Induces Similar Patterns of Endoderm and Trophoblast Differentiation Markers in Human and Mouse Embryonic Stem Cells," *Stem Cells* 22(2), 225-235.
Hou, Z. et al. (2013) "Efficient genome engineering in human pluripotent stem cells using Cas9 from Neisseria meningitidis," *Proceedings of the National Academy of Sciences* 110(39), 15644-15649.
Hsu, P. D. et al. (2013) "DNA targeting specificity of RNA-guided Cas9 nucleases," *Nature Biotechnology* 31(9), 827-832.
Hu, G. et al. (2009) "A genome-wide RNAi screen identifies a new transcriptional module required for self-renewal," *Genes & Development* 23(7), 837-848.
Huangfu, D. et al. (2008) "Induction of pluripotent stem cells by defined factors is greatly improved by small-molecule compounds," *Nature Biotechnology* 26(7), 795-797.
Hwang, W. Y. et al. (2013) "Efficient genome editing in zebrafish using a CRISPR-Cas system," *Nature Biotechnology* 31(3), 227-229.
Ivanova, N. et al. (2006) "Dissecting self-renewal in stem cells with RNA interference," *Nature* 442(7102), 533-538.
Jacobson, M. R. et al. (1997) "RNA traffic and localization reported by fluorescence cytochemistry," in *Analysis of mRNA Formation and Function* (Richter, J. D., Ed.), pp. 341-359, Academic, New York.
Jao, L.-E. et al. (2013) "Efficient multiplex biallelic zebrafish genome editing using a CRISPR nuclease system," *Proceedings of the National Academy of Sciences* 110(34), 13904-13909.
Jinek, M. et al. (2012) "A Programmable Dual-RNA-Guided DNA Endonuclease in Adaptive Bacterial Immunity," *Science* 337(6096), 816-821.
Jinek, M. et al. (2013) "RNA-programmed genome editing in human cells," *eLife* 2, e00471.
Kagey, M. H. et al. (2010) "Mediator and cohesin connect gene expression and chromatin architecture," *Nature* 467(7314), 430-435.
Kanai-Azuma, M. et al. (2002) "Depletion of definitive gut endoderm in Sox17-null mutant mice," *Development* 129(10), 2367-2379.
Kearns, N. A. et al. (2014) "Cas9 effector-mediated regulation of transcription and differentiation in human pluripotent stem cells," *Development* 141(1), 219-223.
Kearns, N. A. et al. (2013) "Generation of organized anterior foregut epithelia from pluripotent stem cells using small molecules," *Stem Cell Research* 11(3), 1003-1012.
Kent, W. J. (2002) "BLAT—The BLAST-Like Alignment Tool, " *Genome Research* 12(4), 656-664.
Konermann, S. et al. (2013) "Optical control of mammalian endogenous transcription and epigenetic states," *Nature* 500(7463), 472-476.
Kroon, E. et al. (2008) "Pancreatic endoderm derived from human embryonic stem cells generates glucose-responsive insulin-secreting cells in vivo," *Nature Biotechnology* 26(4), 443-452.
Kubo, A. et al. (2004) "Development of definitive endoderm from embryonic stem cells in culture," *Development* 131(7), 1651-1662.
Ladewig, J. et al. (2013) "Leveling Waddington: the emergence of direct programming and the loss of cell fate hierarchies," *Nature Reviews Molecular Cell Biology* 14(4), 225-236.
Langmead, B. et al. (2012) "Fast gapped-read alignment with Bowtie 2," *Nature Methods* 9(4), 357-359.
Larson, M. H. et al. (2013) "CRISPR interference (CRISPRi) for sequence-specific control of gene expression," *Nature Protocols* 8(11), 2180-2196.
Lee, J. et al. (2006) "The Human OCT-4 Isoforms Differ in Their Ability to Confer Self-renewal," *Journal of Biological Chemistry* 281(44), 33554-33565.
Ma, H. et al. (2013) "Visualization of repetitive DNA sequences in human chromosomes with transcription activator-like effectors," *Proceedings of the National Academy of Sciences* 110(52), 21048-21053.
Maeder, M. L. et al. (2013) "CRISPR RNA-guided activation of endogenous human genes," *Nature Methods* 10(10), 977-979.
Maehr, R. et al. (2009) "Generation of pluripotent stem cells from patients with type 1 diabetes," *Proceedings of the National Academy of Sciences* 106(37), 15768-15773.

(56) References Cited

OTHER PUBLICATIONS

Mali, P. et al. (2013) "CAS9 transcriptional activators for target specificity screening and paired nickases for cooperative genome engineering," *Nature Biotechnology* 31(9), 833-838.
Mali, P. et al. (2013) "RNA-guided human genome engineering via Cas9," *Science* 339(6121), 823-826.
Mann, B. F. et al. (2012) "Glycomic and Proteomic Profiling of Pancreatic Cyst Fluids Identifies Hyperfucosylated Lactosamines on the N-linked Glycans of Overexpressed Glycoproteins," *Molecular & Cellular Proteomics* 11(7), M111.015792-015791-M015111. 015792-015711.
Marraffini, L. A. et al. (2010) "CRISPR interference: RNA-directed adaptive immunity in bacteria and archaea," *Nature Reviews Genetics* 11(3), 181-190.
Moad, M. et al. (2013) "A novel model of urinary tract differentiation, tissue regeneration, and disease: reprogramming human prostate and bladder cells into induced pluripotent stem cells," *European Urology* 64(5), 753-761.
Moffat, J. et al. (2006) "A Lentiviral RNAi Library for Human and Mouse Genes Applied to an Arrayed Viral High-Content Screen," *Cell* 124(6), 1283-1298.
Montini, E. et al. (2006) "Hematopoietic stem cell gene transfer in a tumor-prone mouse model uncovers low genotoxicity of lentiviral vector integration," *Nature Biotechnology* 24(6), 687-696.
Mou, H. et al. (2012) "Generation of multipotent lung and airway progenitors from mouse ESCs and patient-specific cystic fibrosis iPSCs," *Cell Stem Cell* 10(4), 385-397.
Parent, A. V. et al. (2013) "Generation of functional thymic epithelium from human embryonic stem cells that supports host T cell development," *Cell Stem Cell* 13(2), 219-229.
Pederson, T. (2014) "Repeated TALEs," *Nucleus* 5(1), 28-31.
Pennisi, E. (2013) "The CRISPR craze," *Science* 341(6148), 833-836.
Perez-Pinera, P. et al. (2013) "RNA-guided gene activation by CRISPR-Cas9-based transcription factors," *Nature Methods* 10(10), 973-976.
Qi, L. S. et al. (2013) "Repurposing CRISPR as an RNA-guided platform for sequence-specific control of gene expression," *Cell* 152(5), 1173-1183.
Rada-Iglesias, A. et al. (2011) "A unique chromatin signature uncovers early developmental enhancers in humans," *Nature* 470(7333), 279-283.
Ran, F. A. et al. (2013) "Double Nicking by RNA-Guided CRISPR Cas9 for Enhanced Genome Editing Specificity," *Cell* 154(6), 1380-1389.
Ravasi, T. et al. (2010) "An Atlas of Combinatorial Transcriptional Regulation in Mouse and Man," *Cell* 140(5), 744-752.
Rezania, A. et al. (2011) "Production of functional glucagon-secreting a-cells from human embryonic stem cells," *Diabetes* 60(1), 239-247.
Root, D. E. et al. (2006) "Genome-scale loss-of-function screening with a lentiviral RNAi library," *Nature Methods* 3(9), 715-719.
Séguin, C. A. et al. (2008) "Establishment of Endoderm Progenitors by SOX Transcription Factor Expression in Human Embryonic Stem Cells," *Cell Stem Cell* 3(2), 182-195.

Seo, K.-W. et al. (2009) "OCT4A contributes to the stemness and multi-potency of human umbilical cord blood-derived multipotent stem cells (hUCB-MSCs)," *Biochemical and Biophysical Research Communications* 384(1), 120-125.
Sherwood, R. I. et al. (2011) "Wnt signaling specifies and patterns intestinal endoderm," *Mechanisms of Development* 128(7-10), 387-400.
Sims, D. et al. (2011) "High-throughput RNA interference screening using pooled shRNA libraries and next generation sequencing," *Genome Biology* 12(10), R104.
Sorek, R. et al. (2013) "CRISPR-Mediated Adaptive Immune Systems in Bacteria and Archaea," *Annual Review of Biochemistry* 82(1), 237-266.
Sun, X. et al. (2013) "Directed Differentiation of Human Embryonic Stem Cells into Thymic Epithelial Progenitor-like Cells Reconstitutes the Thymic Microenvironment In Vivo," *Cell Stem Cell* 13(2), 230-236.
Takahashi, K. et al. (2006) "Induction of pluripotent stem cells from mouse embryonic and adult fibroblast cultures by defined factors," *Cell* 126(4), 663-676.
Tanenbaum, M. E. et al. (2014) "A Protein-Tagging System for Signal Amplification in Gene Expression and Fluorescence Imaging," *Cell* 159(3), 635-646.
Thomson, J. A. et al. (1998) "Embryonic Stem Cell Lines Derived from Human Blastocysts," *Science* 282(5391), 1145-1147.
Tobi, M. et al. (2013) "Prospective Markers for Early Diagnosis and Prognosis of Sporadic Pancreatic Ductal Adenocarcinoma," *Digestive Diseases and Sciences* 58(3), 744-750.
Trounson, A. et al. (2012) "Human disease modeling with induced pluripotent stem cells," *Current Opinion in Genetics & Development* 22(5), 509-516.
Vierbuchen, T. et al. (2010) "Direct conversion of fibroblasts to functional neurons by defined factors," *Nature* 463(7284), 1035-1041.
Wang, H. et al. (2013) "One-step generation of mice carrying mutations in multiple genes by CRISPR/Cas-mediated genome engineering," *Cell* 153(4), 910-918.
Wiedenheft, B. et al. (2012) "RNA-guided genetic silencing systems in bacteria and archaea," *Nature* 482(7385), 331-338.
Wong, A. P. et al. (2012) "Directed differentiation of human pluripotent stem cells into mature airway epithelia expressing functional CFTR protein," *Nature Biotechnology* 30(9), 876-882.
Yang, H. et al. (2013) "One-step generation of mice carrying reporter and conditional alleles by CRISPR/Cas-mediated genome engineering," *Cell* 154(6), 1370-1379.
Zhang, F. et al. (2011) "Efficient construction of sequence-specific TAL effectors for modulating mammalian transcription," *Nature Biotechnology* 29(2), 149-153.
Zhang, Y. et al. (2013) "Processing-Independent CRISPR RNAs Limit Natural Transformation in Neisseria meningitidis," *Molecular Cell* 50(4), 488-503.
Zhou, Q. et al. (2008) "In vivo reprogramming of adult pancreatic exocrine cells to B-cells," *Nature* 455(7213), 627-632.
PCT International Search Report of International Application No. PCT/US2014/026857 dated Dec. 16, 2014.

* cited by examiner

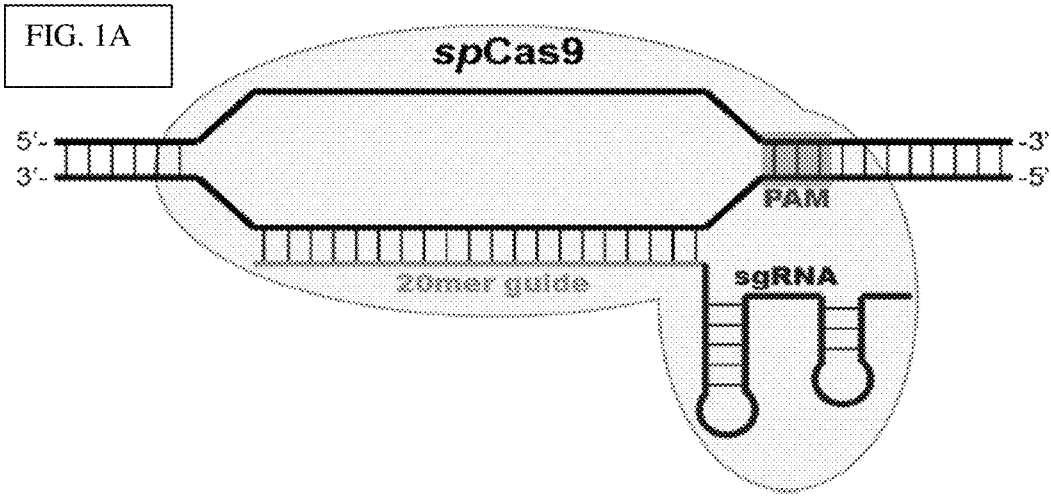
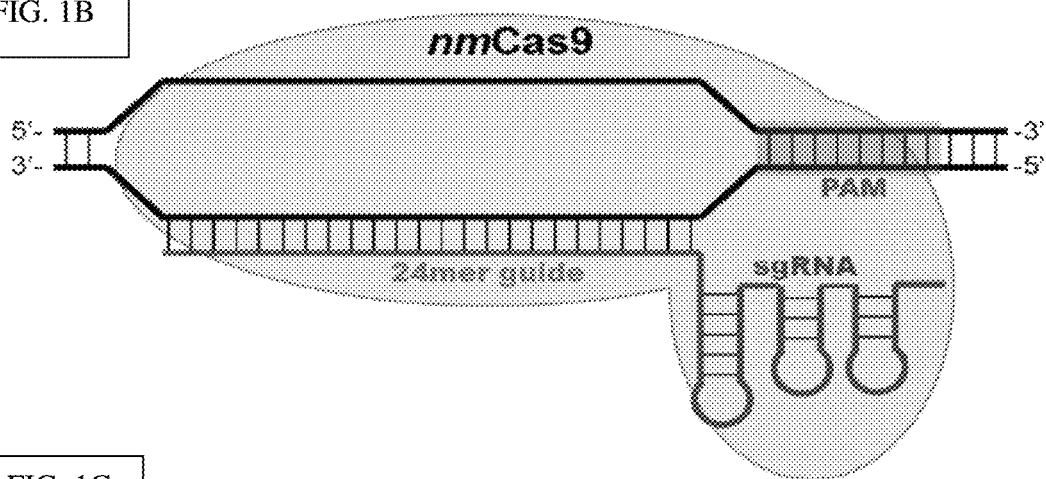
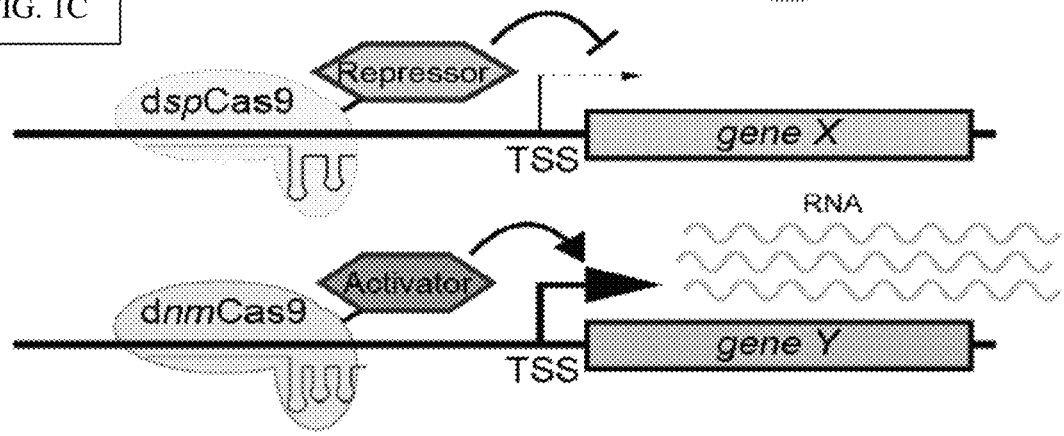

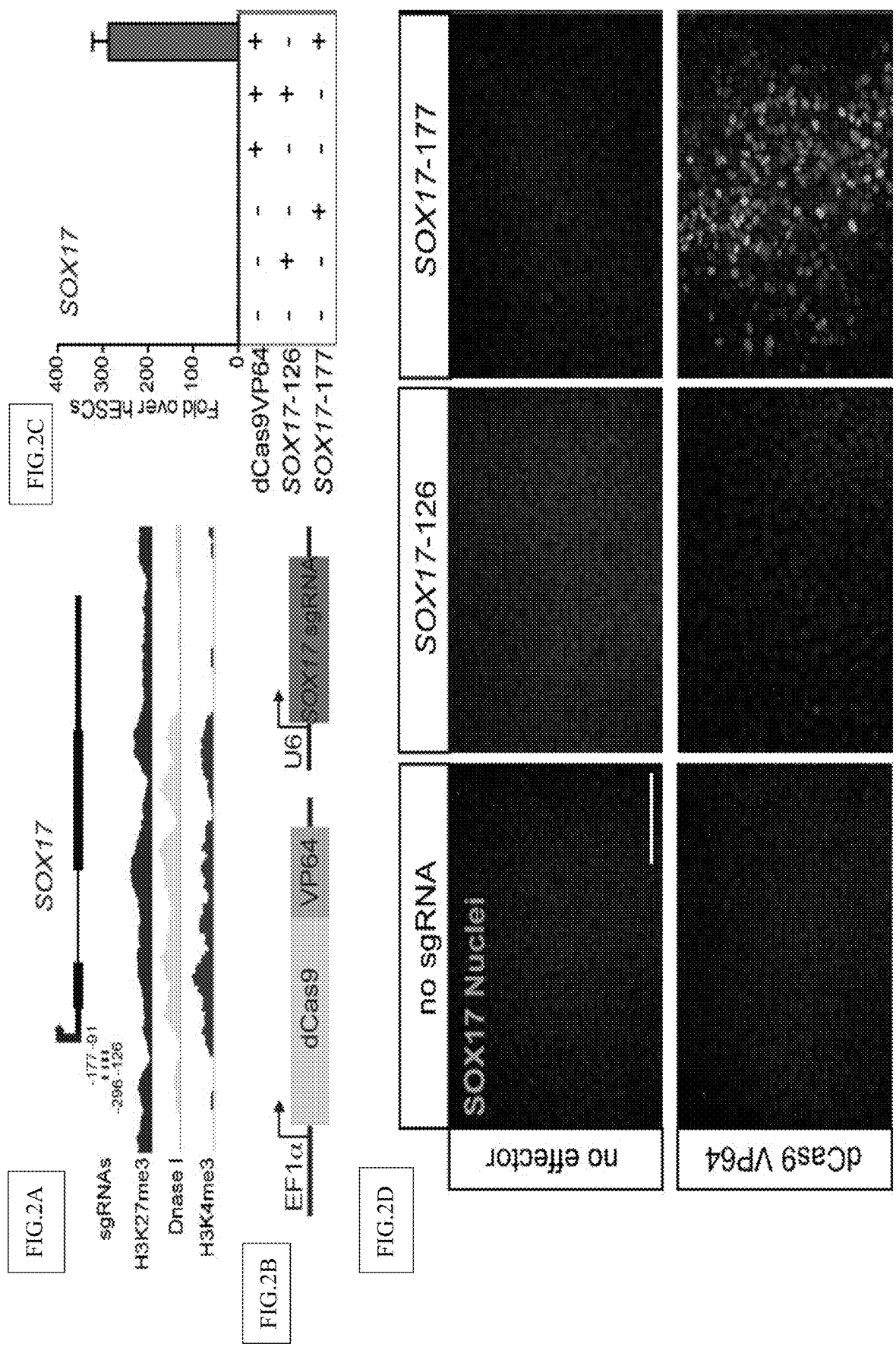

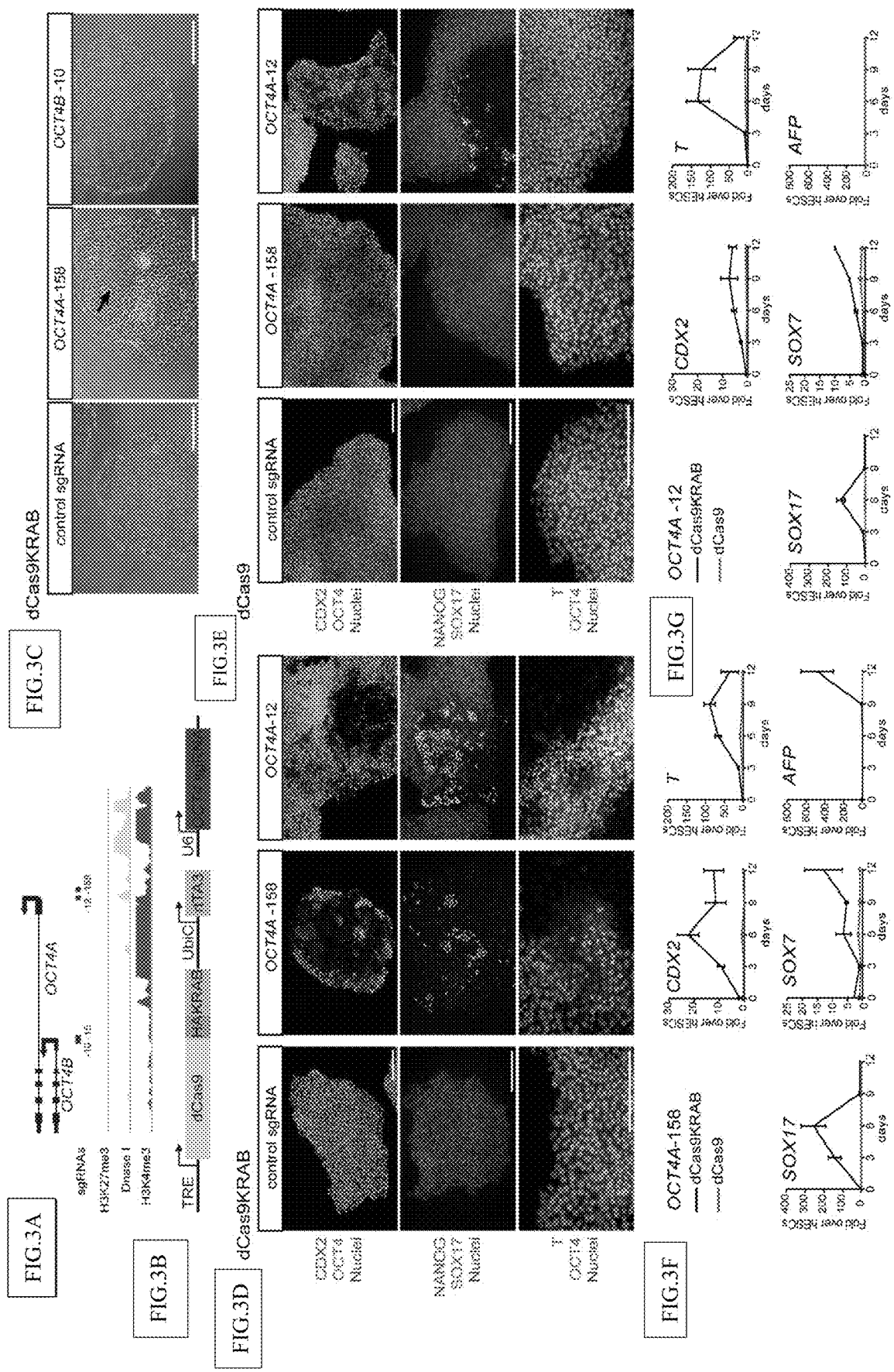

FIGURE 4A dCas9-NLS-3xHA-VP64    (SEQ ID NO: 20)

MDKKYSIGLAIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNI
VDEVAYHEKYPTIYHLRKKLVDSTDKADLRLIYLALAHMIKFRGHFLIEGDLNPDNSDVDK
LFIQLVQTYNQLFEENPINASGVDAKAILSARLSKSRRLENLIAQLPGEKKNGLFGNLIALSL
GLTPNFKSNFDLAEDAKLQLSKDTYDDDLDNLLAQIGDQYADLFLAAKNLSDAILLSDILR
VNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQSF
IERMTNFDKNLPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDK
QSGKTILDFLKSDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRIEEGIKELGSQ
ILKEHPVENTQLQNEKLYLYYLQNGRDMYVDQELDINRLSDYDVDAIVPQSFLKDDSIDN
KVLTRSDKNRGKSDNVPSEEVVKKMKNYWRQLLNAKLITQRKFDNLTKAERGGLSELDK
AGFIKRQLVETRQITKHVAQILDSRMNTKYDENDKLIREVKVITLKSKLVSDFRKDFQFYK
VREINNYHHAHDAYLNAVVGTALIKKYPKLESEFVYGDYKVYDVRKMIAKSEQEIGKATA
KYFFYSNIMNFFKTEITLANGEIRKRPLIETNGETGEIVWDKGRDFATVRKVLSMPQVNIV
KKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTK
EVLDATLIHQSITGLYETRIDLSQLGGDGTGGPKKKRKVYPYDVPDYAGYPYDVPDYAGSY
PYDVPDYAGSGSGRADALDDFDLDMLGSDALDDFDLDMLGSDALDDFDLDMLGSDALD
DFDLDMLIN*

FIGURE 4B dCas9-NLS-3xHA-KRAB  (SEQ ID NO: 21)

MDKKYSIGLAIGTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDKKHERHPIFGNI
VDEVAYHEKYPTIYHLRKKLVDSTDKADLRLIYLALAHMIKFRGHFLIEGDLNPDNSDVDK
LFIQLVQTYNQLFEENPINASGVDAKAILSARLSKSRRLENLIAQLPGEKKNGLFGNLIALSL
GLTPNFKSNFDLAEDAKLQLSKDTYDDDLDNLLAQIGDQYADLFLAAKNLSDAILLSDILR
VNTEITKAPLSASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGELHAILRRQEDFY
PFLKDNREKIEKILTFRIPYYVGPLARGNSRFAWMTRKSEETITPWNFEEVVDKGASAQSF
IERMTNFDKNLPNEKVLPKHSLLYEYFTVYNELTKVKYVTEGMRKPAFLSGEQKKAIVDL
LFKTNRKVTVKQLKEDYFKKIECFDSVEISGVEDRFNASLGTYHDLLKIIKDKDFLDNEEN
EDILEDIVLTLTLFEDREMIEERLKTYAHLFDDKVMKQLKRRRYTGWGRLSRKLINGIRDK
QSGKTILDFLKSDGFANRNFMQLIHDDSLTFKEDIQKAQVSGQGDSLHEHIANLAGSPAIK
KGILQTVKVVDELVKVMGRHKPENIVIEMARENQTTQKGQKNSRERMKRIEEGIKELGSQ
ILKEHPVENTQLQNEKLYLYYLQNGRDMYVDQELDINRLSDYDVDAIVPQSFLKDDSIDN
KVLTRSDKNRGKSDNVPSEEVVKKMKNYWRQLLNAKLITQRKFDNLTKAERGGLSELDK
AGFIKRQLVETRQITKHVAQILDSRMNTKYDENDKLIREVKVITLKSKLVSDFRKDFQFYK
VREINNYHHAHDAYLNAVVGTALIKKYPKLESEFVYGDYKVYDVRKMIAKSEQEIGKATAK
YFFYSNIMNFFKTEITLANGEIRKRPLIETNGETGEIVWDKGRDFATVRKVLSMPQVNIV
KKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASA
GELQKGNELALPSKYVNFLYLASHYEKLKGSPEDNEQKQLFVEQHKHYLDEIIEQISEFSKR
VILADANLDKVLSAYNKHRDKPIREQAENIIHLFTLTNLGAPAAFKYFDTTIDRKRYTSTK
EVLDATLIHQSITGLYETRIDLSQLGGDGGPKKKRKVYPYDVPDYAGYPYDVPDYAGSY
PYDVPDYAGSMDAKSLTAWSRTLVTFKDVFVDFTREEWKLLDTAQQIVYRNVMLENYK
NLVSLGYQLTKPDVILRLEKGEEPWLV* pLKO.1 U6-sgRNA cloning template  (SEQ ID NO: 22)

◊CCGGTGTGCAGGTGAGTGATCAAGAACCTGCTGACG◊TTTAGAGCTAGAAATAGCAAGTTAA
AATA◊GCTAGTCCGTTATCAACTTGAAAAAGTGGCACCGA◊GGTGCTTTTTTTGAATTC

FIG. 5A
FIG. 5B
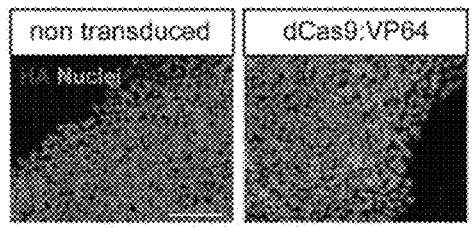
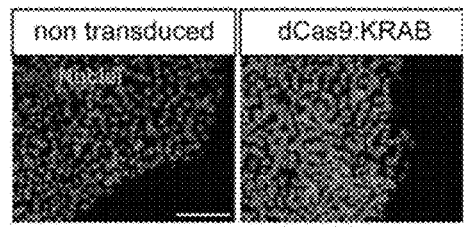
FIG. 5C
FIG. 5D
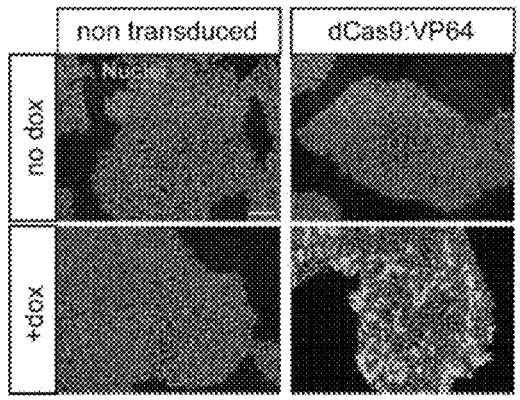
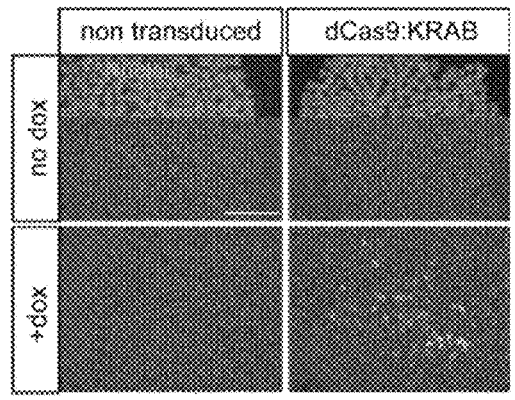

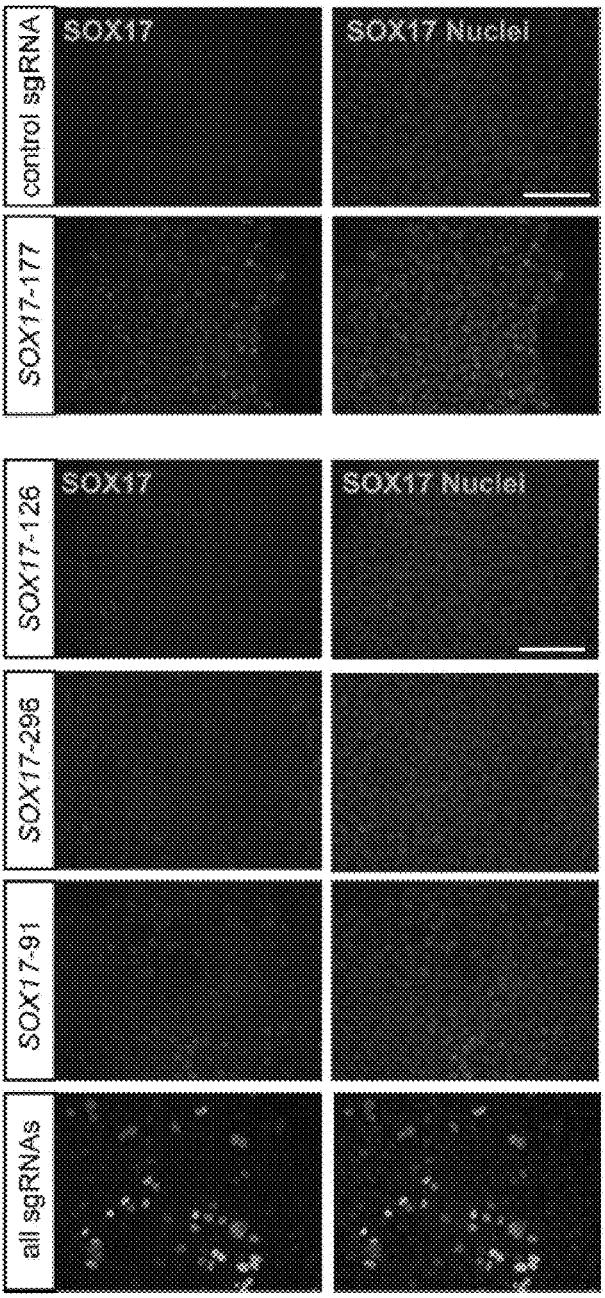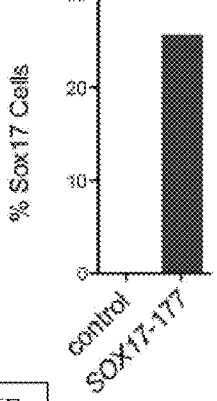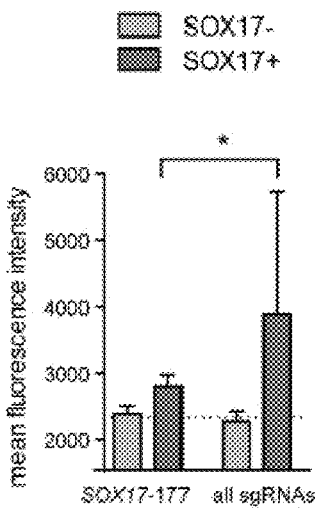

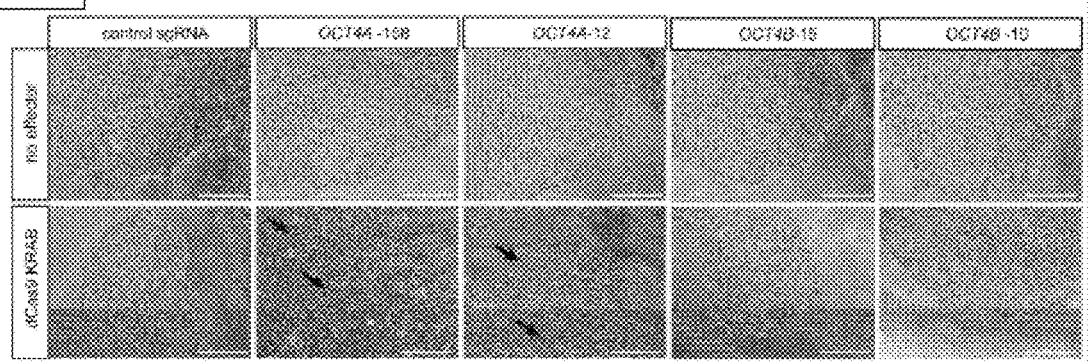
FIG. 7A
FIG. 7B
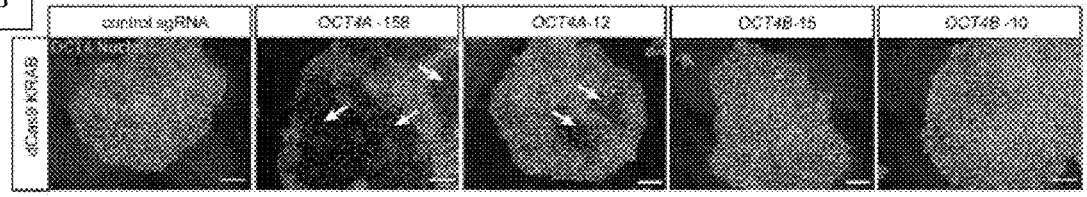
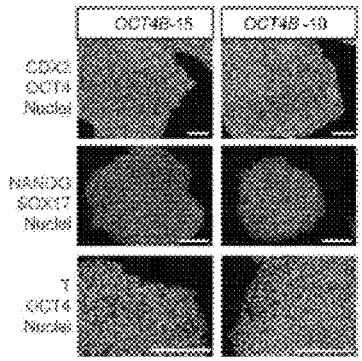
FIG. 7C
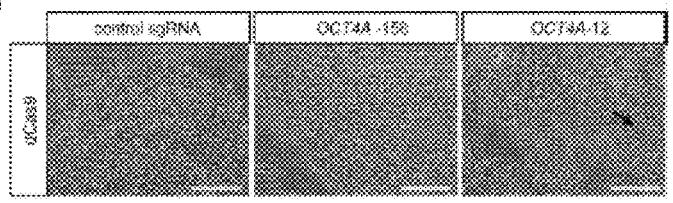
FIG. 7D

FIG. 8A
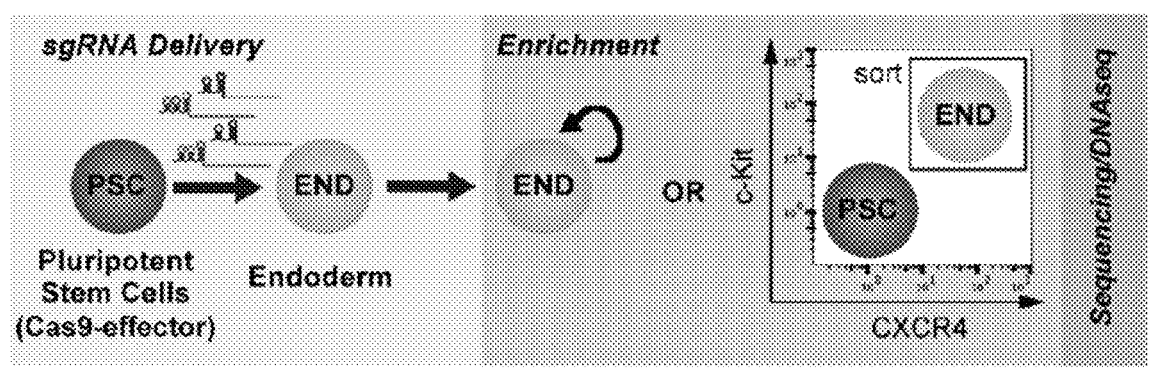
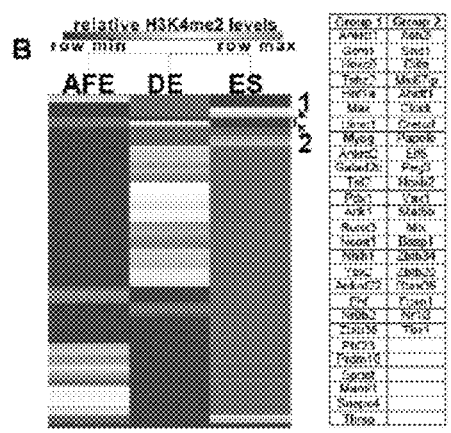
FIG. 8B
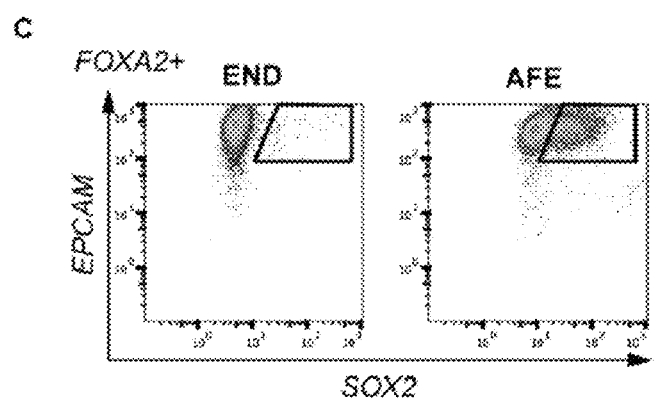
FIG. 8C

SEQ ID NO: 43

FIGURE 11A

| | Sp dCas9-3XCherry | Nm dCas9-3XGFP | |
|---|---|---|---|
| U2OS phase | Sp sgRNA-Telo | Nm sgRNA-Telo | Merge |

FIGURE 11B

| | Sp dCas9-3xGFP | St1 dCas9-3xBFP | |
|---|---|---|---|
| U2OS phase | Sp sgRNA-Telo | St1 sgRNA-Telo | Merge |

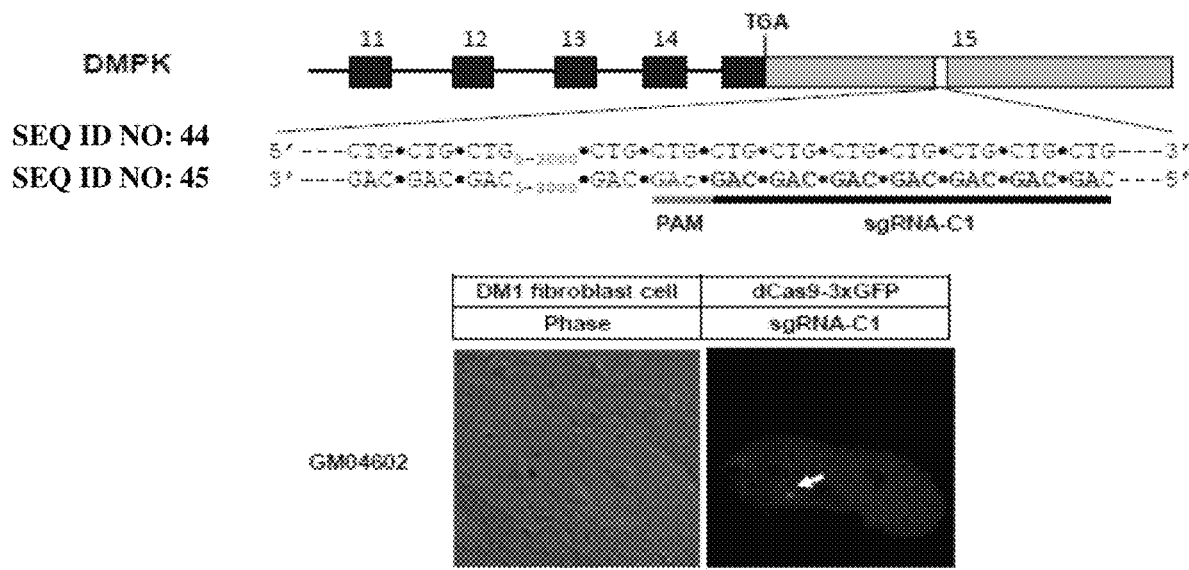
FIGURE 15E
FIGURE 15F
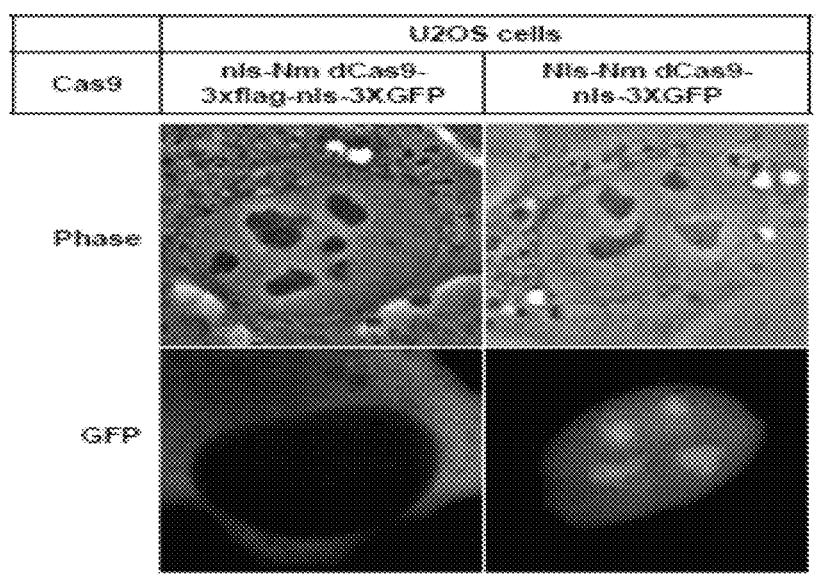

FIGURE 15G
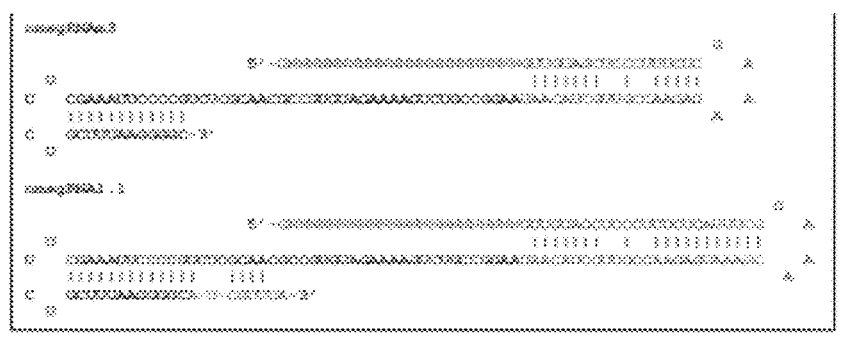
SEQ ID NO: 46
SEQ ID NO: 47
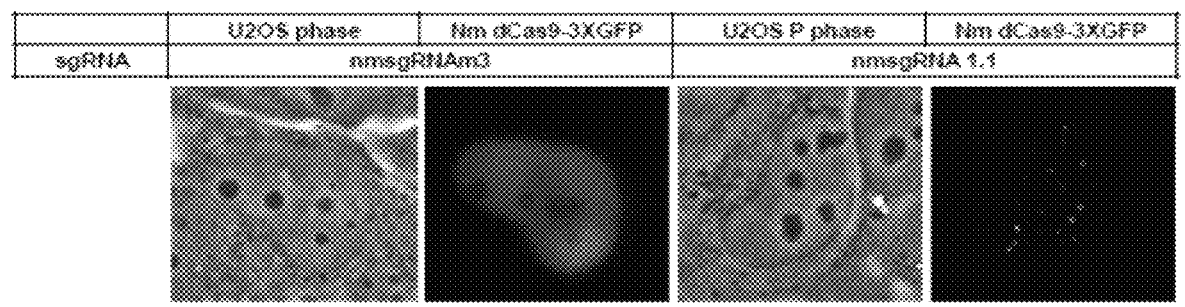
FIGURE 15H
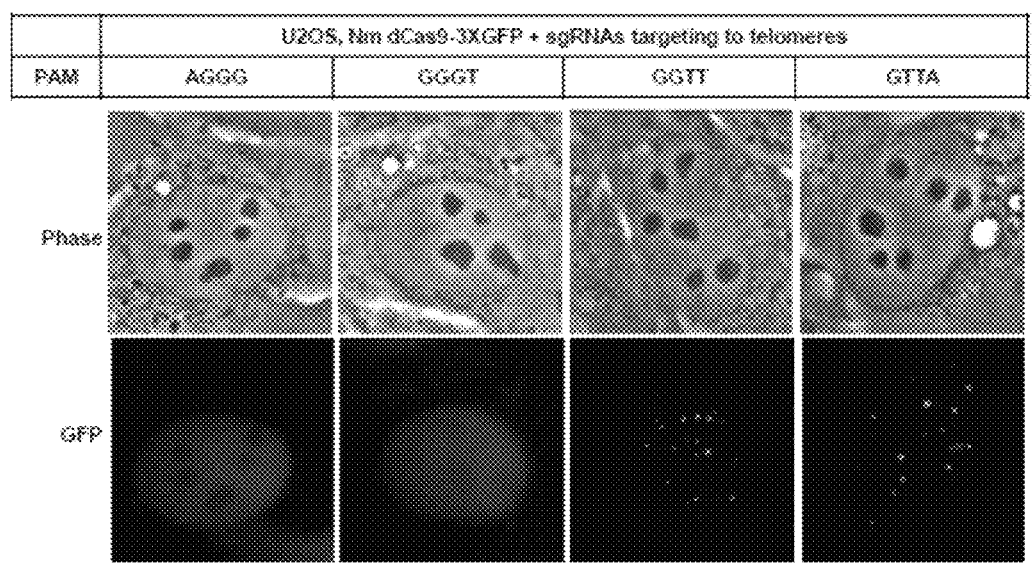

SEQ ID NO: 48

SEQ ID NO: 49

SEQ ID NO: 50

SEQ ID NO: 51

SEQ ID NO: 52

SEQUENCE LISTING

```
<160> NUMBER OF SEQ ID NOS: 69

<210> SEQ ID NO 1
<211> LENGTH: 23
<212> TYPE: DNA
<213> ORGANISM: Artificial sequence
<220> FEATURE:
<223> OTHER INFORMATION: Synthetic

<400> SEQUENCE: 1
ggggcgccag ttgtgtctcc cgg                                              23

<210> SEQ ID NO 2
<211> LENGTH: 23
<212> TYPE: DNA
<213> ORGANISM: Artificial sequence
<220> FEATURE:
<223> OTHER INFORMATION: Synthetic

<400> SEQUENCE: 2
gtgggactgg ggagggagag agg                                              23

<210> SEQ ID NO 3
<211> LENGTH: 23
```

```
<212> TYPE: DNA
<213> ORGANISM: Artificial sequence
<220> FEATURE:
<223> OTHER INFORMATION: Synthetic

<400> SEQUENCE: 3
gggtcccaca aactataaca tgg                                              23

<210> SEQ ID NO 4
<211> LENGTH: 23
<212> TYPE: DNA
<213> ORGANISM: Artificial sequence
<220> FEATURE:
<223> OTHER INFORMATION: Synthetic

<400> SEQUENCE: 4
gcatgccatg ttatagtttg tgg                                              23

<210> SEQ ID NO 5
<211> LENGTH: 23
<212> TYPE: DNA
<213> ORGANISM: Artificial sequence
<220> FEATURE:
<223> OTHER INFORMATION: Synthetic

<400> SEQUENCE: 5
ggaggggcaa ggggcgggcg tgg                                              23

<210> SEQ ID NO 6
<211> LENGTH: 23
<212> TYPE: DNA
<213> ORGANISM: Artificial sequence
<220> FEATURE:
<223> OTHER INFORMATION: Synthetic

<400> SEQUENCE: 6
gctccggcta gttttcccgg ggg                                              23

<210> SEQ ID NO 7
<211> LENGTH: 23
<212> TYPE: DNA
<213> ORGANISM: Artificial sequence
<220> FEATURE:
<223> OTHER INFORMATION: Synthetic

<400> SEQUENCE: 7
gggcaagtac gtcgattcca agg                                              23

<210> SEQ ID NO 8
<211> LENGTH: 23
<212> TYPE: DNA
<213> ORGANISM: Artificial sequence
<220> FEATURE:
<223> OTHER INFORMATION: Synthetic

<400> SEQUENCE: 8
gggcgtgggc ctaacgacgc ggg                                              23

<210> SEQ ID NO 9
<211> LENGTH: 23
<212> TYPE: DNA
<213> ORGANISM: Artificial sequence
<220> FEATURE:
<223> OTHER INFORMATION: Synthetic

<400> SEQUENCE: 9
```

-continued gttccgcgtt acataactta cgg                                          23

<210> SEQ ID NO 10
<211> LENGTH: 23
<212> TYPE: DNA
<213> ORGANISM: Artificial sequence
<220> FEATURE:
<223> OTHER INFORMATION: Synthetic

<400> SEQUENCE: 10
tggcaccaca ccttctacaa tga                                          23

<210> SEQ ID NO 11
<211> LENGTH: 22
<212> TYPE: DNA
<213> ORGANISM: Artificial sequence
<220> FEATURE:
<223> OTHER INFORMATION: Synthetic

<400> SEQUENCE: 11
cagcctggat agcaacgtac at                                           22

<210> SEQ ID NO 12
<211> LENGTH: 20
<212> TYPE: DNA
<213> ORGANISM: Artificial sequence
<220> FEATURE:
<223> OTHER INFORMATION: Synthetic

<400> SEQUENCE: 12
agaacctgtc acaagctgtg                                              20

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
gacagcaagc tgaggatgtc                                              20

<210> SEQ ID NO 14
<211> LENGTH: 20
<212> TYPE: DNA
<213> ORGANISM: Artificial sequence
<220> FEATURE:
<223> OTHER INFORMATION: Synthetic

<400> SEQUENCE: 14
gggctctctg agaggcaggt                                              20

<210> SEQ ID NO 15
<211> LENGTH: 19
<212> TYPE: DNA
<213> ORGANISM: Artificial sequence
<220> FEATURE:
<223> OTHER INFORMATION: Synthetic

<400> SEQUENCE: 15
cctttgctct gcggttctg                                               19

<210> SEQ ID NO 16
<211> LENGTH: 19
<212> TYPE: DNA
<213> ORGANISM: Artificial sequence

```
<220> FEATURE:
<223> OTHER INFORMATION: Synthetic

<400> SEQUENCE: 16
acgccgagct cagcaagat                                                    19

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
tccacgtacg gcctcttctg                                                   20

<210> SEQ ID NO 18
<211> LENGTH: 22
<212> TYPE: DNA
<213> ORGANISM: Artificial sequence
<220> FEATURE:
<223> OTHER INFORMATION: Synthetic

<400> SEQUENCE: 18
gtggcgtgac ctgtggatgc tg                                                22

<210> SEQ ID NO 19
<211> LENGTH: 20
<212> TYPE: DNA
<213> ORGANISM: Artificial sequence
<220> FEATURE:
<223> OTHER INFORMATION: Synthetic

<400> SEQUENCE: 19
ggttagggtt agggttaggg                                                   20

<210> SEQ ID NO 20
<211> LENGTH: 1468
<212> TYPE: PRT
<213> ORGANISM: Artificial sequence
<220> FEATURE:
<223> OTHER INFORMATION: Synthetic

<400> SEQUENCE: 20

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140
```

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
        180                 185                 190

Asn Gln Leu Phe Glu Glu Asn Pro Ile Asn Ala Ser Gly Val Asp Ala
    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560
```

-continued

```
Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
```

```
              980             985             990
    Val Gly Thr Ala Leu Ile Lys Lys Tyr Pro Lys Leu Glu Ser Glu Phe
                995            1000            1005
    Val Tyr Gly Asp Tyr Lys Val Tyr Asp Val Arg Lys Met Ile Ala
       1010            1015            1020
    Lys Ser Glu Gln Glu Ile Gly Lys Ala Thr Ala Lys Tyr Phe Phe
       1025            1030            1035
    Tyr Ser Asn Ile Met Asn Phe Phe Lys Thr Glu Ile Thr Leu Ala
       1040            1045            1050
    Asn Gly Glu Ile Arg Lys Arg Pro Leu Ile Glu Thr Asn Gly Glu
       1055            1060            1065
    Thr Gly Glu Ile Val Trp Asp Lys Gly Arg Asp Phe Ala Thr Val
       1070            1075            1080
    Arg Lys Val Leu Ser Met Pro Gln Val Asn Ile Val Lys Lys Thr
       1085            1090            1095
    Glu Val Gln Thr Gly Gly Phe Ser Lys Glu Ser Ile Leu Pro Lys
       1100            1105            1110
    Arg Asn Ser Asp Lys Leu Ile Ala Arg Lys Lys Asp Trp Asp Pro
       1115            1120            1125
    Lys Lys Tyr Gly Gly Phe Asp Ser Pro Thr Val Ala Tyr Ser Val
       1130            1135            1140
    Leu Val Val Ala Lys Val Glu Lys Gly Lys Ser Lys Lys Leu Lys
       1145            1150            1155
    Ser Val Lys Glu Leu Leu Gly Ile Thr Ile Met Glu Arg Ser Ser
       1160            1165            1170
    Phe Glu Lys Asn Pro Ile Asp Phe Leu Glu Ala Lys Gly Tyr Lys
       1175            1180            1185
    Glu Val Lys Lys Asp Leu Ile Ile Lys Leu Pro Lys Tyr Ser Leu
       1190            1195            1200
    Phe Glu Leu Glu Asn Gly Arg Lys Arg Met Leu Ala Ser Ala Gly
       1205            1210            1215
    Glu Leu Gln Lys Gly Asn Glu Leu Ala Leu Pro Ser Lys Tyr Val
       1220            1225            1230
    Asn Phe Leu Tyr Leu Ala Ser His Tyr Glu Lys Leu Lys Gly Ser
       1235            1240            1245
    Pro Glu Asp Asn Glu Gln Lys Gln Leu Phe Val Glu Gln His Lys
       1250            1255            1260
    His Tyr Leu Asp Glu Ile Ile Glu Gln Ile Ser Glu Phe Ser Lys
       1265            1270            1275
    Arg Val Ile Leu Ala Asp Ala Asn Leu Asp Lys Val Leu Ser Ala
       1280            1285            1290
    Tyr Asn Lys His Arg Asp Lys Pro Ile Arg Glu Gln Ala Glu Asn
       1295            1300            1305
    Ile Ile His Leu Phe Thr Leu Thr Asn Leu Gly Ala Pro Ala Ala
       1310            1315            1320
    Phe Lys Tyr Phe Asp Thr Thr Ile Asp Arg Lys Arg Tyr Thr Ser
       1325            1330            1335
    Thr Lys Glu Val Leu Asp Ala Thr Leu Ile His Gln Ser Ile Thr
       1340            1345            1350
    Gly Leu Tyr Glu Thr Arg Ile Asp Leu Ser Gln Leu Gly Gly Asp
       1355            1360            1365
    Gly Thr Gly Gly Pro Lys Lys Lys Arg Lys Val Tyr Pro Tyr Asp
       1370            1375            1380
```

```
Val Pro Asp Tyr Ala Gly Tyr Pro Tyr Asp Val Pro Asp Tyr Ala
    1385                1390                1395

Gly Ser Tyr Pro Tyr Asp Val Pro Asp Tyr Ala Gly Ser Gly Ser
    1400                1405                1410

Gly Arg Ala Asp Ala Leu Asp Phe Asp Leu Asp Met Leu Gly
    1415                1420                1425

Ser Asp Ala Leu Asp Asp Phe Asp Leu Asp Met Leu Gly Ser Asp
    1430                1435                1440

Ala Leu Asp Asp Phe Asp Leu Asp Met Leu Gly Ser Asp Ala Leu
    1445                1450                1455

Asp Asp Phe Asp Leu Asp Met Leu Ile Asn
    1460                1465

<210> SEQ ID NO 21
<211> LENGTH: 1426
<212> TYPE: PRT
<213> ORGANISM: Artificial sequence
<220> FEATURE:
<223> OTHER INFORMATION: Synthetic

<400> SEQUENCE: 21

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

```
Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685
```

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Tyr
                965                 970                 975

Phe Phe Tyr Ser Asn Ile Met Asn Phe Phe Lys Thr Glu Ile Thr Leu
            980                 985                 990

Ala Asn Gly Glu Ile Arg Lys Arg Pro Leu Ile Glu Thr Asn Gly Glu
    995                 1000                1005

Thr Gly Glu Ile Val Trp Asp Lys Gly Arg Asp Phe Ala Thr Val
1010                1015                1020

Arg Lys Val Leu Ser Met Pro Gln Val Asn Ile Val Lys Lys Thr
1025                1030                1035

Glu Val Gln Thr Gly Gly Phe Ser Lys Glu Ser Ile Leu Pro Lys
1040                1045                1050

Arg Asn Ser Asp Lys Leu Ile Ala Arg Lys Lys Asp Trp Asp Pro
1055                1060                1065

Lys Lys Tyr Gly Gly Phe Asp Ser Pro Thr Val Ala Tyr Ser Val
1070                1075                1080

Leu Val Val Ala Lys Val Glu Lys Gly Lys Ser Lys Lys Leu Lys
1085                1090                1095

Ser Val Lys Glu Leu Leu Gly Ile Thr Ile Met Glu Arg Ser Ser 1100                1105                1110

Phe Glu Lys Asn Pro Ile Asp Phe Leu Glu Ala Lys Gly Tyr Lys
     1115                1120                1125

Glu Val Lys Lys Asp Leu Ile Ile Lys Leu Pro Lys Tyr Ser Leu
     1130                1135                1140

Phe Glu Leu Glu Asn Gly Arg Lys Arg Met Leu Ala Ser Ala Gly
     1145                1150                1155

Glu Leu Gln Lys Gly Asn Glu Leu Ala Leu Pro Ser Lys Tyr Val
     1160                1165                1170

Asn Phe Leu Tyr Leu Ala Ser His Tyr Glu Lys Leu Lys Gly Ser
     1175                1180                1185

Pro Glu Asp Asn Glu Gln Lys Gln Leu Phe Val Glu Gln His Lys
     1190                1195                1200

His Tyr Leu Asp Glu Ile Ile Glu Gln Ile Ser Glu Phe Ser Lys
     1205                1210                1215

Arg Val Ile Leu Ala Asp Ala Asn Leu Asp Lys Val Leu Ser Ala
     1220                1225                1230

Tyr Asn Lys His Arg Asp Lys Pro Ile Arg Glu Gln Ala Glu Asn
     1235                1240                1245

Ile Ile His Leu Phe Thr Leu Thr Asn Leu Gly Ala Pro Ala Ala
     1250                1255                1260

Phe Lys Tyr Phe Asp Thr Thr Ile Asp Arg Lys Arg Tyr Thr Ser
     1265                1270                1275

Thr Lys Glu Val Leu Asp Ala Thr Leu Ile His Gln Ser Ile Thr
     1280                1285                1290

Gly Leu Tyr Glu Thr Arg Ile Asp Leu Ser Gln Leu Gly Gly Asp
     1295                1300                1305

Gly Thr Gly Gly Pro Lys Lys Lys Arg Lys Val Tyr Pro Tyr Asp
     1310                1315                1320

Val Pro Asp Tyr Ala Gly Tyr Pro Tyr Asp Val Pro Asp Tyr Ala
     1325                1330                1335

Gly Ser Tyr Pro Tyr Asp Val Pro Asp Tyr Ala Gly Ser Met Asp
     1340                1345                1350

Ala Lys Ser Leu Thr Ala Trp Ser Arg Thr Leu Val Thr Phe Lys
     1355                1360                1365

Asp Val Phe Val Asp Phe Thr Arg Glu Glu Trp Lys Leu Leu Asp
     1370                1375                1380

Thr Ala Gln Gln Ile Val Tyr Arg Asn Val Met Leu Glu Asn Tyr
     1385                1390                1395

Lys Asn Leu Val Ser Leu Gly Tyr Gln Leu Thr Lys Pro Asp Val
     1400                1405                1410

Ile Leu Arg Leu Glu Lys Gly Glu Glu Pro Trp Leu Val
     1415                1420                1425

<210> SEQ ID NO 22
<211> LENGTH: 126
<212> TYPE: DNA
<213> ORGANISM: Artificial sequence
<220> FEATURE:
<223> OTHER INFORMATION: Synthetic

<400> SEQUENCE: 22
caccggtgtg caggtgagtg atcaagaacc tgctgacgtt ttagagctag aaatagcaag    60
ttaaaataag gctagtccgt tatcaacttg aaaaagtggc accgagtcgg tgcttttttt   120
gaattc                                                                          126

<210> SEQ ID NO 23
<211> LENGTH: 20
<212> TYPE: DNA
<213> ORGANISM: Artificial sequence
<220> FEATURE:
<223> OTHER INFORMATION: Synthetic

<400> SEQUENCE: 23
agggttaggg ttagggttag                                                            20

<210> SEQ ID NO 24
<211> LENGTH: 20
<212> TYPE: DNA
<213> ORGANISM: Artificial sequence
<220> FEATURE:
<223> OTHER INFORMATION: Synthetic

<400> SEQUENCE: 24
gttagggtta gggttagggt                                                            20

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25
ttagggttag ggttagggtt                                                            20

<210> SEQ ID NO 26
<211> LENGTH: 17
<212> TYPE: DNA
<213> ORGANISM: Artificial sequence
<220> FEATURE:
<223> OTHER INFORMATION: Synthetic

<400> SEQUENCE: 26
gggttagggt tagggtt                                                               17

<210> SEQ ID NO 27
<211> LENGTH: 13
<212> TYPE: DNA
<213> ORGANISM: Artificial sequence
<220> FEATURE:
<223> OTHER INFORMATION: Synthetic

<400> SEQUENCE: 27
tagggttagg gtt                                                                   13

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
tggaatggaa tggaatggaa                                                            20

<210> SEQ ID NO 29
<211> LENGTH: 20
<212> TYPE: DNA
<213> ORGANISM: Artificial sequence

```
<220> FEATURE:
<223> OTHER INFORMATION: Synthetic

<400> SEQUENCE: 29
tgtctgtgag gaagctcccc                                              20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
taagcatgga ccattccttc                                              20

<210> SEQ ID NO 31
<211> LENGTH: 18
<212> TYPE: DNA
<213> ORGANISM: Artificial sequence
<220> FEATURE:
<223> OTHER INFORMATION: Synthetic

<400> SEQUENCE: 31
gggccaggac ctctaaaa                                                18

<210> SEQ ID NO 32
<211> LENGTH: 18
<212> TYPE: DNA
<213> ORGANISM: Artificial sequence
<220> FEATURE:
<223> OTHER INFORMATION: Synthetic

<400> SEQUENCE: 32
ccggggaagt gctgagtc                                                18

<210> SEQ ID NO 33
<211> LENGTH: 18
<212> TYPE: DNA
<213> ORGANISM: Artificial sequence
<220> FEATURE:
<223> OTHER INFORMATION: Synthetic

<400> SEQUENCE: 33
tggtgggtgt agacacgg                                                18

<210> SEQ ID NO 34
<211> LENGTH: 24
<212> TYPE: DNA
<213> ORGANISM: Artificial sequence
<220> FEATURE:
<223> OTHER INFORMATION: Synthetic

<400> SEQUENCE: 34
ggttagggtt agggttaggg ttag                                         24

<210> SEQ ID NO 35
<211> LENGTH: 24
<212> TYPE: DNA
<213> ORGANISM: Artificial sequence
<220> FEATURE:
<223> OTHER INFORMATION: Synthetic

<400> SEQUENCE: 35
gttagggtta gggttagggt tagg                                         24
```

```
<210> SEQ ID NO 36
<211> LENGTH: 24
<212> TYPE: DNA
<213> ORGANISM: Artificial sequence
<220> FEATURE:
<223> OTHER INFORMATION: Synthetic

<400> SEQUENCE: 36
ttagggttag ggttagggtt aggg                                              24

<210> SEQ ID NO 37
<211> LENGTH: 24
<212> TYPE: DNA
<213> ORGANISM: Artificial sequence
<220> FEATURE:
<223> OTHER INFORMATION: Synthetic

<400> SEQUENCE: 37
tagggttagg gttagggtta gggt                                              24

<210> SEQ ID NO 38
<211> LENGTH: 24
<212> TYPE: DNA
<213> ORGANISM: Artificial sequence
<220> FEATURE:
<223> OTHER INFORMATION: Synthetic

<400> SEQUENCE: 38
ctccatcctg aaggaatggt ccat                                              24

<210> SEQ ID NO 39
<211> LENGTH: 20
<212> TYPE: DNA
<213> ORGANISM: Artificial sequence
<220> FEATURE:
<223> OTHER INFORMATION: Synthetic

<400> SEQUENCE: 39
atggaatgga atggaatgga                                                   20

<210> SEQ ID NO 40
<211> LENGTH: 102
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, t or u

<400> SEQUENCE: 40
gnnnnnnnnn nnnnnnnnnn nguuuaagag cuaugcuggc cacggugaaa aaguucaacu       60
auugccugau cggaauaaau uugaacgaua cgaccggugc uu                         102

<210> SEQ ID NO 41
<211> LENGTH: 104
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n is a, c, g, t or u

<400> SEQUENCE: 41
```
gnnnnnnnnn nnnnnnnnnn ngucuuugua cucucaagau acugcccac aacuaaagcc    60 guacuucgga uagaaacauc gaagacguuc uauggcaggg uguu    104

<210> SEQ ID NO 42
<211> LENGTH: 137
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(24)
<223> OTHER INFORMATION: n is a, c, g, t or u

<400> SEQUENCE: 42
gnnnnnnnnn nnnnnnnnnn nnnguugua gcucccuuuc ucauuucgcg aaauucccccg    60 ucucgcaacg ccguguagaa aagucugccg gaauaacauc guugccaaga guaaagcgcu   120
uuaaggggca ucguuua    137

<210> SEQ ID NO 43
<211> LENGTH: 36
<212> TYPE: DNA
<213> ORGANISM: Artificial sequence
<220> FEATURE:
<223> OTHER INFORMATION: Synthetic

<400> SEQUENCE: 43
ttagggttag ggttagggtt agggttaggg ttaggg    36

<210> SEQ ID NO 44
<211> LENGTH: 27
<212> TYPE: DNA
<213> ORGANISM: Artificial sequence
<220> FEATURE:
<223> OTHER INFORMATION: Synthetic

<400> SEQUENCE: 44
ctgctgctgc tgctgctgct gctgctg    27

<210> SEQ ID NO 45
<211> LENGTH: 27
<212> TYPE: DNA
<213> ORGANISM: Artificial sequence
<220> FEATURE:
<223> OTHER INFORMATION: Synthetic

<400> SEQUENCE: 45
cagcagcagc agcagcagca gcagcag    27

<210> SEQ ID NO 46
<211> LENGTH: 125
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(24)
<223> OTHER INFORMATION: n is a, c, g, t or u

<400> SEQUENCE: 46
gnnnnnnnnn nnnnnnnnnn nnnguugua gcucccuuuc ucgaaagaga accguugcua    60
caauaaggcc gucugaaaag augugccgca acgcucugcc ccuuaaagcu ucugcuuuaa   120

```
ggggc                                                                125
```

<210> SEQ ID NO 47
<211> LENGTH: 144
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(23)
<223> OTHER INFORMATION: n is a, c, g, t or u

<400> SEQUENCE: 47

```
gnnnnnnnnn nnnnnnnnnn nnnguuguag cucccuuucu cauuucggaa acgaaaugag    60
aaccguugcu acaauaaggc cgucugaaaa gaugugccgc aacgcucugc cccuuaaagc   120
uucugcuuua aggggcaucg uuua                                         144
```

<210> SEQ ID NO 48
<211> LENGTH: 104
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is a, c, g, t or u

<400> SEQUENCE: 48

```
gnnnnnnnnn nnnnnnnnnn guuuuuguac ucucagaaau gcagaagcua caaagauaag    60
gcuucaugcc gaaaucaaca cccugucauu uauggcaggg uguu                   104
```

<210> SEQ ID NO 49
<211> LENGTH: 100
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is a, c, g, t or u

<400> SEQUENCE: 49

```
gnnnnnnnnn nnnnnnnnnn gucuuuguac ucugaaaaga agcuacaaag auaaggcuuc    60
augccgaaau caacacccug ucauuuuaug gcagggguguu                       100
```

<210> SEQ ID NO 50
<211> LENGTH: 105
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is a, c, g, t or u

<400> SEQUENCE: 50

```
gnnnnnnnnn nnnnnnnnnn gucuuuguac ucucagaaau gcagaagcua caaagauaag    60
gcuucaugcc gaaaucaaca cccugucauu cuauggcagg guguu                  105
```

<210> SEQ ID NO 51
<211> LENGTH: 104

<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is a, c, g, t or u

<400> SEQUENCE: 51
gnnnnnnnnn nnnnnnnnnn gucuuuguac ucucaagaua cugucccaca acuaaagccg    60
uacuucggaa uagaaacauc gaagacguuc uauggcaggg uguu                    104

<210> SEQ ID NO 52
<211> LENGTH: 121
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(20)
<223> OTHER INFORMATION: n is a, c, g, t or u

<400> SEQUENCE: 52
gnnnnnnnnn nnnnnnnnnn gucuuuguac ucucaagauu uaagaaauua aaucuugcag    60
aagcuacaaa gauaaggcuu caugccgaaa ucaacacccu gucauucuau ggcagggugu   120
u                                                                   121

<210> SEQ ID NO 53
<211> LENGTH: 14
<212> TYPE: DNA
<213> ORGANISM: Artificial sequence
<220> FEATURE:
<223> OTHER INFORMATION: Synthetic

<400> SEQUENCE: 53
tgatatcaca gtgg                                                      14

<210> SEQ ID NO 54
<211> LENGTH: 23
<212> TYPE: DNA
<213> ORGANISM: Artificial sequence
<220> FEATURE:
<223> OTHER INFORMATION: Synthetic

<400> SEQUENCE: 54
ccagtctgga cgacagcaag acc                                            23

<210> SEQ ID NO 55
<211> LENGTH: 23
<212> TYPE: DNA
<213> ORGANISM: Artificial sequence
<220> FEATURE:
<223> OTHER INFORMATION: Synthetic

<400> SEQUENCE: 55
gataaccacc aaagcgagac agg                                            23

<210> SEQ ID NO 56
<211> LENGTH: 23
<212> TYPE: DNA
<213> ORGANISM: Artificial sequence
<220> FEATURE:
<223> OTHER INFORMATION: Synthetic

<400> SEQUENCE: 56
cctccggtgg attaatggat aaa                                      23

<210> SEQ ID NO 57
<211> LENGTH: 23
<212> TYPE: DNA
<213> ORGANISM: Artificial sequence
<220> FEATURE:
<223> OTHER INFORMATION: Synthetic

<400> SEQUENCE: 57
ccttcaatgg gttcttgagg aca                                      23

<210> SEQ ID NO 58
<211> LENGTH: 40
<212> TYPE: DNA
<213> ORGANISM: Artificial sequence
<220> FEATURE:
<223> OTHER INFORMATION: Synthetic

<400> SEQUENCE: 58
ggaatggaat ggaatggaat ggaatggaat ggaatggaat                    40

<210> SEQ ID NO 59
<211> LENGTH: 60
<212> TYPE: DNA
<213> ORGANISM: Artificial sequence
<220> FEATURE:
<223> OTHER INFORMATION: Synthetic

<400> SEQUENCE: 59
ggggccgggg ccgggccgg ggccggggcc ggggccgggg ccgggccgg ggccggggcc    60

<210> SEQ ID NO 60
<211> LENGTH: 60
<212> TYPE: DNA
<213> ORGANISM: Artificial sequence
<220> FEATURE:
<223> OTHER INFORMATION: Synthetic

<400> SEQUENCE: 60
ccccggcccc ggccccggcc ccggccccgg ccccggcccc ggccccggcc ccggggggcc    60

<210> SEQ ID NO 61
<211> LENGTH: 54
<212> TYPE: DNA
<213> ORGANISM: Artificial sequence
<220> FEATURE:
<223> OTHER INFORMATION: Synthetic

<400> SEQUENCE: 61
ctgctgctgc tgctgctgct gctgctgctg ctgctgctgc tgctgctgct gctg       54

<210> SEQ ID NO 62
<211> LENGTH: 54
<212> TYPE: DNA
<213> ORGANISM: Artificial sequence
<220> FEATURE:
<223> OTHER INFORMATION: Synthetic

<400> SEQUENCE: 62
gacgacgacg acgacgacga cgacgacgac gacgacgacg acgacgacga cgac       54

<210> SEQ ID NO 63
<211> LENGTH: 38

```
<212> TYPE: DNA
<213> ORGANISM: Artificial sequence
<220> FEATURE:
<223> OTHER INFORMATION: Synthetic

<400> SEQUENCE: 63
agtgaagctc ctctgtatga tatcacagtg gtagatat                              38

<210> SEQ ID NO 64
<211> LENGTH: 23
<212> TYPE: DNA
<213> ORGANISM: Artificial sequence
<220> FEATURE:
<223> OTHER INFORMATION: Synthetic

<400> SEQUENCE: 64
tcctctgtat gatatcacag tgg                                              23

<210> SEQ ID NO 65
<211> LENGTH: 16
<212> TYPE: DNA
<213> ORGANISM: Artificial sequence
<220> FEATURE:
<223> OTHER INFORMATION: Synthetic

<400> SEQUENCE: 65
ttagggttag ggttag                                                      16

<210> SEQ ID NO 66
<211> LENGTH: 28
<212> TYPE: DNA
<213> ORGANISM: Artificial sequence
<220> FEATURE:
<223> OTHER INFORMATION: Synthetic

<400> SEQUENCE: 66
ctaaccctaa ccctaaccct aaccctaa                                         28

<210> SEQ ID NO 67
<211> LENGTH: 99
<212> TYPE: DNA
<213> ORGANISM: Artificial sequence
<220> FEATURE:
<223> OTHER INFORMATION: Synthetic

<400> SEQUENCE: 67
guuaggguua gggguuagggu uguuugagag cuagaaaaua gcaagucaaa uaaggcuagu     60
ccguuaucaa cuugaaaaag uggcaccgag ucggugcuu                             99

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
tgcttccctg agacccagtt                                                  20

<210> SEQ ID NO 69
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 69
gatcacttct ttcctttgca tcaag                                          25
```

COMPOSITIONS AND METHODS FOR DIFFERENTIAL CAS9 GENE LABELING AND/OR EDITING

CROSS-REFERENCED TO RELATED APPLICATIONS

This application is a continuation of and claims priority to, co-pending U.S. Non-Provisional application Ser. No. 14/571,818, filed Dec. 16, 2014, currently pending, and U.S. Provisional Application Ser. No. 61/917,003, filed Dec. 17, 2013, each of which is herein incorporated by reference in its entirety.

A Sequence Listing has been submitted in an ASCII text file named "17909RevisedST25" created on Jul. 14, 2021, consisting of 39,755 bytes, the entire content of which is herein incorporated by reference.

STATEMENT OF GOVERNMENTAL SUPPORT

This invention was made with government support awarded by the National Institutes of Health, Grant Nos. GM068110, HG006193 and GM102515. The government has certain rights in the invention.

FIELD OF THE INVENTION

The present disclosure relates to methods of and systems for modifying the transcriptional regulation of stem or progenitor cells to promote their differentiation or reprogramming of somatic cells. Further, the invention related to methods of and systems for target-sequence specific gene editing and labeling.

BACKGROUND OF THE INVENTION

Recently, an RNA-guided adaptive immune system that is widespread in bacteria and archaea [1] has been engineered for targeted DNA cleavage or gene regulation in prokaryotic and eukaryotic genomes [2]. Such a system could provide a platform for the systematic and high throughput identification of factors relevant to stem cell differentiation and maintenance if applicable to human pluripotent stem cells (hPSCs) or other multipotent progenitor cells. Clustered Regularly Interspaced Short Palindromic Repeat (CRISPR) RNA sequences and CRISPR-associated (Cas) genes generate a catalytic protein-RNA complex that utilize the incorporated RNA to generate sequence-specific double strand breaks at a complementary DNA sequence [3]. The Cas9 nuclease from *Streptococcus pyogenes* (hereafter, Cas9 or spCas9) can be guided to specific sites in the human genome through base-pair complementation between a 20 nucleotide guide region of an engineered single guide RNA (sgRNA) and a genomic target sequence [4-7]. Type II Cas9 orthologs from other species display similar properties, but have different specificities and CRISPR RNA sequences. Esvelt et al. (2013). Orthogonal Cas9 proteins for RNA-guided gene regulation and editing. *Nature Methods*, 10(11), 1116-1121.

A catalytically-inactive programmable RNA-dependent DNA-binding protein (dCas9) can be generated by mutating the endonuclease domains within Cas9 [8], which can modulate transcription in bacteria or eukaryotes either directly [8, 9] or through an incorporated effector domain [10-14]. However, the ability of a dCas9-effector system (referred to herein as CRISPRe) to influence the differentiation status of stem cells has not been addressed.

What is needed is a system that can be used to promote differentiation of a stem, progenitor or precursor cell population and could potentially be used in a directed approach to identify genes related to cell differentiation down desired lineage pathways.

In additional the functional organization of a cell nucleus is a major domain in the theater of contemporary cell biology and is increasingly being studied in real-time, live cell approaches. For example, the 3-D arrangement of the chromosomes in the interphase nucleus can be investigated by chromosome capture. (Dekker et al., (2013). Exploring the three-dimensional organization of genomes: interpreting chromatin interaction data. *Nature Reviews Genetics,* 14(6), 390-403. Meanwhile, other methods to fluorescently label specific genomic loci in live cells were reported, for example, those based on Transcription Activator-Like Effectors, or TALEs. Ma et al., Proc. Natl. Acad. Sci. USA 110: 21048-21053, (2013). By utilizing orthogonal dCas9 platforms fused to different fluorescent proteins, multiplex labeling and editing of target loci can be achieved such as trinucleotide repeat expansion loci.

SUMMARY OF THE INVENTION

The present disclosure relates to methods of and systems for modifying the transcriptional regulation of stem or progenitor cells to promote their differentiation or reprogramming of somatic cells. Further, the invention is related to methods of and systems for multiplex target-sequence specific gene editing and labeling.

In one embodiment, the present invention contemplates a method, comprising: a) providing; i) at least one stem cell comprising at least one specific genomic target; and ii) a first and second lentiviral vectors, wherein said first lentiviral vector encodes a nuclease deficient Cas9-effector domain fusion protein and said second lentiviral vector comprises at least one sgRNA gene complementary with said specific genomic sequence; b) expressing said first and second lentiviral vectors in said at least one stem cell wherein a nuclease deficient Cas9-effector domain fusion protein/sgRNA complex is formed; and c) regulating an artificial transcription of said specific genomic target with said nuclease deficient Cas9-effector domain fusion protein/sgRNA complex. In one embodiment, the at least one stem cell comprises a progenitor cell. In one embodiment, the regulating transcription is selected from the group consisting of enhancement of transcriptional activity and repression of transcriptional activity. In one embodiment, the specific genomic target is selected from the group consisting of a genomic region and a gene. In one embodiment, the said first and second lentiviral vectors comprise a single vector. In one embodiment, the at least one sgRNA gene targets an intrachromosomal genomic sequence. In one embodiment, the at least one sgRNA gene targets an interchromosomal genomic sequence. In one embodiment, the artificial regulation of transcription results in a phenotypic change of said at least one stem cell. In one embodiment, the effector domain is selected from the group consisting of an activation domain, a repression domain, a protein modification domain, a histone modification domain, a DNA modification domain and a RNA modification domain. In one embodiment, the regulating transcription modulates differentiation of said at least one stem cell. In one embodiment, the first and second lentiviral vectors comprise a promoter selected from the group consisting of a constitutive promoter and an inducible promoter.

In one embodiment, the present invention contemplates a method, comprising: a) providing: i) at least one somatic cell comprising a specific genomic target; and ii) a first and second lentiviral vectors, wherein said first lentiviral vector encodes a nuclease deficient Cas9-effector domain fusion protein and said second lentiviral vector comprises at least one sgRNA gene complementary to said specific genomic target; b) expressing said first and second lentiviral vectors within said at least one somatic cell wherein a nuclease deficient Cas9-effector domain fusion protein/sgRNA complex is formed; and c) regulating transcription of said specific genomic target with said nuclease deficient Cas9-effector domain fusion protein/sgRNA complex, wherein a reprogrammed undifferentiated induced pluripotent somatic stem cell is created. In one embodiment, the specific genomic target is selected from the group consisting of OCT4, SOX2, KLF4, and cMYC. In one embodiment, the somatic cell is selected from the group consisting of a mesenchymal somatic cell, a fibroblast somatic cell, a cardiomyocyte somatic cell culture, a hematopoietic cell culture, and a pancreatic beta somatic cell culture. In one embodiment, non-integrating or excisable expression systems for nuclease-deficient Cas9 fused with effector domain gene and said sgRNA gene are utilized. In one embodiment, said somatic cell culture is selected from the group consisting of a mesenchymal somatic cell, a fibroblast somatic cell, a cardiomyocyte somatic cell culture, a hematopoietic cell culture, and a pancreatic beta somatic cell culture. In one embodiment, said effector domain is a modified transcription factor.

In one embodiment, the present invention contemplates a method, comprising; a) providing: i) at least one reprogrammed undifferentiated induced pluripotent somatic stem cell comprising a specific genomic target; and ii) a first and second lentiviral vectors, wherein said first lentiviral vector encodes a nuclease deficient Cas9-effector domain fusion protein and said second lentiviral vector comprises at least one sgRNA gene complementary to the specific genomic target; b) expressing said first and second lentiviral vectors wherein a nuclease deficient Cas9-effector domain fusion protein/sgRNA complex is formed; c) regulating transcription of the specific genomic target with said nuclease deficient Cas9-effector domain fusion protein/sgRNA complex wherein a differentiated somatic cell is created. In one embodiment, the differentiated somatic cell is selected from the group consisting of a fibroblast cell and a HGPS fibroblast cell. In one embodiment, the reprogrammed induced pluripotent somatic stem cell is selected from the group consisting of a neuronal cell, a motoneuron cell, a cortical neuron cell and an astrocyte cell. In one embodiment, the reprogrammed induced pluripotent somatic stem cell is selected from the group consisting of a mesenchymal somatic cell, a fibroblast somatic cell, a cardiomyocyte somatic cell, a hematopoietic cell and a pancreatic beta somatic cell. In one embodiment, the reprogrammed induced pluripotent somatic stem cell is selected from the group consisting of a pancreatic endocrine cell, a cardiomyocyte cell, a thymic epithelial cell and a thyroid cell. In one embodiment, the regulating transcription of said specific genomic target results in a phenotypic change of said reprogrammed induced pluripotent somatic stem cell. In one embodiment, the regulating transcription is selected from the group consisting of enhancement of transcriptional activity and repression of transcriptional activity. In one embodiment, the specific genomic target is selected from the group consisting of a genomic region and a gene. In one embodiment, the first and second lentiviral vectors comprise a single vector. In one embodiment, the at least one sgRNA gene targets an intrachromosomal genomic target. In one embodiment, the at least one sgRNA gene targets an interchromosomal genomic target. In one embodiment, the first and second lentiviral vectors comprise a promoter selected from the group consisting of a constitutive promoter and an inducible promoter.

In one embodiment, the present invention contemplates a method, comprising: a) providing; i) at least one cell comprising a plurality of specific genomic targets; ii) an integration-deficient lentiviral vector encoding a plurality of nuclease deficient Cas9-effector domain fusion protein; and iii) a plurality of sgRNA genes each of which is complementary with at least one of said plurality of specific genomic targets; b) delivering said integration-deficient lentiviral vector and said plurality of sgRNA genes to said at least one cell; c) expressing said integration-deficient lentiviral vector in said at least one cell wherein a plurality of nuclease deficient Cas9-effector domain fusion protein/sgRNA complexes are formed; and d) regulating transcription of said plurality of specific genomic targets with said plurality of said nuclease deficient Cas9-effector domain fusion protein/sgRNA complexes. In one embodiment, the cell is selected from the group including a stem cell, a somatic cell or a reprogrammed induced somatic cell. In one embodiment, the delivering is selected from the group consisting of electroporation, nucleofection and transient transfection. In one embodiment, the delivering comprises a cell permeable nuclease deficient Cas9-effector domain fusion protein/sgRNA complex. In one embodiment, the regulating transcription activates the specific genomic target. In one embodiment, the regulating transcription represses the specific genomic target. In one embodiment, the regulating transcription differentiates the at least one cell. In one embodiment, the regulating transcription reprograms the at least one cell. In one embodiment, each of said plurality of sgRNA genes is complementary to a different genomic target sequence. In one embodiment, the different genomic target sequence is an intrachromosomal target sequence. In one embodiment, the different genomic target sequence is an interchromosomal target sequence. In one embodiment, the method further provides two orthogonal nuclease deficient Cas9-effector domain fusion proteins that are delivered with two orthogonal sgRNA genes thereby regulating two different types of transcription. In one embodiment, the transcriptional regulation of a cell culture results in phenotypic change in the treated cell culture. In one embodiment, said effector domain represses transcription of the at least one specific genomic target. In one embodiment, said effector domain activates transcription of said at least one specific genomic target. In one embodiment, said effector domain is a histone modification domain. In one embodiment, said effector domain is a DNA modification domain. In one embodiment, said effector domain is a RNA modification domain. In one embodiment, wherein said specific genomic target is upstream relative to an open reading frame. In one embodiment, wherein said specific genomic target is upstream of a transcribed non-coding RNA. In one embodiment, said transcriptional regulation modulates cell differentiation. In one embodiment, said first lentiviral vector comprises a promoter. In one embodiment, said promoter is a constitutive promoter. In one embodiment, said promoter is an inducible promoter. In one embodiment, said second lentiviral vector comprises a promoter. In one embodiment, said promoter is a constitutive promoter. In one embodiment, said promoter is an inducible promoter.

In one embodiment, the present invention contemplates a kit, comprising: a) a first container comprising a first vector encoding a nuclease deficient Cas9-effector domain fusion protein; b) a second container comprising a second vector comprising at least one sgRNA gene; c) a set of instructions comprising at least one method for transfecting a cell with said first and second vectors. In one embodiment, the kit further comprises a third container comprising an orthogonal first vector encoding a nuclease deficient Cas9-effector domain fusion protein. In one embodiment, the kit further comprises a fourth container comprising an orthogonal second vector comprising at least one sgRNA gene. In one embodiment, the set of instructions further comprise at least one method for differentiating a pluripotent stem cell into a somatic cell with said first and second vectors. In one embodiment, the set of instructions further comprise at least one method for reprogramming a somatic cell into an induced pluripotent stem cell with said first and second vectors. In one embodiment, the somatic cell is selected from the group consisting of a mesenchymal somatic cell, a fibroblast somatic cell, a cardiomyocyte somatic cell, a hematopoietic cell, a neuronal somatic cell, a fibroblast somatic cell, a midbrain dopamine somatic cell, and a pancreatic beta somatic cell.

In one embodiment, the present invention contemplates a kit, comprising: a) a first container comprising a first vector encoding a catalytically active Cas9-fluorescent protein fusion protein; b) a second container comprising a second vector comprising at least one full length sgRNA gene; c) a set of instructions comprising at least one method for editing a specific genomic target within a cell with said first and second vectors. In one embodiment, the kit further comprises a third container comprising a third vector comprising at least one truncated sgRNA gene. In one embodiment, the set of instructions further comprise at lest one method for labelling a specific genomic target within a cell with said first and second vectors. In one embodiment, the fluorescent protein fusion protein is selected from the group consisting of a red fluorescent protein, a blue fluorescent protein and a green fluorescent protein.

In some embodiments, the kits can optionally include enzymes capable of performing PCR (i.e., for example, DNA polymerase, Taq polymerase and/or restriction enzymes)

In some embodiments, the kits can optionally include a delivery vehicle for said vectors (e.g., a liposome). The reagents may be provided suspended in the excipient and/or delivery vehicle or may be provided as a separate component which can be later combined with the excipient and/or delivery vehicle.

In some embodiments, the kits may optionally contain additional therapeutics to be co-administered with the vectors to affect the desired transcriptional regulation.

In some embodiments, the kits may also optionally include appropriate systems (e.g. opaque containers) or stabilizers (e.g. antioxidants) to prevent degradation of the reagents by light or other adverse conditions.

In some embodiments, the kits may optionally include instructional materials containing directions (i.e., protocols) providing for the use of the reagents in affecting transcriptional regulation of cell cultures and delivery of said vectors to said cell cultures. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

It is not intended that embodiments of the invention be limited to any particular method, stem cell line, or delivery system. It is not intended that embodiments of the invention be limited to stem cells, but explicitly includes progenitors cells. It is not intended that embodiments of the invention be limited to human cells. It is not intended that embodiments of the invention be limited to any particular mechanism; however, it is believed that the interchangeability of target sequences provides a method to stepwise, in series or in parallel, differentiate pluripotent stem cells or multipotent stem cells to specifically desired differentiated cells and may subsequently be used for both research and medical purposes.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein, the term "stem cells" refers to undifferentiated biological cells, that can differentiate into specialized cells and can divide (through mitosis) to produce more stem cells. For the purposes of this document, progenitor cells are considered a type of stem cell. As used herein, the term "progenitor cells" refers to biological cells that, like a stem cells, have a tendency to differentiate into a specific type of cell, but is already more specific than a stem cell and is pushed to differentiate into its "target" cell. The most important difference between stem cells and progenitor cells is that stem cells can replicate indefinitely, whereas progenitor cells can divide only a limited number of times.

As used herein, the term "pluripotent cell" or "pluripotent stem cell" refers to a stem cell that has the potential to differentiate into any of the three germ layers: endoderm (interior stomach lining, gastrointestinal tract, the lungs), mesoderm (muscle, bone, blood, urogenital), or ectoderm (epidermal tissues and nervous system). Albeit, cell pluripotency is a continuum, ranging from the completely pluripotent cell that can form every cell of the embryo proper, e.g., embryonic stem cells and iPSCs, to the incompletely or partially pluripotent cell that can form cells of all three germ layers but that may not exhibit all the characteristics of completely pluripotent cells.

As used herein, the term "induced pluripotent stem cells" commonly abbreviated as iPS cells or iPSCs, refers to a type of pluripotent stem cell artificially derived from a non-pluripotent cell—typically an adult somatic cell—by inducing a "forced" expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed [15]. Induced pluripotent cells have been made from adult stomach, liver, skin cells, blood cells, prostate cells and urinary tract cells [16].

As used herein, the term "multipotent stem cell" refers to a stem cell that has the potential to differentiate into a number of different cell lineages, but is not pluripotent. For example, hematopoietic stem cells can generate all myeloid and lymphoid cell types.

As used herein, the term "ESC" or "embryonic stem cell" refer to pluripotent stem cells derived from the inner cell mass of a blastocyst, an early-stage embryo [17].

As used herein, the term "iPSC" or "iPS cell" or "induced pluripotent stem cell" refer to a type of pluripotent stem cell artificially derived from a non-pluripotent cell—typically an adult somatic cell—by inducing a "forced" expression of specific genes that reestablish the pluripotency program.

As used herein, the term "transcriptional regulation" refers to effectors that the change gene expression levels by altering the rate of transcription. These can be through direct effects on the transcriptional machinery or indirect effects on local chromatin architecture or epigenetic modifications.

As used herein, the term "edit" "editing" or "edited" refers to a method of altering a nucleic acid sequence of a polynucleotide (e.g., for example, a wild type naturally occurring nucleic acid sequence or a mutated naturally occurring sequence) by selective deletion of a specific genomic target. Such a specific genomic target includes, but is not limited to, a chromosomal region, a gene, a promoter, an open reading frame or any nucleic acid sequence.

As used herein, the term "specific genomic target" refers to a pre-identified nucleic acid sequence of any composition and/or length. Such a specific genomic target includes, but is not limited to, a chromosomal region, a gene, a promoter, an open reading frame or any nucleic acid sequence. In some embodiments, the present invention interrogates these specific genomic target sequences with complementary sequences of sgRNA.

As used herein, the term "lentiviral vector" refers to a gene delivery vehicle adapted from lentiviruses, a subclass of Retroviruses. Lentiviruses have recently been adapted as gene delivery vehicles (vectors) thanks to their ability to integrate into the genome of non-dividing cells, which is the unique feature of Lentiviruses as other Retroviruses can infect only dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides. The site of integration is unpredictable, which can pose a problem. The provirus can disturb the function of cellular genes and lead to activation of oncogenes promoting the development of cancer, which raises concerns for possible applications of lentiviruses in gene therapy. However, studies have shown that lentivirus vectors have a lower tendency to integrate in places that potentially cause cancer than gamma-retroviral vectors [18]. More specifically, one study found that lentiviral vectors did not cause either an increase in tumor incidence or an earlier onset of tumors in a mouse strain with a much higher incidence of tumors [19]. Moreover, clinical trials that utilized lentiviral vectors to deliver gene therapy for the treatment of HIV experienced no increase in mutagenic or oncologic events [20]. Finally, non-integrating lentivirus can be created by utilizing a non-functional integrase gene, which facilitates the delivery of the viral genome to the target cell without incorporation into the host genome. For safety reasons lentiviral vectors never carry the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the $\psi$ (psi) sequence. This sequence is used to package the genome into the virion.

As used herein, the term "CRISPRs" or "Clustered Regularly Interspaced Short Palindromic Repeats" refers to an acronym for DNA loci that contain multiple, short, direct repetitions of base sequences. Each repetition contains a series of bases followed by the same series in reverse and then by 30 or so base pairs known as "spacer DNA". The spacers are short segments of DNA from a virus and may serve as a 'memory' of past exposures to facilitate an adaptive defense against future invasions [21].

As used herein, the tem "Cas" or "CRISPR-associated (cas)" refers to genes often associated with CRISPR repeat-spacer arrays.

As used herein, the term "Cas9" refers to a nuclease from Type II CRISPR systems, an enzyme specialized for generating double-strand breaks in DNA, with two active cutting sites (the HNH and RuvC domains), one for each strand of the double helix. Jinek combined tracrRNA and spacer RNA into a "single-guide RNA" (sgRNA) molecule that, mixed with Cas9, could find and cleave DNA targets through Watson-Crick pairing between the guide sequence within the sgRNA and the target DNA sequence [22].

As used herein, the term "nuclease deficient Cas9" refers to a modified Cas9 nuclease wherein the nuclease activity has been disabled by mutating residues in the RuvC and HNH catalytic domains. Disabling of both cleavage domains can convert Cas9 from a RNA-programmable nuclease into an RNA-programmable DNA recognition complex to deliver effector domains to specific target sequences (Qi, et al. 2013 [8] and Gilbert, et al. 2013 [10]).

As used herein, the term "catalytically active Cas9" refers to an unmodified Cas9 nuclease comprising full nuclease activity.

As used herein, the term "effector domain" refers to a protein domain that can: 1) affect either transcriptional repression or activation, 2) catalytically modify histones, or 3) catalytically chemically modify DNA.

As used herein, the term "fluorescent protein" refers to a protein domain that comprises at least one organic compound moiety that emits fluorescent light in response to the appropriate wavelengths. For example, fluorescent proteins may emit red, blue and/or green light. Such proteins are readily commerically available including, but not limited to: i) mCherry (Clonetech Laboratories): excitation: 556/20 nm (wavelength/bandwidth); emission: 630/91 nm; ii) sfGFP (Invitrogen): excitation: 470/28 nm; emission: 512/23 nm; iii) TagBFP (Evrogen): excitation 387/11 nm; emission 464/23 nm.

As used herein, the term "sgRNA" refers to single guide RNA used in conjunction with CRISPR associated systems (Cas). sgRNAs contains nucleotides of sequence complementary to the desired target site. Watson-crick pairing of the sgRNA with the target site recruits the nuclease-deficient Cas9 to bind the DNA at that locus.

As used herein, the term "orthogonal" refers targets that are non-overlapping, uncorrelated, or independent. For example, if two orthogonal nuclease-deficient Cas9 gene fused to a different effector domains were implemented, they sgRNAs coded for each would not cross-talk or overlap. Not all nuclease-deficient Cas9 genes operate the same, which enables the use of orthogonal nuclease-deficient Cas9 gene fused to a different effector domains provided the appropriate orthogonial sgRNAs.

As used herein, the term "phenotypic change" or "phenotype" refers to the composite of an organism's observable characteristics or traits, such as its morphology, development, biochemical or physiological properties, phenology, behavior, and products of behavior. Phenotypes result from the expression of an organism's genes as well as the influence of environmental factors and the interactions between the two.

As used herein, the term "promoter" refers to a region of DNA that initiates transcription of a particular gene. Promoters are located near the genes they transcribe, on the same strand and upstream of the transcribed DNA (towards the 3' region of the anti-sense strand, also called template strand and non-coding strand).

As used herein, the term "constitutive promoter" refers to promoters that are active in all circumstances in the cell.

As used herein, the term "inducible promoter" or "regulated promoter" refers to promoters that become active in response to specific stimuli.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The term "an isolated nucleic acid", as used herein, refers to any nucleic acid molecule that has been removed from its natural state (e.g., removed from a cell and is, in a preferred embodiment, free of other genomic nucleic acid).

The terms "amino acid sequence" and "polypeptide sequence" as used herein, are interchangeable and to refer to a sequence of amino acids.

As used herein the term "portion" when in reference to a protein (as in "a portion of a given protein") refers to fragments of that protein. The fragments may range in size from four amino acid residues to the entire amino acid sequence minus one amino acid.

The term "portion" when used in reference to a nucleotide sequence refers to fragments of that nucleotide sequence. The fragments may range in size from 5 nucleotide residues to the entire nucleotide sequence minus one nucleic acid residue.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed to a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" is defined herein as an oligonucleotide sequence which exhibits greater than or equal to 50% identity to a sequence, when sequences having a length of 100 bp or larger are compared.

Low stringency conditions comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent {50×Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m = 81.5 + 0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "transfection" or "transfected" refers to the introduction of foreign DNA into a cell.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference). The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

BRIEF DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A-C shows a schematic overview of the CRISPR system. FIG. 1A shows S. pyogenes Cas9 (spCas9) recognizes a target sequence through Watson-Crick pairing of 20 bases of the sgRNA and recognition of the neighboring PAM sequence (NGG) by the protein (Jinek 2012 [23]). FIG. 1B shows N. meningitidis Cas9 (nmCas9) utilizes a 24 base guide sequence in its sgRNA and the neighboring PAM sequence (NNNNGANN or NNNNGTTN) for target recognition (Esvelt, et al. [24]). FIG. 1C shows a nuclease dead dspCas9/sgRNA complex tethered to a repression domain can be programmed for targeted down regulation of a single or set of genes (Gene X). This may be employed with an orthogonal nuclease dead dnmCas9/sgRNA complex tethered to an activation domain for targeted upregulation of a different set of genes (Gene Y).

FIG. 2A-D shows CRISPRe can upregulate expression of a developmentally relevant transcription factor in hESCs. FIG. 2A shows a genomic view of the SOX17 locus, showing the sgRNA targets, and key epigenetic marks indicating the active (H3K4me3) or repressed (H3K27me3) status, and overall accessibility (Dnase I) of the gene and its surrounding genomic area. FIG. 2B shows a schematic of the constitutive EF1α-regulated dCas9-VP64 and SOX17 sgRNA constructs. FIG. 2C shows a quantitative gene expression analysis of EF1α-regulated dCas9-VP64 cells transduced with SOX17 sgRNAs. Data is expressed as fold over hESCs+/−SD. FIG. 2D shows an immunofluorescence analysis of SOX17 in EF1α-regulated dCas9-VP64 and control cells 6 days after transduction with sgRNAs. Scale bars=100 m.

FIG. 3A-G shows a repression of the pluripotency network by CRISPRi-mediated downregulation of OCT4A in hESCs leads to differentiation into different cell lineages. FIG. 3A shows a genomic view of the OCT4 locus indicating OCT4 isoforms A and B. sgRNA targets, and key epigenetic marks indicating the active (H3K4me3) or repressed (H3K27me3) status, and overall accessibility (Dnase I) of the gene and its surrounding genomic area are indicated. FIG. 3B shows a schematic of the inducible TRE-regulated dCas9-KRAB and OCT4 sgRNA constructs. FIG. 3C shows a phase contrast images of cells expressing unrelated, OCT4A or OCT4B sgRNA in TRE-regulated dCas9-KRAB cells after 6 days of doxycycline treatment. Morphological changes indicated by arrows. FIG. 3D shows an immunofluorescence analysis of TRE-regulated dCas9-KRAB cells expressing unrelated or OCT4A sgRNA after 6 days of doxycycline treatment for CDX2, OCT4A, NANOG, SOX17 and T. FIG. 3E shows an immunofluorescence analysis of TRE-regulated dCas9 cells expressing unrelated or OCT4A sgRNA after 6 days of doxycycline treatment for CDX2, OCT4A, NANOG, SOX17 and T. Scale bars=200 m. FIG. 3F shows a quantitative gene expression analysis of differentiation markers CDX2, T, SOX17, SOX7, and AFP in OCT4A-158 sgRNA expressing TRE-regulated dCas9-KRAB or TRE-regulated dCas9 cells over 12 days of doxycycline treatment. Data is expressed as fold over hESCs+/−SD. FIG. 3G shows a quantitative gene expression analysis of differentiation markers CDX2, T, SOX17, SOX7, and AFP in OCT4A-12 sgRNA expressing TRE-regulated dCas9-KRAB or TRE-regulated dCas9 cells over 12 days of doxycycline treatment. Data is expressed as fold over hESCs+/−SD.

FIG. 4A shows the amino acid sequences of dCas9-NLS-3×HA-VP64 (SEQ ID NO: 20), FIG. 4B shows the amino acid sequence of dCas9-NLS-3×HA-KRAB (SEQ ID NO: 21), and the nucleic acid sequence of an sgRNA cloning template (SEQ ID NO: 22) where the D10A, H840A spCas9 sequence is indicated in yellow, the SV40 NLS in cyan, the 3×HA tag in green and the effector domain in magenta. The pLKO.1 U6 promoter of the sgRNA template DNA sequence (SEQ ID NO: 22) is shown where the U6 promoter transcription start site is indicated in magenta and the constant portion of the sgRNA sequence is highlighted in yellow (Mali et al., 2013 [11]). The type IIS BfuAI recognition sites utilized for cloning annealed oligonucleotides encoding the sgRNA sequence are indicated in bold letters, where the cleavage positions on the Crick and Watson strands are respectively indicated above and below the sequence yielding 4 base pair 5' overhangs.

FIG. 5A-D shows that dCas9-E variants can be expressed in hESCs. Delivery of dCas9-E variants is detected by immunofluorescence through an internal HAtag. FIG. 5A shows an immunofluorescence analysis for HA in hESCs transduced with EF1α-regulated dCas9-VP64. FIG. 5B shows an immunofluorescence analysis for HA in hESCs transduced with EF1α-regulated dCas9-KRAB. FIG. 5C shows an immunofluorescence analysis for HA in hESCs transduced with TRE-regulated dCas9-VP64 after 48 hours with and without doxycycline treatment. FIG. 5D show an immunofluorescence analysis for HA in hESCs transduced with TRE-regulated dCas9-KRAB after 48 hours with and without doxycycline treatment. Scale bars=100 μm.

FIG. 6A-E shows the quantitation of CRISPRe-mediated, sgRNA-specific upregulation of a developmentally relevant transcription factor in hESCs. FIG. 6A shows a schematic of the inducible TRE-regulated dCas9-VP64 and SOX17 sgRNA construct. FIG. 6B shows Immunofluorescence analysis of TRE-regulated dCas9-VP64 cells transduced with a control or SOX17-177 sgRNA after 6 days of doxycycline treatment. FIG. 6C shows the percentage of cells expressing SOX17 in TRE-regulated dCas9-VP64 cells transduced with a control or SOX17-177 sgRNA after 6 days of doxycycline treatment. FIG. 6D shows an immunofluorescence analysis of TRE-regulated dCas9-VP64 cells transduced with SOX17-126, SOX17-296 or SOX17-91 sgRNA, or a combination of all four SOX17 sgRNAs after 6 days of doxycycline treatment. FIG. 6E shows the mean fluorescence intensity of SOX17- and SOX17+ populations in TRE-regulated dCas9-VP64 cell cultures transduced with SOX17-177 sgRNA or a combination of four SOX17 sgRNAs after 6 days of doxycycline treatment. The background mean fluorescence intensity of control sgRNA cultures is represented with a dotted line. The difference in mean fluorescence intensity of SOX17+ populations between single and a plurality of sgRNAs is statistically significant at p<0.01 using a Mann-Whitney test. Scale bars=100 μm.

FIG. 7A-D shows CRISPRi-mediated downregulation of OCT4A in hESCs induces morphological changes and differentiation. FIG. 7A shows phase contrast images of cells expressing control, OCT4A or OCT4B sgRNAs in control or TRE-regulated dCas9-KRAB cells after 6 days of doxycycline treatment. Morphological changes indicated by arrows. FIG. 7B shows OCT4A immunofluorescence analysis of cells expressing control, OCT4A or OCT4B sgRNAs in TRE-regulated dCas9-KRAB cells after 6 days of doxycycline treatment. Areas of cells not expressing OCT4A indicated by arrows. FIG. 7C shows an immunofluorescence analysis of TRE-regulated dCas-KRAB cells expressing OCT4B sgRNAs after 6 days of doxycycline treatment for CDX2, OCT4A, NANOG, SOX17 and T. FIG. 7D shows phase contrast images of cells expressing OCT4A or unrelated sgRNA in TRE-regulated dCas9 cells after 6 days of doxycycline treatment. Morphological changes indicated by arrows. Scale bars=200 μm.

FIG. 8A-C shows a combinatorial screening approach to identify TFs controlling transition from hESCs to DE and from DE to AFE. FIG. 8A shows a schematic overview of the cell fate programming approach. Cas9 effector-containing hES cells will be transduced with pools of sgRNAs targeting different candidate genes for activation (dspCRISPRa) or repression (dspCRISPRi). Differentiated cells will be enriched by endodermal-specific culture conditions or FACS. FIG. 8B shows histone 3 K4me2-based identification of TF with differential transcriptional states. The intensity H3K4me2 ChIP-Seq peaks around the TSS around each human TF was evaluated in hESC, DE and AFE. TF genes were hierarchically clustered and two groups (1 & 2) were identified that transition from low H3K4me2 levels in hESCs to high in AFE. FIG. 8C shows an example of sorting data that allows the recovered of specific AFE cells from differentiated population. FOXA2 expressing cells are evaluated for SOX2 and EpCAM expression. The depicted gate focuses on AFE cells (FOXA2+SOX2+EpCAM+).

FIGS. 11A-11B present exemplary data showing differentially colored dCas9 DNA constructs comprising sgRNA sequences specific for telomeric target sequences. FIG. 11A shows labeling of Sp and Nm teleomere target sequences (red and green, respectively). FIG. 11B shows labeling of Sp and SU teleomere target sequences (green and blue, respectively).

FIG. 12A illustrates human chromosome 9 regions C9-1 or C9-2 specific for the sgRNA targeting sequences. FIG. 12B shows Sp dCas9-RFP (retinal pigmented epithelium, RPE) and St1 dCas9-GFP co-expressed in diploid human cells. FIG. 12C shows the simultaneous detection of pericentromeric sequences C9-1 and C9-2.

In FIG. 13B, the data is provided showing co-labeling of C13-1 and an adjacent telomere sequence. In FIG. 13C, the data is provided showing co-labeling of C13-1 and C13-2.

FIGS. 15A-15J present exemplary data showing various ways to optimize different variations of the presently disclosed dCas9 labeling method.

FIG. 15A presents exemplary data to optimize promoter selection for CRISPR DNA labeling using Sp dCas 9-GFP.

FIG. 15B presents exemplary data to optimize fluorescence by fusion of 3×GFP to Sp dCas9.

FIG. 15C presents exemplary data to optimize SgRNA length for CRISPR labeling using sp Cas9.

FIG. 15D presents exemplary data to optimize PAM choice for CRISPR labeling using sp Cas9.

FIG. 15E presents exemplary data demonstrating suboptimal PAM for labeling CTG repeat expansion in DMPK gene.

FIG. 15F presents exemplary data to optimize Nm dCas9 localization for CRISPR labeling.

FIG. 15G presents exemplary data to optimize Nm sgRNA for CRISPR labeling using Nm Cas9.

FIG. 15H presents exemplary data to optimize PAM choice for CRISPR labeling using Nm Cas9.

FIG. 15I presents exemplary data to optimize St1 Cas9 localization for CRISPR labeling.

FIG. 15J presents exemplary data to optimize sgRNAs for CRISPR labeling using St1 Cas9.

DETAILED DESCRIPTION

Figure 9:
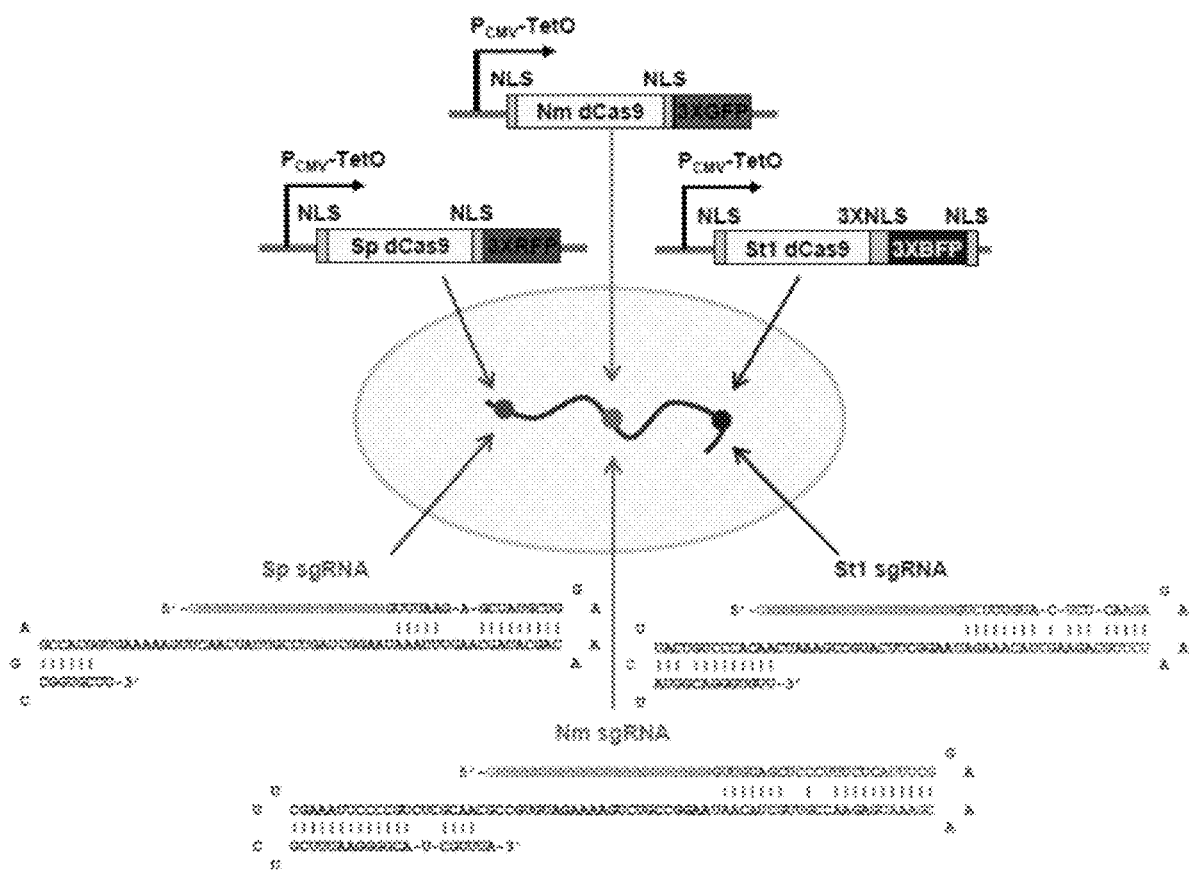
FIG. 9 present several embodiments of differentially colored DNA constructs useful for CRISPR gene labeling. Three representative DNA constructs are shown that may be coupled with either a green fluorescent protein (GFP), a red fluorescent protein (RFP), or a blue fluorescent protein (BFP). Each differently colored DNA construct originates from a different bacterial species: Sp, St1, and Nm.

The following detailed description, and the figures to which it refers, are provided for the purpose of describing and illustrating certain preferred embodiments or examples of the invention only, and no attempt has been made to exhaustively describe all possible embodiments or examples of the invention. Thus, the following detailed description and the accompanying figures shall not be construed to limit, in any way, the scope of the claims recited in this patent application and any patent(s) issuing there from.

1. Trans-Acting Factors and Cis-Regulatory Modules

The identification of the trans-acting factors and cis-regulatory modules that are involved in human pluripotent stem cell (hPSC) maintenance and differentiation is necessary to dissect the operating regulatory networks in these processes and thereby identify nodes where signal input will direct desired cell fate decisions in vitro or in vivo. To deconvolute these networks, a method to influence the differentiation state of hPSCs or multipotent stem cells with a CRISPR-associated catalytically inactive dCas9 fused to an effector domain needs to be established. Such a method is described herein. In human embryonic stem cells, it was found that the dCas9 effectors can exert positive or negative regulation on the expression of developmentally relevant genes, which can influence cell differentiation status when impinging on a key node in the regulatory network that governs the cell state. This system provides a platform for the interrogation of the underlying regulators governing specific differentiation decisions, which can then be employed to direct cellular differentiation down desired pathways.

II. Human Pluripotent Stem Cells

Human pluripotent stem cells (hPSCs) offer a unique avenue to study normal as well as defective cellular differentiation and function in vitro, and have great potential to advance understanding and treatment of diseases. However, for many cell types of interest (e.g. mature pancreatic β-cells and thymic epithelial cells), the inability to guide hPSCs toward the desired mature and functional cell types through the application of exogenous signaling molecules precludes utilization of this in vitro system in many areas. Exogenous delivery of transcription factors may provide an alternate method to influence cell identity in hPSCs and to elucidate regulatory networks underlying these cell fate decisions. Recently, an RNA-guided adaptive immune system that is widespread in bacteria and archaea (Wiedenheft et al., 2012 [1]) has been adapted for targeted DNA cleavage or gene regulation in prokaryotic and eukaryotic genomes (Charpentier and Doudna, 2013 [2]). Applied to hPSCs, such a system may provide a platform for the systematic and high-throughput identification of factors relevant to stem cell differentiation.

III. Clustered Regularly Interspaced Short Palindromic Repeat (CRISPR)

A. The CRISPR Platform

Clustered regularly interspaced short palindromic repeat (CRISPR) RNA sequences and CRISPR-associated (Cas) genes generate catalytic protein-RNA complexes that utilize the incorporated RNA to generate sequence-specific double strand breaks at a complementary DNA sequence (Bhaya et al., 2011 [3]). The Cas9 nuclease from Streptococcus pyogenes (hereafter, Cas9) can be guided to specific sites in the human genome through base-pair complementation between a 20 nucleotide guide region of an engineered single-guide RNA (sgRNA) and a genomic target sequence (Mali et al., 2013b [4]; Cho et al., 2013 [5]; Cong et al., 2013 [6]; Jinek et al., 2013 [7]). A catalytically-inactive programmable RNA-dependent DNA-binding protein (dCas9) can be generated by mutating the endonuclease domains within Cas9 (Qi et al., 2013 [8]), which can modulate transcription in bacteria or eukaryotes either directly (Qi et al., 2013 [8]; Bikard et al., 2013 [9]) or through an incorporated effector domain (Gilbert et al., 2013a [10]; Mali et al., 2013a [11]; Konermann et al., 2013 [12]; Maeder et al., 2013 [13]; Perez-Pinera et al., 2013 [14]). However, the ability of a dCas9-effector (dCas9-E) system to influence the differentiation status of stem cells has not been addressed. Herein, the ability of the CRISPR effector (CRISPRe) system to modulate gene expression in human embryonic stem cells (hESCs), using either CRISPR interference (CRISPRi) or CRISPR activation (CRISPRe) is demonstrated.

B. CRISPR Regulatory Activity

The application of CRISPRe to directly influence the differentiation status of hESCs is described, providing a platform for interrogating transcriptional regulatory networks in vitro that may underpin hPSC differentiation decisions.

The definition of regulators that promote specific differentiation state choices in human stem cell populations is of fundamental interest for both the mechanistic-based understanding of these regulatory networks and the directed generation of therapeutic cell populations for cell replacement therapies [25-27]. Transcription factors (TFs) have been identified to play a role in cell identity and have the ability to (re)program cell state [25, 28]. Although the regulators that drive some cell fate transitions are known, in the majority of instances these critical factors remain undefined. Previously, factors that guide cell identity of stem cells and mature cell types have been successfully identified using screening approaches (e.g. TF overexpression [15, 28-30] or shRNA libraries [31-35]), but to date existing tools for modifying gene expression have not been sufficiently potent to provide a general technology to achieve this goal. Consequently, there is a need for a versatile, high-throughput platform that can control the expression (up and down) of TFs to determine their effects on cells state. Artificial transcription factors could be a solution if easily programmable, as they have been employed in specific instances [36]. Recently, an RNA-guided adaptive immune system that is widespread in bacteria and archaea [1] (Cas9/CRISPR) has been engineered for targeted DNA cleavage or gene regulation in prokaryotic and eukaryotic genomes [4, 6, 8-14, 23, 37-40]. RNA-guided approaches provide the unique opportunity to use artificial transcription factors to exquisitely engineer gene expression networks in a controlled manner. Applied to human pluripotent stem cells (hPSCs), such a system could provide a platform for the systematic and high-throughput identification of factors relevant to human stem cell differentiation.

CRISPR-based defense systems are found broadly in bacterial and archaeal systems [1, 3, 41]. Type II systems employ a single protein, Cas9, to facilitate RNA-guided cleavage of a target DNA sequence complementary to the sgRNA [1, 41] and the protospacer adjacent motif (PAM) recognized by Cas9, where both elements must be recognized to achieve efficient DNA cleavage [6, 23, 42] (FIG. 1A). The Cas9 nuclease from *S. pyogenes* (hereafter, spCas9) can be targeted to a specific sequence through Watson-Crick pairing between a 20 nucleotide guide region of an engineered single-guide RNA (sgRNA) and a target sequence [4-7]. The *N. meningitidis* Cas9 (nmCas9) recognizes a larger PAM element and employs a different (orthogonal) guide RNA [24, 43, 44] (FIG. 1B).

A catalytically-inactive programmable, RNA-dependent DNA-binding protein (the nuclease-dead versions of these Cas9 variants: dspCas9 or dnmCas9) can be generated by mutating the RuvC and HNH endonuclease domains within Cas9 [8], which can modulate transcription in bacteria or eukaryotes either directly [8, 9] or through an incorporated effector domain [10-14, 24]. However, the ability of a dspCas9-effector (FIG. 1C) system to influence the differentiation status of human stem cells has not previously been addressed.

Various systems involving CRISPR-Cas systems have been described. One reference Mali, P. et al. (2013) [11] describes that prokaryotic type II CRISPR-Cas systems can be adapted to enable targeted genome modifications across a range of eukaryotes. The reference describes an engineered system to enable RNA-guided genome regulation in human cells by tethering transcriptional activation domains either directly to a nuclease-null Cas9 protein or to an aptamer-modified single guide RNA (sgRNA). Using this functionality a transcriptional activation-based assay was developed to determine the landscape of off-target binding of sgRNA:Cas9 complexes and compared it with the off-target activity of transcription activator-like (TALs) effectors. It should be noted that only activation domains were used and the cell line, HEK 293T cells, are not pluripotent stem cells. This reference does not describe a method of particular differentiation of pluripotent stem cells.

Another reference, Gilbert, et al. (2013) [10], describes that CRISPR-associated catalytically inactive dCas9 protein offers a general platform for RNA-guided DNA targeting. Here, the reference describes that fusion of dCas9 to effector domains with distinct regulatory functions enables stable and efficient transcriptional repression or activation in human and yeast cells, with the site of delivery determined solely by a coexpressed short guide (sg)RNA. The reference employs a lentiviral delivery system to introduce the elements into the cells. While describing one method to repress or activate target transcription using nuclease-deficient Cas9 with a fused effector domains in human cell lines using a lentiviral delivery system, this reference does not describe a method of particular differentiation of pluripotent stem cells.

Another reference, Maeder, et al. (2013) [13], describes that single or a plurality of gRNAs can direct dCas9 fused to a VP64 transcriptional activation domain to increase expression of endogenous human genes. This reference targeted gene transcriptional activation and repression in human cell lines and activation in *E. coli* cells. The reference results strongly suggests that multiple or a plurality of sgRNA-dCas9-VP64 complexes can function efficiently together in a single cell. While describing one method to repress target transcription using nuclease-deficient Cas9 with a fused effector domains, this reference does not describe a method of particular differentiation of pluripotent stem cells or the use of a lentiviral delivery system.

Another reference, Bikard, et al. (2013) [9], describes the use of a Cas9 nuclease mutant that retains DNA-binding activity and can be engineered as a programmable transcription repressor by preventing the binding of the RNA polymerase (RNAP) to promoter sequences or as a transcription terminator by blocking the running RNAP in bacteria. In addition, a fusion between the omega subunit of the RNAP and a Cas9 nuclease mutant directed to bind upstream promoter regions can achieve programmable transcription activation. While describing one method to repress or activate target transcription using nuclease-deficient Cas9 with a fused effector domains in bacteria, this reference does not describe a method of particular differentiation of pluripotent stem cells or the use of a lentiviral delivery system.

Another reference, Qi, et al. (2013) [8], describes catalytically dead Cas9 lacking endonuclease activity, when coexpressed with a guide RNA, generates a DNA recognition complex that can specifically interfere with transcriptional elongation, RNA polymerase binding, or transcription factor binding. This system, which is referred to as CRISPR interference (CRISPRi), can efficiently repress expression of targeted genes in *Escherichia coli*, with no detectable off-target effects. While describing one method to repress target transcription using nuclease-deficient Cas9 in bacteria with the use of a lentiviral delivery system, this reference does not describe a method of particular differentiation of pluripotent stem cells or with Cas9 fused effector domains.

Another reference, Cheng, et al. (2013) [45] describes catalytically dead Cas9 with a fused activation domain, when coexpressed with a guide RNA, generates a DNA recognition complex that can specifically activate transcriptional elongation of genes, but that 3 to 4 sgRNAs are required for robust activity. This system, which is referred to as CRISPR-on, was used to activate genes in mouse embryonic stem cells (mESCs), HeLa cells and mouse zygotes. While describing one method to activate target transcription using nuclease-deficient Cas9, this reference does not describe a method of particular differentiation of pluripotent stem cells. Another reference, Mali, et al. (2013) [4], describes that the CRISPR targeting process relies on CRISPR components; is sequence-specific; and, upon simultaneous introduction of a plurality of custom guide RNA (gRNAs), can effect multiplex editing of target loci. The reference describes engineering the type II bacterial CRISPR system to function with custom (gRNA) in human cells. For the endogenous AAVS1 locus, targeting rates of 10 to 25% in 293T cells was obtained, 13 to 8% in K562 cells, and 2 to 4% in induced pluripotent stem cells. The reference describes the results as establishing an RNA-guided editing tool for facile, robust, and multiplexable human genome engineering. This reference does not describe a method of particular differentiation of pluripotent stem cells or a nuclease-deficient Cas9 with a fused effector domain.

Another reference, Ran, et al. (2013) [37], describes an approach that combines a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The reference describes that using paired nicking can reduce off-target activity by 50- to 1,500-fold in cell lines and to facilitate gene knockout in mouse zygotes without sacrificing on-target cleavage efficiency. The reference speculates that the versatile strategy enables a wide variety of genome editing applications that require high specificity. This reference does not describe a method of particular differentiation of pluripotent stem cells or a nuclease-deficient Cas9 with a fused effector domain. Another reference, Hou, et al. (2013) [43], describes the use of a CRISPR-Cas system from *Neisseria meningitides* to demonstrate efficient targeting of an endogenous gene in three hPSC lines using homology-directed repair (HDR). The Cas9 RNA-guided endonuclease from *N. meningitidis* (NmCas9) recognizes a 5'-NNNNGATT-3' protospacer adjacent motif (PAM) different from those recognized by Cas9 proteins from *S. pyogenes* and *S. thermophilus* (SpCas9 and StCas9, respectively). Similar to SpCas9, NmCas9 is able to use a single-guide RNA (sgRNA) to direct its activity. Because of its distinct protospacer adjacent motif, the *N. meningitidis* CRISPR-Cas machinery increases the sequence contexts amenable to RNA-directed genome editing. This reference does not describe a method of particular differentiation of pluripotent stem cells using a nuclease-deficient Cas9 with a fused effector domain, but rather describes genome editing.

Another reference, Larson, M. H. et al. (2013) [46], describes a "CRISPRi system" derived from the *Streptococcus pyogenes* CRISPR pathway, requiring only the coexpression of a catalytically inactive Cas9 protein (lacking nuclease activity) and a customizable single guide RNA (sgRNA). The Cas9-sgRNA complex binds to DNA elements complementary to the sgRNA and causes a steric block that halts transcript elongation by RNA polymerase, resulting in the repression of the target gene. While describing one method to repress target transcription, this reference does not describe a method of particular differentiation of pluripotent stem cells using a nuclease-deficient Cas9 with a fused effector domain.

IV. Lentiviral Delivery-Based dCas9-E/CRISPRe Transcription Effector System

A lentiviral delivery-based dCas9-E/CRISPRe transcription effector system for application in hESCs was created by generating a human codon optimized, catalytically inactive version of Cas9 (dCas9) (Jinek et al., 2012; Qi et al., 2013 [8]), which is fused to either a VP16 tetramer activation domain (VP64) or a Krüppel-associated box (KRAB) repressor domain (dCas9-E) (FIG. 3 and FIG. 4). Following lentiviral infection of hESCs, constitutive or doxycycline-inducible expression of dCas9-E was confirmed under the control of EF1α or tetracycline-responsive (TRE) promoters, respectively (FIG. 5).

A separate U6 promoter-based lentiviral delivery system for sgRNA expression was generated to program dCas9-E for specific genomic targets (Jinek et al., 2012 [23]). The ability of the dCas9-VP64 system to be employed to activate a developmentally relevant gene in hESCs was tested. SOX17 is a gene linked to differentiation of definitive endoderm (Kanai-Azuma et al., 2002 [47]) that is repressed in hESCs and exhibits a classical bivalent H3K4me3 activation and an H3K27me3 repression epigenetic mark of a poised gene (Rada-Iglesias et al., 2011 [48])(FIG. 2A). This regulator offers a unique opportunity to address whether a critical differentiation marker in a poised state could be activated. To assess the ability of dCas9-VP64 to upregulate expression of SOX17 in hESCs, dCas9-VP64 in hESCs was expressed under control of the ubiquitously expressed EF1α promoter and designed two sgRNAs to target regions upstream of the SOX17 transcriptional start site (TSS) (FIG. 2A and FIG. 2B). Neither expression of the dCas9-VP64 variant alone nor the presence of SOX17-specific sgRNAs alone led to significant increases in SOX17 expression levels. Likewise, delivery of dCas9-VP64 in conjunction with the SOX17-126 sgRNA had no detectable effect. In contrast, co-delivery of dCas9-VP64 and SOX17-177 sgRNA increased expression of SOX17 by 287(+/−35)-fold (FIG. 2C). This increase in gene expression was sufficient to allow the accumulation of SOX17 protein in the treated hESC cultures based on immunofluorescence analysis (FIG. 2D). Thus, despite the presence of repressive epigenetic marks, the CRISPRe system can drive expression of developmentally relevant genes in hESCs with one sgRNA.

To ascertain the number of hESCs responding to the CRISPRe system, SOX17-177 sgRNA or a control sgRNA was delivered into TRE-regulated dCas9-VP64 cells (FIG. 6A). In this system selection of the cells with neomycin and puromycin enables the combined enrichment of TRE-regulated dCas9-VP64 and each sgRNA. Combined selection was followed by 6 days of doxycycline treatment, resulting in 25.4% of cells with antibody detectable SOX17 expression compared to 0% of control cells (FIG. 6B and FIG. 6C). This variability may be due to variations in the expression levels of CRISPRe components due to the location of viral integration or subsequent silencing of the viral constructs. Variation in the underlying epigenetic state of each cell may also contribute to its overall responsiveness to the CRISPRe system.

The ability of an sgRNA to mediate dCas9-VP64-based changes in gene expression in hESCs is consistent with studies of similar dCas9 activators in transformed human cell lines (Cheng et al., 2013 [45]; Mali et al., 2013a [11]; Maeder et al., 2013 [13]; Gilbert et al., 2013a [10]; Perez-Pinera et al., 2013 [14]). However, in these studies co-expression of a plurality of sgRNAs is typically required for efficient gene activation (Cheng et al., 2013 [45]; Gilbert et al., 2013a [10]; Mali et al., 2013a [11]; Perez-Pinera et al., 2013 [14]). To determine whether a combination of sgRNAs would further increase SOX17 expression through CRISPRe in hESCs, cells with SOX17-177, SOX17-126, SOX17-296, or SOX17-91 sgRNAs were transduced individually or in combination. A combination of all SOX17 sgRNAs increased SOX17 protein-specific immunoreactivity in a subset of cells when compared to individual sgRNAs (FIG. 6B and FIG. 6D). Quantitation of expression levels in the SOX17+ populations revealed a statistically significant increase ($p<0.01$) in the mean expression level of SOX17 when a plurality of sgRNAs were employed, consistent with an additive effect between different sgRNAs targeting the same promoter (FIG. 6E). While not limiting the current invention, it is possible that while a specific sgRNA suffices to increase gene expression in hESCs, a plurality of sgRNAs can further improve expression levels of a target gene.

V. Cell Reprogramming with CRISPR

While the imposed activity of specific transcription factors has proven effective in the programming of cell fate decisions (reviewed in (Ladewig et al., 2013 [49])), the destabilization of transcription factors that govern cell identity can also be used to change cell differentiation status (e.g. (Cobaleda et al., 2007 [50]; Hay et al., 2004 [51])).

To address whether the dCas9-E system can be harnessed for this purpose in hESCs, the pluripotency network was targeted by combining the dCas9-KRAB transcriptional repressor with OCT4 targeting sgRNAs. Two isoforms of OCT4 (also known as POU5F1) are expressed in hESCs, where isoform A is important for maintaining pluripotency while isoform B does not activate transcription of OCT4-dependent promoters (Lee et al., 2006 [52]). sgRNAs were designed to target the TSS of either OCT4 isoform A or isoform B (FIG. 3A and FIG. 3B). 6 days after co-expression of dCas9-KRAB and individual sgRNAs, a more flattened morphology was observed of cultures that contained OCT4A-specific sgRNAs when compared to hESCs that received OCT4B-specific sgRNAs (FIG. 3C and FIG. 7A). In addition, a large number of OCT4 negative cells are present in the cultures that received OCT4A-specific sgRNAs (FIG. 7B) indicating the desired silencing of this locus.

To address whether dCas9-KRAB mediated repression of a pluripotency associated gene is sufficient to influence hESC differentiation status, the dCas9-KRAB cultures were analyzed at day 6 after sgRNA delivery for expression of the pluripotency factor NANOG, as well as for differentiation markers for trophectoderm (CDX2), endoderm (SOX17), and mesendoderm/mesoderm (T). While virtually every cell in the dCas9-KRAB cultures with a control sgRNA expressed both OCT4 and NANOG, large areas of OCT4 and NANOG-negative cells were observed with OCT4A-specific sgRNAs (FIG. 3D and FIG. 7C). The expression of the dCas9-KRAB variant with a control sgRNA did not influence OCT4 expression or colony morphology, suggesting the possibility that the dCas9-E/CRISPRe components are not negatively influencing self-renewal independent of their gene-specific targeting function. While not limiting the current invention, it is possible that the dCas9-E/CRISPRe system is able to influence hESC differentiation with one sgRNA.

Recently, it was reported that a CRISPRi system can be implemented by sterically interfering with RNA Polymerase II transcriptional initiation or elongation via dCas9 binding (Qi et al., 2013 [8]; Gilbert et al., 2013b [10]). To address whether the observed effects of dCas9-KRAB on hESCs in this system were due to an obstruction mechanism rather than KRAB-mediated repression, the impact of a dCas9 variant lacking the KRAB effector domain was tested on OCT4 expression. No morphological changes were observed in hESC cultures co-expressing dCas9 and the OCT4A sgRNA targeting the −158 region upstream of the TSS (FIG. 7D). Interestingly, rare cells with morphological changes in the cultures co-expressing dCas9 and the OCT4A sgRNA proximal to the TSS were found (OCT4A-12, FIG. 7D). To address whether the morphological changes were accompanied by a change in expression of pluripotency genes or differentiation-associated factors, the cultures were analyzed for the presence of OCT4 and NANOG or CDX2, SOX17 and T, respectively. In concordance with the subtle morphological changes, patches of OCT4 and NANOG downregulation were observed in hESC dCas9 cultures containing the OCT4A-12 sgRNA, but not in cultures containing the OCT4A-158 sgRNA (FIG. 3E). In addition, SOX17 antibody reactive cells were detected within the NANOG downregulated regions of the dCas9/OCT4A-12 sgRNA treated cultures. Overall, the impact of the effectorless dCas9 on differentiation-associated genes is attenuated relative to dCas9-KRAB. Thus, some degree of repression associated with the dCas9-KRAB/OCT4A-12 sgRNA combination is likely due to direct interference of dCas9 with the function of RNA Polymerase II, whereas the repression associated with the dCas9-KRAB/OCT4A-158 sgRNA combination is dependent on the KRAB effector domain.

To address whether the effector-independent dCas9 might impose a delayed effect on differentiation relative to the dCas9-KRAB effector, the appearance of differentiation-associated transcripts was analyzed in a time course for both versions of dCas9 (FIG. 3F and FIG. 3G). No significant increases in CDX2, T, SOX17, SOX7 or AFP transcripts were detected in dCas9/OCT4A sgRNA treated cultures over the course of 12 days. In contrast, dCas9-KRAB/OCT4A-158 sgRNA treated cultures showed increases in CDX2, SOX17 and T starting at day 3, in SOX7 at day 6 and in AFP at day 12 consistent with the differentiation of a fraction of the treated cells down various developmental pathways. Cells treated with dCas9-KRAB/OCT4A-12 sgRNA displayed similar expression of differentiation markers (FIG. 3G). These examples could be considered as a proof-of-principle study demonstrating the potency of dCas9-E/CRISPRe for the activation or repression of key transcription factors in hPSCs that can have dramatic effects on gene expression and differentiation status. It is possible that this approach may have wide applicability in altering gene expression to modulate cell fate decisions in various stem cell populations. These experiments may be performed in a directed manner, or using library-based lentiviral approaches similar to those employed with shRNA libraries (Moffat et al., 2006 [32]; Kagey et al., 2010 [53]). It is possible that this system may be instrumental in dissecting regulatory networks in hPSC derivatives and thereby understanding their contribution to development or disease.

VI. Multi-Color CRISPR DNA Constructs

The intra-nuclear location of genomic loci and their dynamics play a role in understanding the spatial and temporal regulation of gene expression. Recently it has proven possible to visualize endogeneous genomic loci in live cells by the use of transcription activator-like effectors (TALEs) as well as modified versions of the bacterial immunity CRISPR/Cas9 system. The data presented herein validate a design of multicolor versions of CRISPR using catalytically inactive Cas9 endonuclease (dCas9) from three bacterial orthologs. Each pair of dCas9-fluorescent proteins and cognate sgRNAs efficiently labeled several target loci in live human cells. Using pairs of differently colored dCas9-sgRNAs, it was possible to determine the intra-nuclear distance between loci on different chromosomes. In addition, the fluorescence spatial resolution between two loci on the same chromosome could be determined and related to the linear distance between them on the chromosome's physical map, thus permitting an assessment of the DNA compaction of such regions in a live cell.

Transcription activator-like effector (TALEs) technology comprise DNA-binding proteins conjugated with fluorescent proteins to label specific chromosomal loci in living cells. Pederson T (2014) Repeated TALEs: visualizing DNA sequence localization and chromosome dynamics in live cells. Nucleus 5(1):28-31. A bacterial immunity CRISPR/Cas9 system was repurposed for gene editing in eukaryotic cells, in which programmable DNA recognition and cleavage of targeted loci has been enabled by employing Cas9 nuclease in collaboration with target gene-customized single-guide RNAs (sgRNAs). Cong L, et al. (2013) Multiplex genome engineering using CRISPR/Cas9 systems. Science 339(6121): 819-823; Mali P, et al. (2013) RNA-guided human genome engineering via Cas9. Science 339 (6121):823-826; Hwang W Y, et al. (2013) Efficient genome editing in zebrafish using a CRISPR/Cas system. Nat. Biotechnol. 31(3): 227-229; Cho S W, Kim S, Kim J M, Kim J-S (2013) Targeted genome engineering in human cells with the Cas9 RNA-guided endonuclease. Nat. Biotechnol. 31(3): 230-232; and Wang H, et al. (2013) One-step generation of mice carrying mutations in multiple genes by CRISPR/Cas-mediated genome engineering. Cell 153(4): 910-918.

In parallel with its deployment for gene editing, the CRISPR/Cas9 system was also utilized for sequence-specific gene regulation using nuclease-inactive Cas9 (dCas9), with this version of Cas9 subsequently applied to the visualization of genomic loci in live cells through fusion with a fluorescent protein. Qi L S, et al. (2013) Repurposing CRISPR as an RNA-guided platform for sequence-specific control of gene expression. Cell 152(5):1173-1183; Chen B, et al. (2013) Dynamic imaging of genomic loci in living human cells by an optimized CRISPR/Cas system. Cell 155(7):1479-1491; and Anton T, Bultmann S, Leonhardt H, Markaki Y (2014) Visualization of specific DNA sequences in living mouse embryonic stem cells with a programmable fluorescent CRISPR/Cas system. Nucleus 5(2):163-172. However, resolving different inter- or intra-chromosomal loci within the nucleus with CRISPR technology has remained challenging because of the need for dual labels. In one embodiment, the present invention contemplates a multicolor CRISPR system to specifically and differentially label various pairs of chromosomal loci simultaneously, allowing the distances between to be estimated in living human cells.

CRISPR technology can be used to edit specifically targeted DNA in an organism or cell. In one embodiment, the present invention contemplates a method by which defined DNA loci in the human genome can be fluorescently labeled in live cells. In one embodiment, each of the 23 chromosomes in the human karyotype have been specifically labeled in vivo. In one embodiment, genomic loci in live cells are fluorescently labeled. In one embodiment, genomic loci in live cells are edited and verified by fluorescent labeling. Although it is not necessary to understand the mechanism of an invention, it is believed that both gene labeling and gene editing may be performed concurrently, in a tandem pair of assays. It is believed that this approach offers a very high sampling capacity and fast throughput and provides an efficient basis for optimizing CRISPR editing of a particular DNA sequence on a single cell by cell basis.

The labeling of specific genomic loci in live cells is an emerging field. In some embodiments, the present invention makes improvements to, and integrates, components of the TALE and CRISPR technologies. This improved method has an advantage of being capable of detecting two different genomic loci in the same cell by virtue of the dual color versions of dCas9 or Cas9. In one embodiment, the present invention contemplates a bioinformatics-derived dataset of repeated DNA sequences in each of the human chromosomes. This dataset facilitates the identification of nucleic acid repeat sequences which are represented in a given chromosome as a much longer tract than in the other chromosomes, thus providing potential targets for the selective fluorescent labeling method as disclosed herein. For example, the present invention may utilize any one of a number of repetitive tandem repeat sequences. See, Table 1.

TABLE 1

Exemplary Types Of CRISPR Tandem Repetitive Targets

| Genomic Location | Repeat Sequence Template |
| --- | --- |
| Telomeres[a] | TTAGGG |
| Pericentromeric[b] (Satellite II/III) | ATTCC |
| Expansions[c] | CTG; GGGGCC |
| Subtelomeric/Acrocentric[d] (chromosome specific) | 10-100 base pairs |

Figure 20:
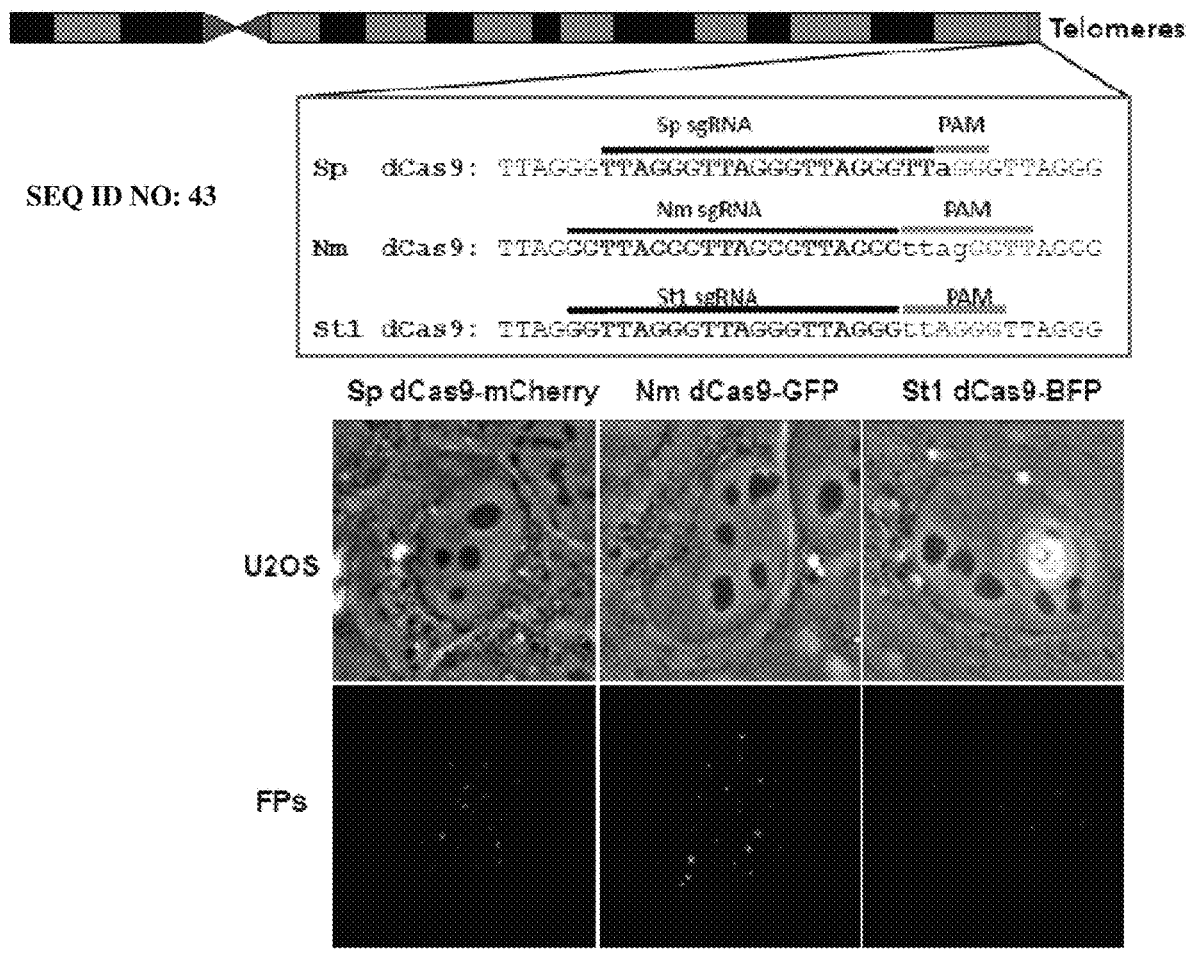
FIG. 20 presents exemplary data showing multicolor CRISPR-dCas9 binding to Sp, Nm and SU telomeric DNA target sequences.
Figure 21:
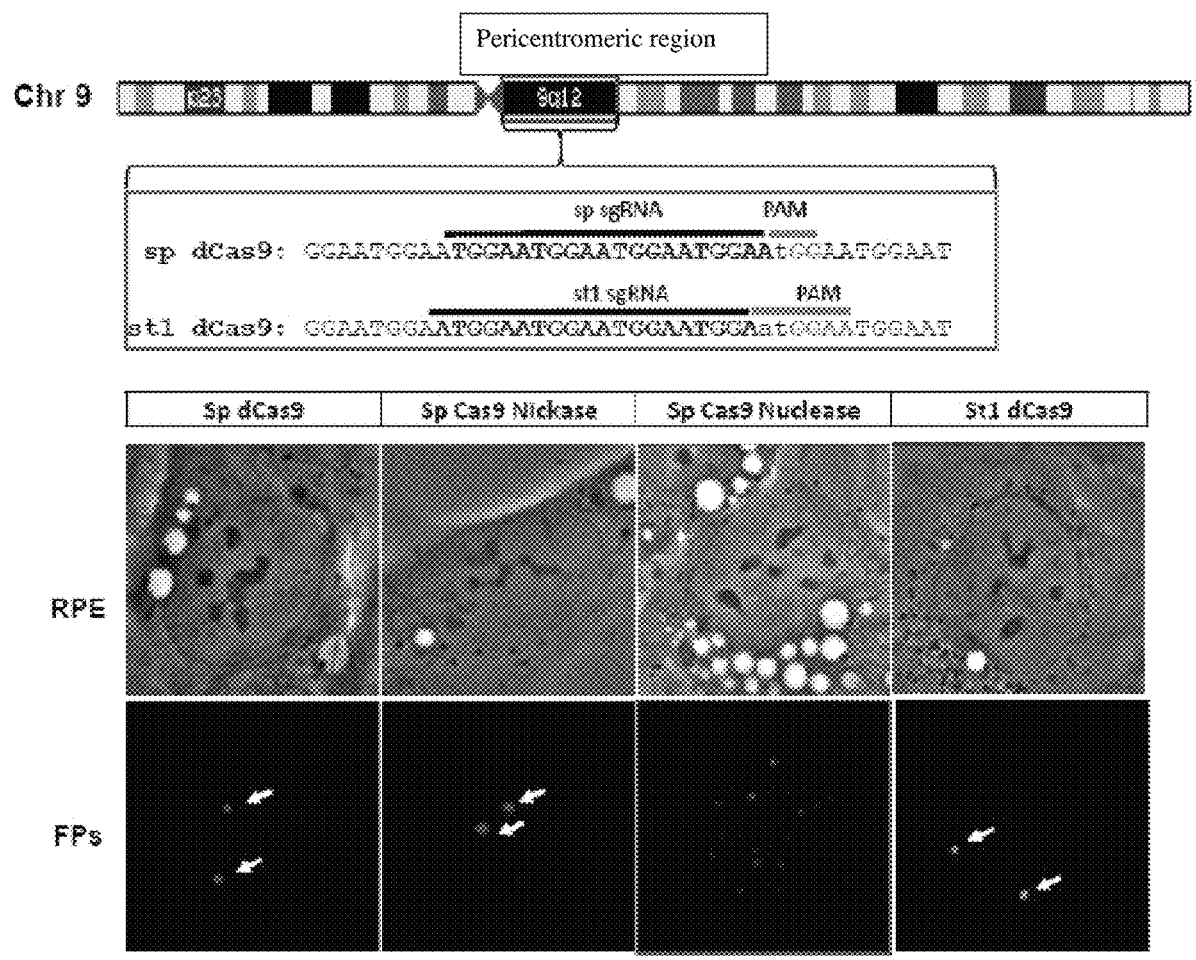
FIG. 21 presents exemplary data showing multicolor CRISPR-dCas9 binding to Sp and St1 pericentromeric DNA target sequences.
Figure 22:
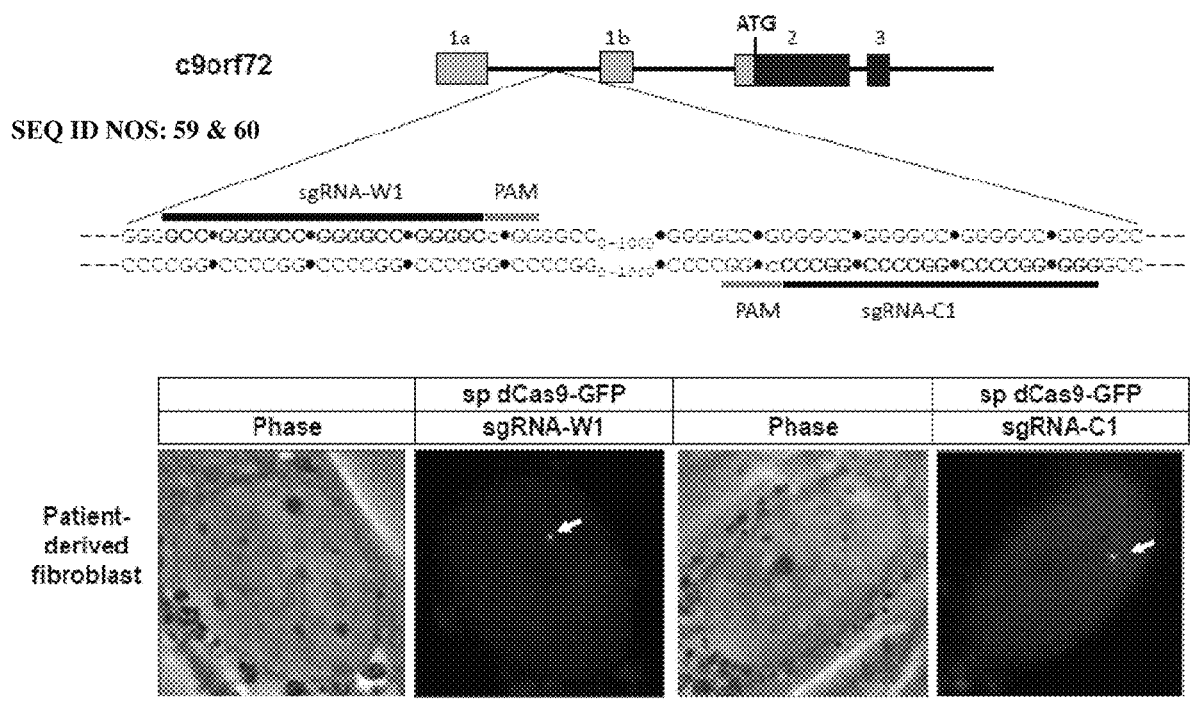
FIG. 22 presents exemplary data showing multicolor CRISPR-dCas9 binding to an Sp GGGGCC expansion DNA target sequence.
Figure 23:
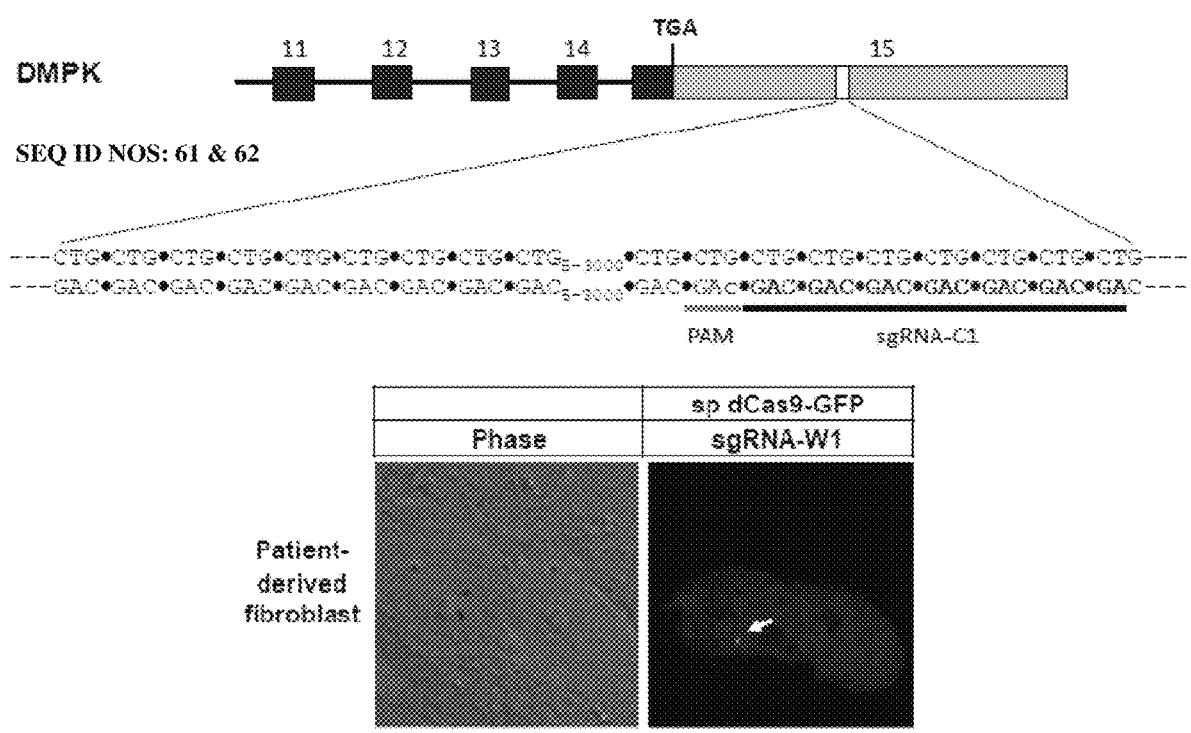
FIG. 23 presents exemplary data showing multicolor CRISPR-dCas9 binding to an Sp CTG expansion DNA target sequence.
Figure 24:
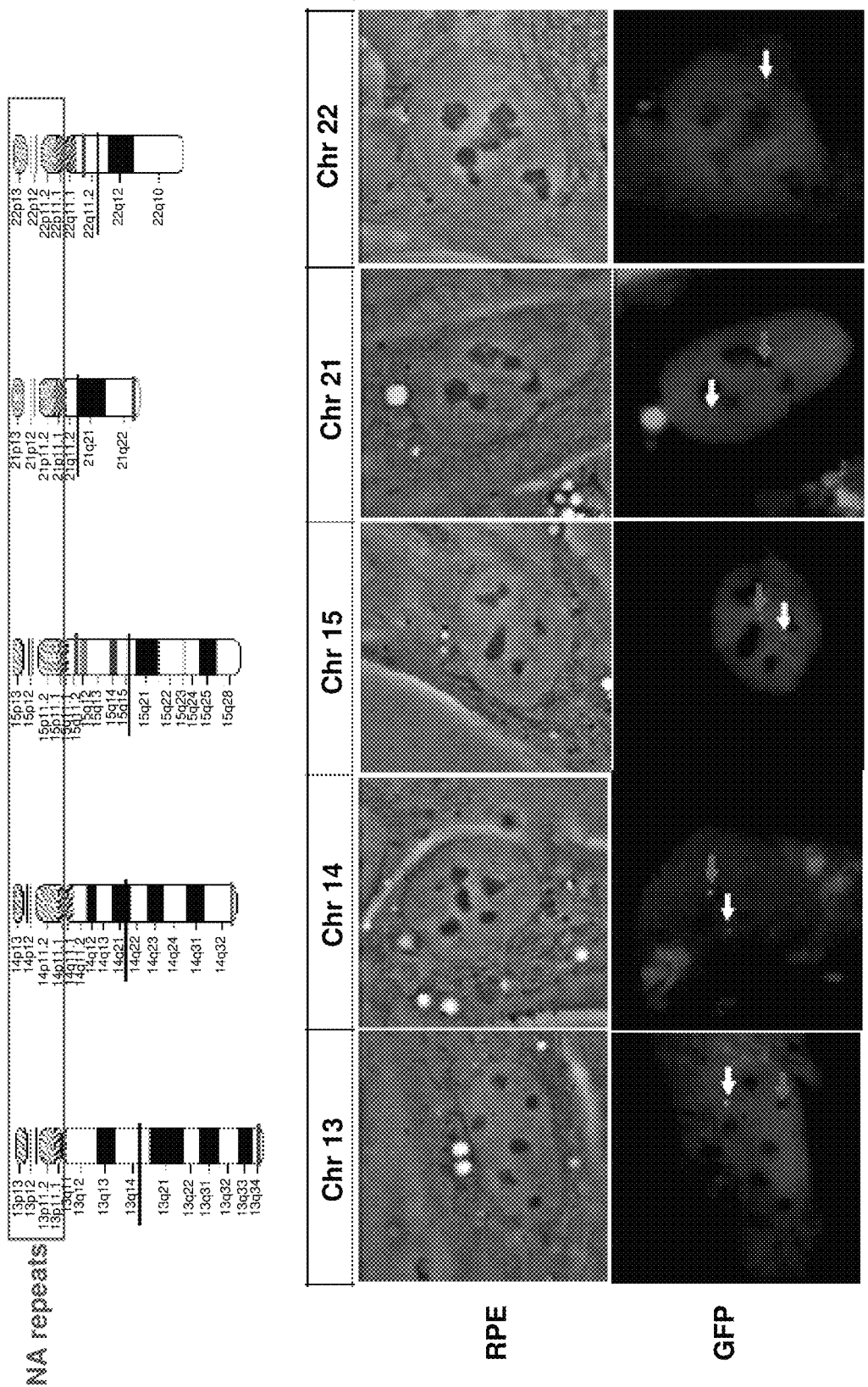
FIG. 24 presents exemplary data showing multicolor CRISPR-dCas9 binding to chromosome specific acrocentric DNA target sequences in chromosome 13, chromosome 14, chromosome 16, chromosome 21, and chromosome 22.

[a]FIG. 20;
[b]FIG. 21;
[c]FIGS. 22 & 23;
[d]FIG. 24.

In some embodiments, the present invention contemplates a method that is "switchable" that allows, for example, a very rapid analysis by Fluorescence Activated Cell Sorting (FACS) of cell samples that have been either labeled or edited. Conventionally, an assessment of whether or not a particular CRISPR-based DNA editing event has occurred or not requires a molecular analysis of DNA samples by RT-PCR, Southern blots and/or other time-consuming methods. Moreover, these conventional assessment methods are conducted on DNA isolated from entire populations of cells. In contrast, the presently disclosed "switchable" assessment methods offer several advantages. For example, a DNA labeling/editing assessment method comprising a CRISPR/TALE probe is much faster than the aforementioned methods of RT-PCR, Southern blots etc. In the present methods, cells that are analyzed by fluorescence microscopy are also compatible with FACS. In that mode, information on the extent of DNA sequence editing would be available on each and every cell and within minutes after collecting the cells. The large cell sample capacity, the fast turnaround time and the FACS sensitivity would provide a very efficient way to optimize CRISPR-based gene editing in any research program.

While genomic labeling with a single color is possible with the Sp dCas9 system, multiple orthogonal labels, which have not been previously described, was necessary to determine the relative position and movement of pairs of loci during cellular processes of interest. To address these needs, the present invention provides compositions and methods for genomic labeling and editing using orthogonal Cas9 variants from three bacterial species; *S. pyogenes, N. meningitidis* (Nm) and *S. thermophilus* (St1) which have been used for editing and gene regulation in human cells without cross-talk in cognate sgRNA binding. Esvelt K M, et al. Orthogonal Cas9 proteins for RNA-guided gene regulation and editing. Nat. Methods 10(11): 1116-1121. See, Table 2.

TABLE 2

Cas9 Orthologs For Multicolor Detection By CRISPR-FPs

| Cas9 Bacterial Source | Target DNA Sequence Size | sgRNA Source | PAM Sequences |
| --- | --- | --- | --- |
| S. pyogenese (Sp Cas9) | 9-20 mers | Sp sgRNA | NGG NAG NGT |

TABLE 2-continued

Cas9 Orthologs For Multicolor Detection By CRISPR-FPs

| Cas9 Bacterial Source | Target DNA Sequence Size | sgRNA Source | PAM Sequences |
|---|---|---|---|
| N. meningitidis (Nm Cas9) | 20-24 mers | Nm sgRNA | NNNNGATT NNNNGGTT NNNNGCTT |
| S. thermophilus (St Cas9) | 20 mers | St1 sgRNA | NNAGAAW NNGGAAW NNAGGAW NNAGGGW |

Figure 19:
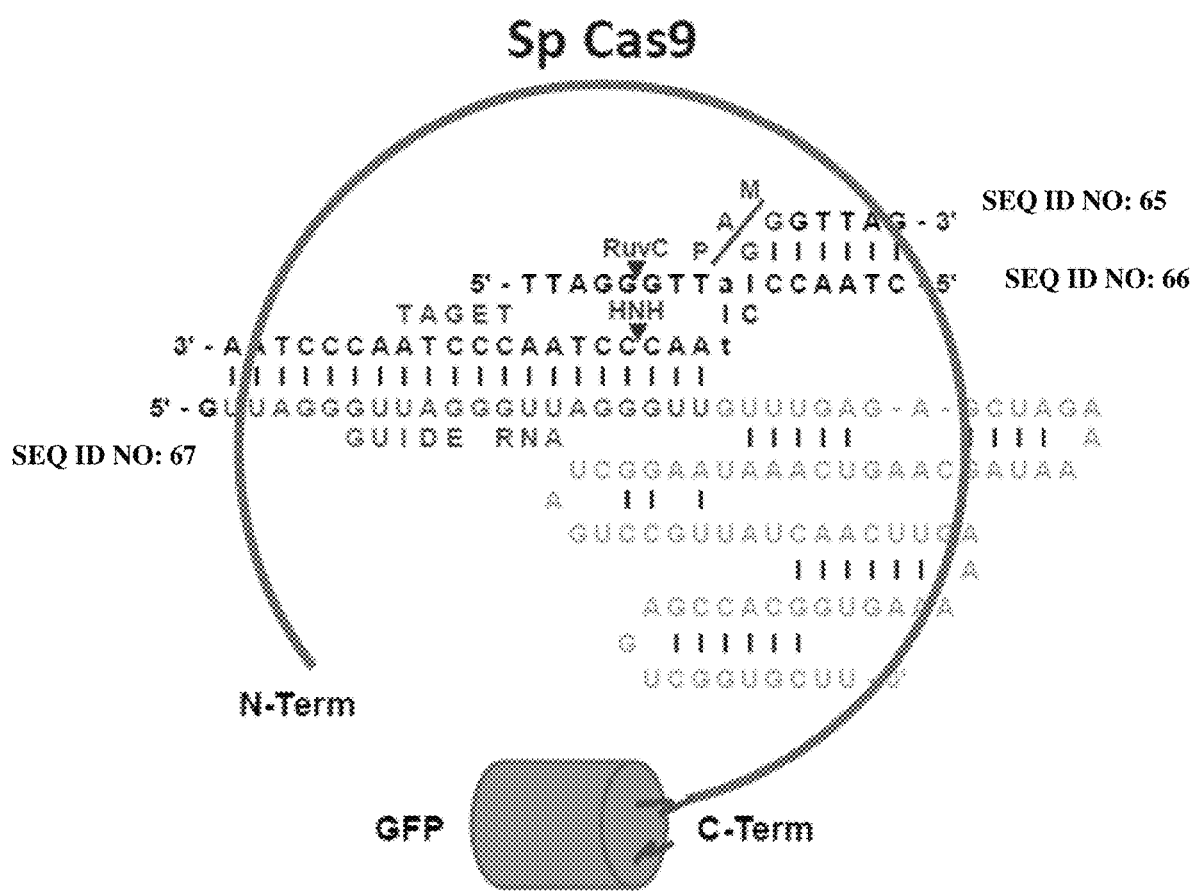
FIG. 19 illustrates one embodiment of an S. pyogenes Sp dCas9 binding configuration comprising a 20 mer target DNA sequence, an Sp sgRNA sequence and an NGG PAM sequence.

In one embodiment, a binding configuration of an *S. pyogenes* Cas9 comprises a 20 mer target DNA sequence, an Sp sgRNA sequence and an NGG PAM sequence. FIG. 19.

A. dCas9 DNA Constructs for Gene Labeling

In one embodiment, the present invention contemplates a DNA construct comprising a plurality of differentially colored labels. Each of the dCas9 DNA constructs comprise a catalytically inactive form. This advantage allows accurate live cell labeling of genomic loci because there is no nuclease activity towards the targeted DNA sequence, i.e. the construct binding is stable.

These dCas9 DNA constructs may contain a cytomegalovirus (CMV) promoter under the control of a tetracycline inducible element (TetO), a nuclear localization signal (NLS), any one of three or more dCas9s (d for "dead", i.e. a cataytically-inactive form), an additional NLS element(s), and one of three fluorescent proteins (green: GFP; red: RFP; blue: BFP). Each of the dCas9 probes is from a different species of bacteria and uses distinct small guide RNAs (sgRNAs) and PAM sequences which determine the specificity of DNA targeting as exemplified by the shown sgRNAs from each of the orthologous Cas9s and their DNA targets. See, FIG. 9. Catalytically-inactive forms of the Cas9 endonuclease (dCas9) from three bacterial species fused to Green, Red or Blue Fluorescent Protein were expressed from tetracycline regulated plasmids and sgRNAs cognate with each Cas9 ortholog were designed for the human telomere DNA repeat and expressed with U6 promoters. These compositions also comprise sgRNA as well as the vicinal PAM elements essential for Cas9 recognition of the telomeric repeat.

Figure 10:
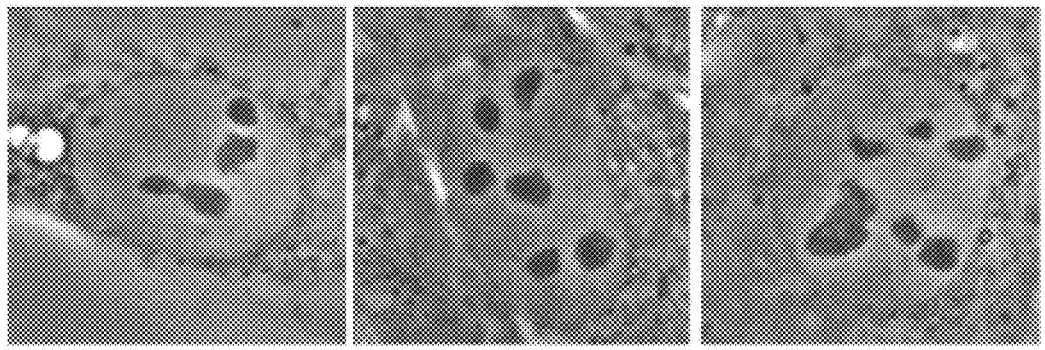
FIG. 10 presents exemplary data of Sp, St1 and Nm dCas9 DNA construct binding to their representative sgRNA targets.

One specific advantage of the present embodiments is the identification and use of Nm and St1 sgRNAs instead of being limited to the conventionally used Sp sgRNAs as is commonly known to one of ordinary skill in the art. Exemplary labeling of these three specific DNA sequences in live U2OS (human osteosarcoma cells) with each of the three dCas9:sgRNA systems. FIG. 10. Here, the labeling of telomeres using the three Cas9 orthologs, Sp, Nm and St1, fused to RFP, GFP and BFP respectively is shown along with their cognate sgRNAs. Numerous discrete fluorescent foci were observed in interphase U2OS cells with each pair of dCas9-FPs and sgRNAs.

In specific embodiments, each of the three differentially colored dCas9 DNA constructs were constructed with sgRNAs that target a human telomere DNA sequence. sgRNA telomere target sequence labeling was demonstrated using the Sp dCas9 and Nm dCas9 DNA constructs. FIG. 11A (red and green, respectively). SgRNA telomere target sequence labeling was demonstrated using the Sp dCas9 and St1 dCas9 DNA constructs. FIG. 11B (green and blue, respectively). The data presented identical patterns of discrete nuclear foci with the two colors displaying complete spatial coincidence, indicating that both Sp dCas9 and Nm dCas9 can find and co-occupy a given telomere. Similar results were obtained by co-expression of Sp dCas9-3×GFP and SU dCas9-3×BFP in conjunction with their cognate sgRNAs. These results also indicate that the expression levels of the two orthogonal systems are sufficiently similar that neither is at such vast excess that it saturates a given telomeric repeat.

Figure 12A:
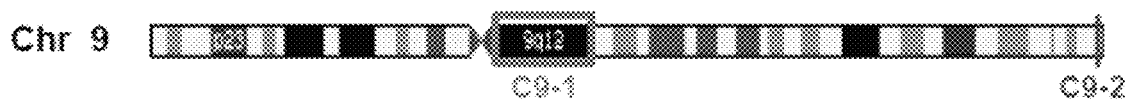
FIGS. 12A-12C present exemplary data showing differentially colored dCas9 DNA constructs specifically targeting a pericentromeric sequence.
Figure 12B:
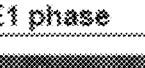
Figure 12C:
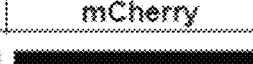

Further, in alternative embodiments, the method simultaneous detects at least two genomic loci in the same, living cell. For example, Sp dCas9-RFP (retinal pigmented epithelium. RPE) and St1 dCas9-GFP were co-expressed in diploid human cells each comprising the same sgRNA specifically targeting a pericentromeric sequence on human chromosome 9 (e.g., for example, C9-1 or C9-2). FIGS. 12A and 12B. The method was adapted for simultaneous detection of two different DNA sequences on chromosome 9, the pericentromeric sequence C9-1 and the subtelomeric sequence C9-2 (see diagram at top of figure). FIG. 12C. Each sgRNA was specifically designed for these repeats and were expressed in U2OS cells or diploid RPE1 cells together with dual color pairs of dCas9/sgRNA. The data shows the labeling of C9-1 with Sp or St1 dCas9 orthologs with cognate sgRNAs in RPE1 cells, a diploid human cell line. Two specific foci were observed with each pair of dCas9-FPs and sgRNAs indicating that these cells are in Gl. Proximity of two inter-chromosomal loci C9-1 and C13-1 in the same nucleus was also addressed. Two copies of each chromosomal locus were detected as a pair of foci and each pair was clearly quite far apart from the other in the 3-D nuclear volume as regards this inter-chromosomal situation. Intra-chromosomal propinquity of C9-1 and C9-2 was revealed to be approximately 2 μm apart. This cytological distance corresponds to a known distance of 75 Mbp between these two loci on the physical map of chromosome 9.

Figure 13A:
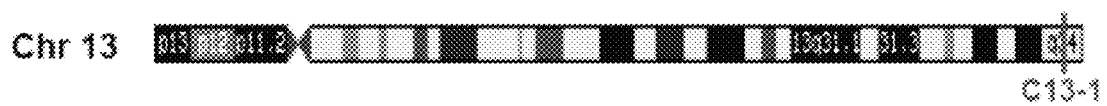
FIGS. 13A and 13B present exemplary data showing the simultaneous detection of two different DNA sequences located on different chromosomes, for example C9-1 on chromosome 9 (see FIG. 12A) and C13-1 on chromosome 13.
Figure 13B:
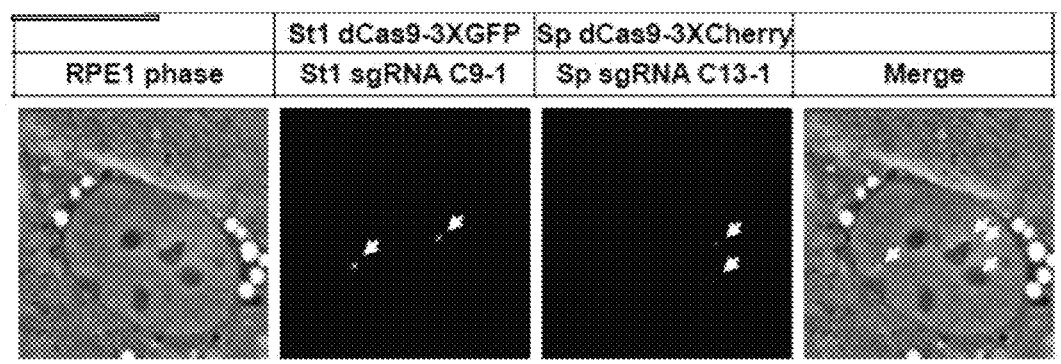

In one embodiment, the presently disclosed method detects an even greater degree of inter-locus resolution on a chromosome demonstrated by using two sites that are even more closely situated than the pair that was interrogated above. FIG. 12. Consequently, the method was adapted for simultaneous detection of two DNA sequences located on different chromosomes, C9-1 on chromosome 9 and a subtelormeric sequence located on chromosome 13, C13-1. See, FIGS. 13A and 13B. The location of the aforementioned repeat C13-1 is shown in relation to the telomere of the long arm of this chromosome, constituting a distance of 2 Mbp on the physical map in contrast to the 75 Mbp distance between the loci examined above. FIG. 12. A dual color pair of dCas9 and cognate sgRNAs were expressed targeting this latter pair of loci where two very proximal foci were observed. FIG. 13A. These data indicate that this labeling method reports intra-chromosomal distances in live cells that are compatible with the chromosome's physical map. To seek further corroboration of this, two repeats were targeted that lie yet even closer to one another in the subtelomeric region of the long arm of chromosome 13, viz. the aforementioned C13-1 and a vicinal repeat, C13-2, which lie 1.9 Mbp apart. FIG. 12B. Here, an extremely close proximity of the two signals was observed with a striking overlapping zone at the interface (see yellow zone in "Merge"). This suggests that the dual-color CRISPR method we have developed has a cytological resolution that corresponds to about 34 μm (0.1 Mbp).

The spatial resolution of the green and red foci image data provide an estimate of the 3-D configuration (e.g., interchromosomal distance) of the long arm of chromosome 9 in a live cell nucleus (FIG. 12B), a estimate of the distances between the two copies of chromosome 9 (FIG. 12C) and the two copies of chromosome 13 (FIG. 13B), as well as the distances among all four of the chromosomes when the data is cross analyzed.

Figure 14A:
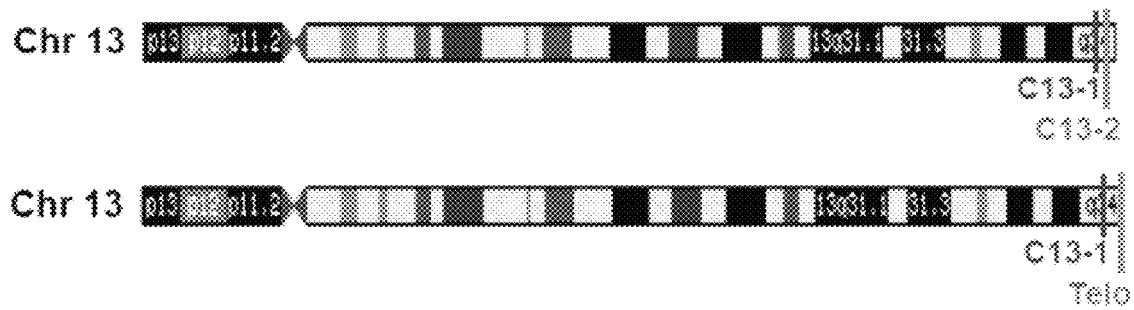
FIGS. 14A-C present exemplary data showing labeling of two spatially proximate C13-1 and C13-2 regions and/or an adjacent telomeric sequence. See, FIG. 13A.
Figure 14B:
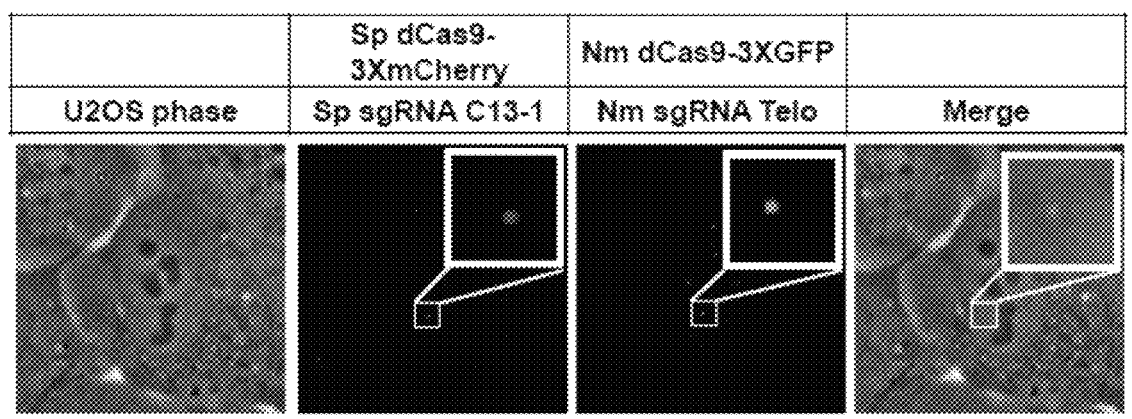
Figure 14C:
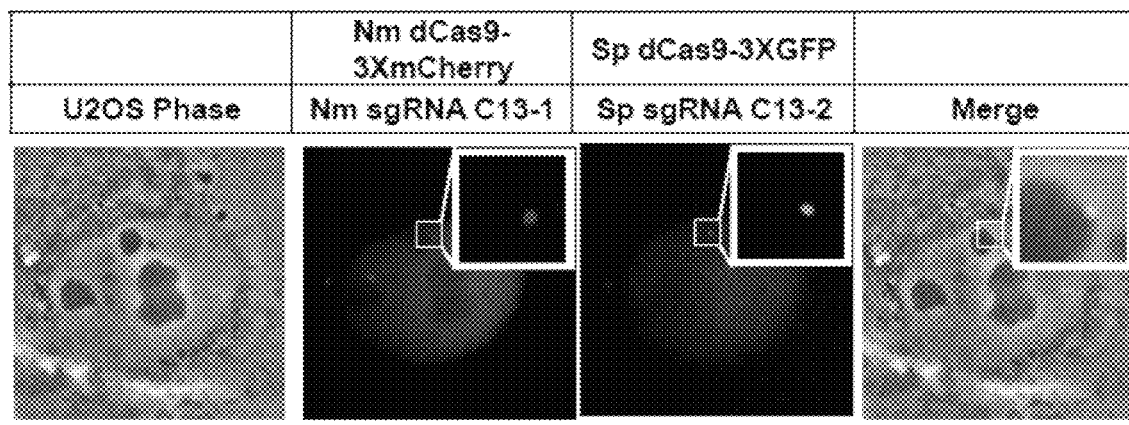
Figure 15A:
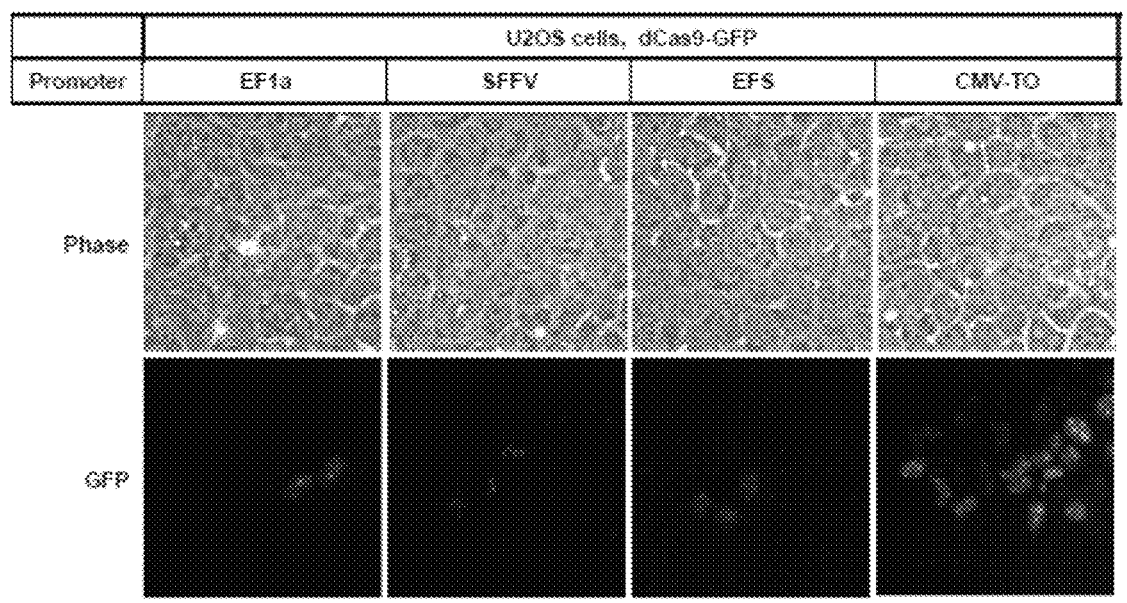
Figure 15B:
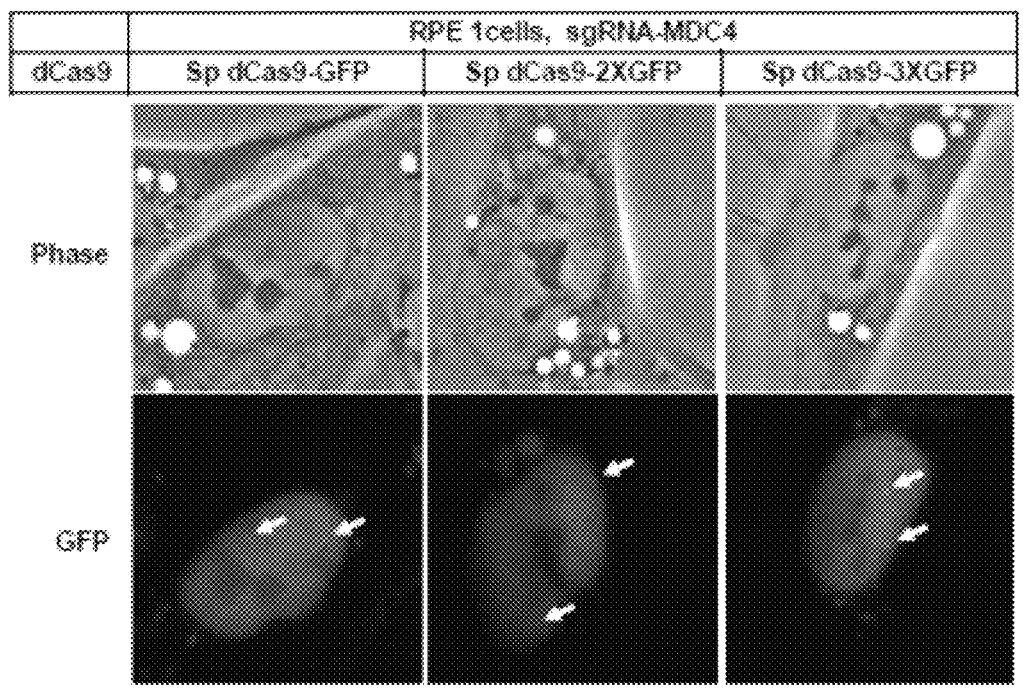
Figure 15C:
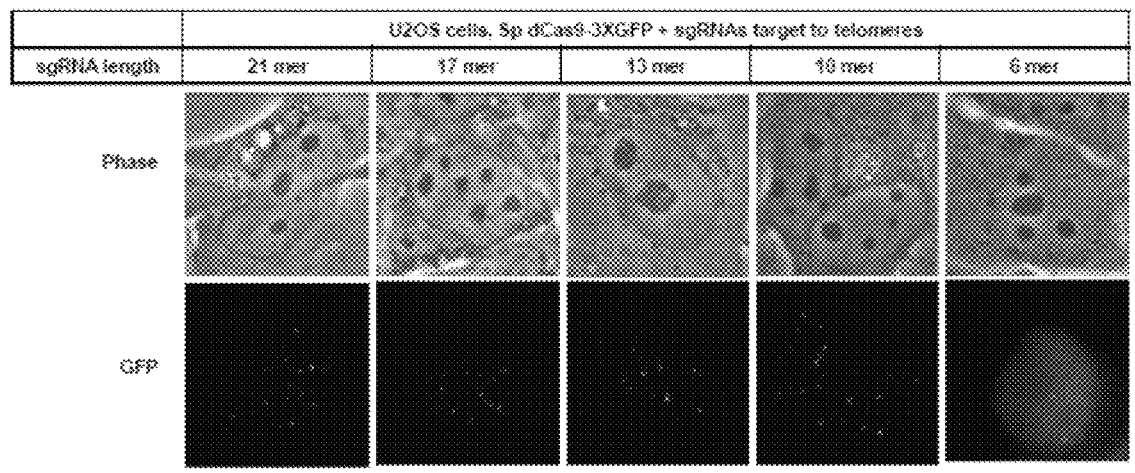
Figure 15D:
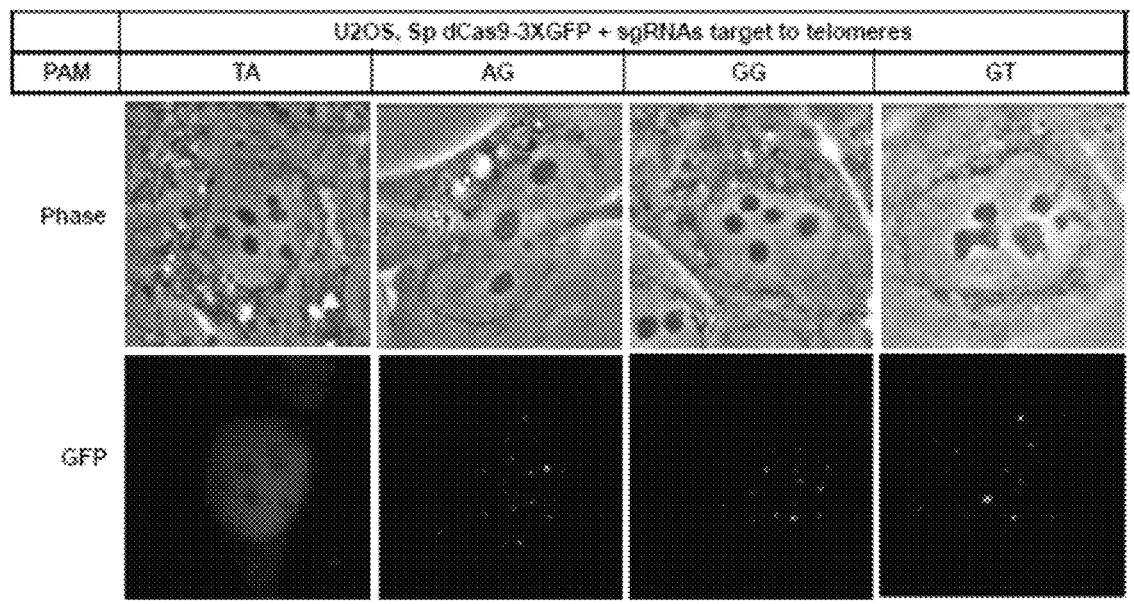
Figure 15I:
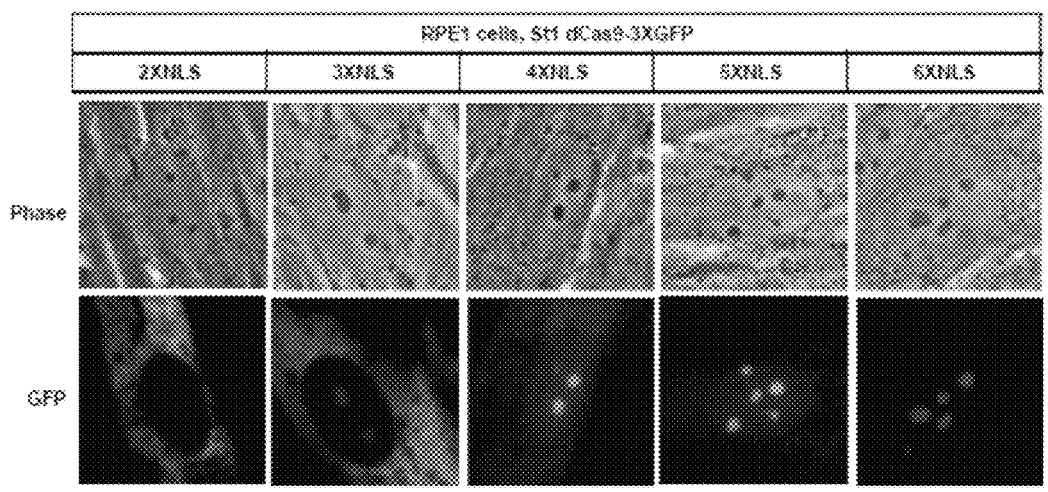
Figure 15J:
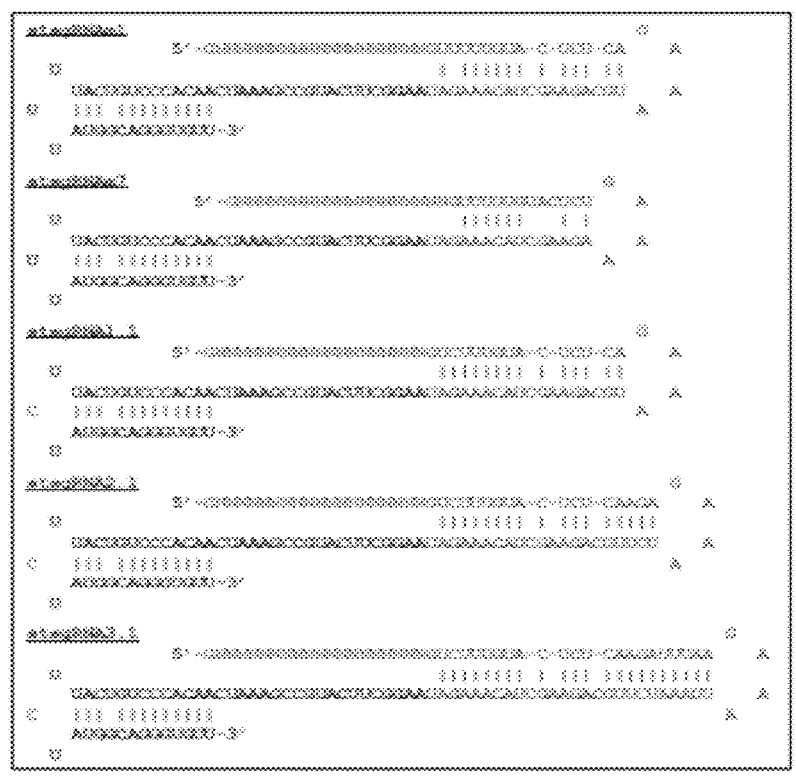

In one embodiment, a more precise estimate of the resolving power of this live cell genomic locus labeling method is obtained by choosing pairs of loci situated very close to each other for example, C13-1 sequences and an adjacent telomeric sequence. FIG. 14A. dCas9 DNA construct imaging results were obtained targeting C13-1 (red) sequences and an adjacent telomeric repeat sequence (green). The telomeres are labeled as green and multiple foci can be seen. However, it can be seen that one of the green foci lies extremely close to, but resolvable from, the C13-1 sequence (white box in "Merge"). FIG. 14B. This distance can be related to the known distance between these sequences on the chromosome 13 physical map (diagram) and thus provides information on the degree of DNA compaction of this region as it resides in the living cell. The results also show targeting of two closely positioned sequences in the subtelomeric region of chromosome 13, the C13-1 sequence and a second subtelomeric C13-2 sequence. FIG. 14C. Again, these two very closely juxtaposed loci in a live cell were readily resolved. FIG. 14C, Merge Panel. Optimization and variations of the presently disclosed dCas9 labeling method and results are shown but not discussed in detail. FIGS. 15A-15J.

A CRISPR-based multicolor labeling system disclosed herein enables the imaging of multiple endogenous genomic DNA simultaneously and allows measurement of the proximity of different genomic loci in live cells. By optimizing three orthogonal Cas9 systems with different PAM specificities, the presently disclosed system provides an expanded targeting flexibility altogether for the labeling of genomic loci. This system has a number of potential applications. The multicolor CRISPR labeling method described herein may be a useful tool for probing dynamic interactions of intra- and inter-chromosomal domains during cell cycle progression, epigenetic regulation or in response to cellular stimuli.

Figure 25:
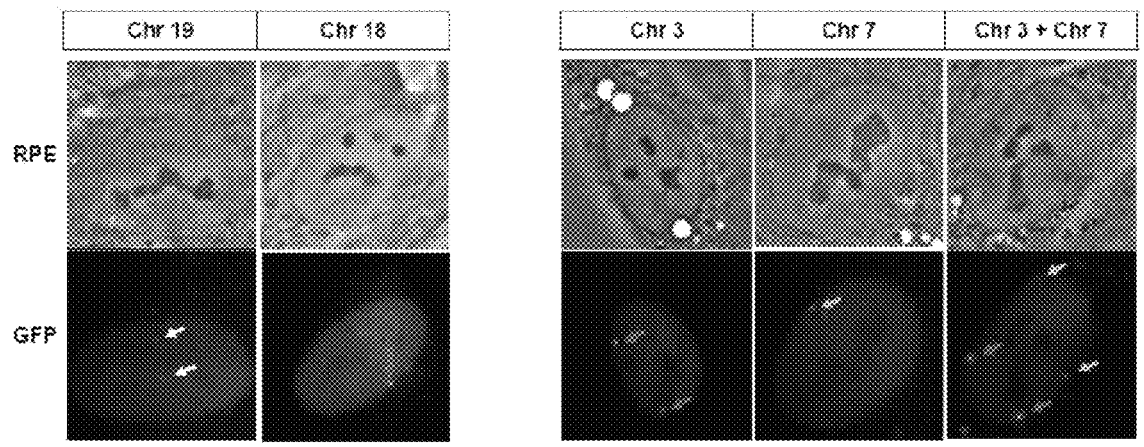
FIG. 25 presents exemplary data showing multicolor CRISPR-dCas9 binding to map the intracellular location of interphase human chromosomes (e.g., chromosome 3, 7, 18 and 19).
Figure 26:
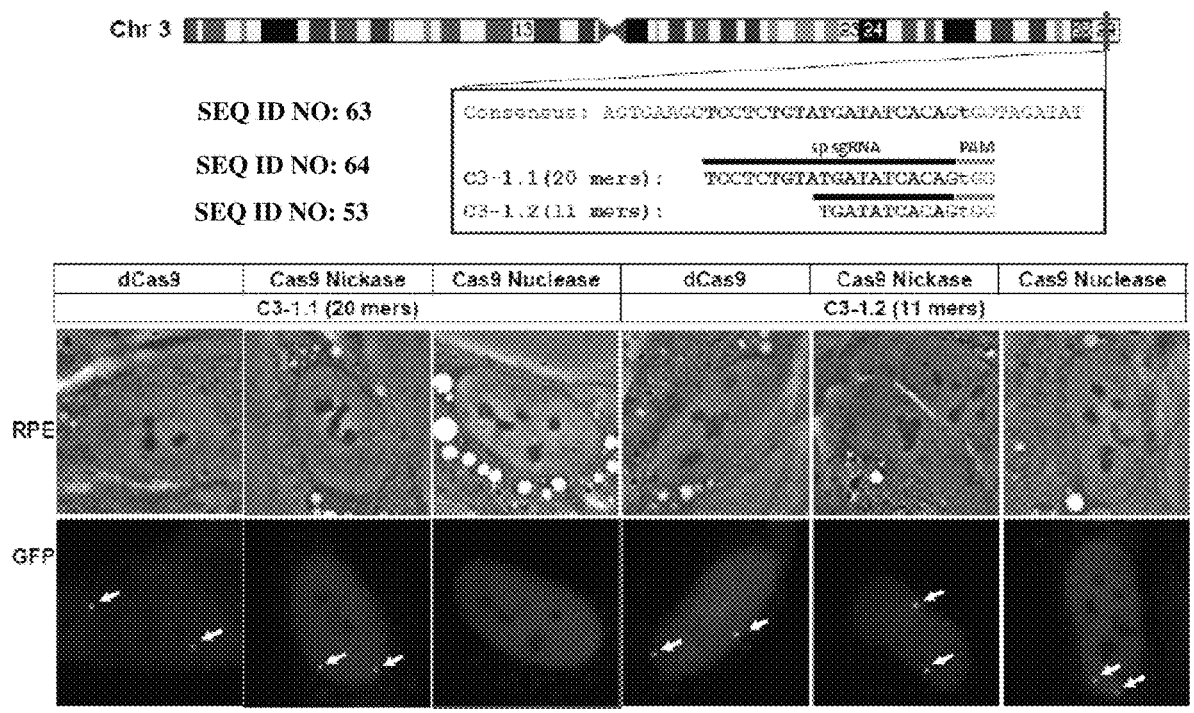
FIG. 26 presents exemplary data showing gene labeling using a switchable multicolor CRISPR-Cas9 binding to a chromosome 3 telomeric target sequence. Nickase=truncated sgRNA CRISPR-Cas9 DNA construct. Nuclease=full-length sgRNA CRISPR-Cas9 DNA construct.

In one embodiment, the present invention contemplates a method comprising mapping intra-chromosomal locations of repeated sequences. In one embodiment, the intra-chromosomal locations are unique to each human chromosome. In one embodiment, the method further comprises interrogating lamina-associated domains and chromosome capture-based topologically associating domains, thereby permitting the visualization of events such as translocations and cancer-associated chromosome shattering and rearrangements (chromothripsis) in live cells. FIG. 25.

The present method comprises any sensitivity of detection provided by state-of-the art CCD cameras that operate near or at the quantum efficiency limit and the brightness of each fluorescent protein. For example, it has been estimated that 150 to 200 fluorescent protein (FP) molecules stationed on a given chromosomal site are sufficient to create a detectable signal (i.e., ca. 50-70 dCas9-FP/sgRNA complexes in the case of using 3×GFP). However, the present invention contemplates that a repeating peptide array can recruit up to 24 copies of GFP (16) which, if successfully deployed, would significantly enhance the CRISPR/dCas9 chromosome labeling signals and extend the detection limit. Tanenbaum M E, Gilbert L A, Qi L S, Weissman J S, Vale R D. (2014) A protein-tagging system for signal amplification in gene expression and fluorescence imaging. Cell, dx.doi.org/10.1016/j.cell.2014.09. 039 (Epub ahead of print).

Superior spatial resolution has been demonstrated by detecting two chromosomal loci that lie 1.9 Mbp apart with a microscopy system in which the diffraction-limited spatial resolution is the classical Abbé limit of approximately 0.2 µm. Improvements to the spatial resolution of multicolor CRISPR/Cas9 method for detecting the propinquity of intra- or inter-chromosomal loci might be enhanced by super-resolution microscopy.

It is noteworthy that in two cases of intra-chromosomal loci presented herein, where the distance between them on the DNA physical map differed by only 0.1 Mbp, the microscopically-resolved distances differed to a greater degree, suggesting that there is a significant difference in DNA compaction in the two regions. Thus, the use of the dual color CRISPR method described here may provide a useful tool in the study of interphase DNA compaction in live cells, particularly for examining genomic regions that may have unusual chromatin structure such as pericentromeric or telomeric repeats.

The forgoing and other envisioned applications will require that sets of repeated DNA sequences can be identified that are unique to one locus on a given chromosome or are present at multiple sites only within a given chromosome (as a bar code). Many such sites are already identified, including but not limited to the sequences disclosed herein (for example, C9-1, C9-2 and C13-1).

With the method described here it should also be feasible to carry out dual color labeling of two single-copy genomic loci using tiled arrays of sgRNAs across suitable regions of each locus and their differentially colored dCas9 orthologs or, by the same strategy, between a single-copy locus and a repeated sequence lying nearby or more distant by the same strategy. In addition, Sp Cas9 has recently been adapted for programmable RNA recognition and cleavage. The simultaneous use of Sp Cas9 for RNA recognition and other Cas9 othologs for DNA recognition could provide a synergistic approach for the study of the 4-D nucleome and the regulation of eukaryotic gene expression across a broad landscape of cell types and stages of development, differentiation and human disease.

Figure 16:
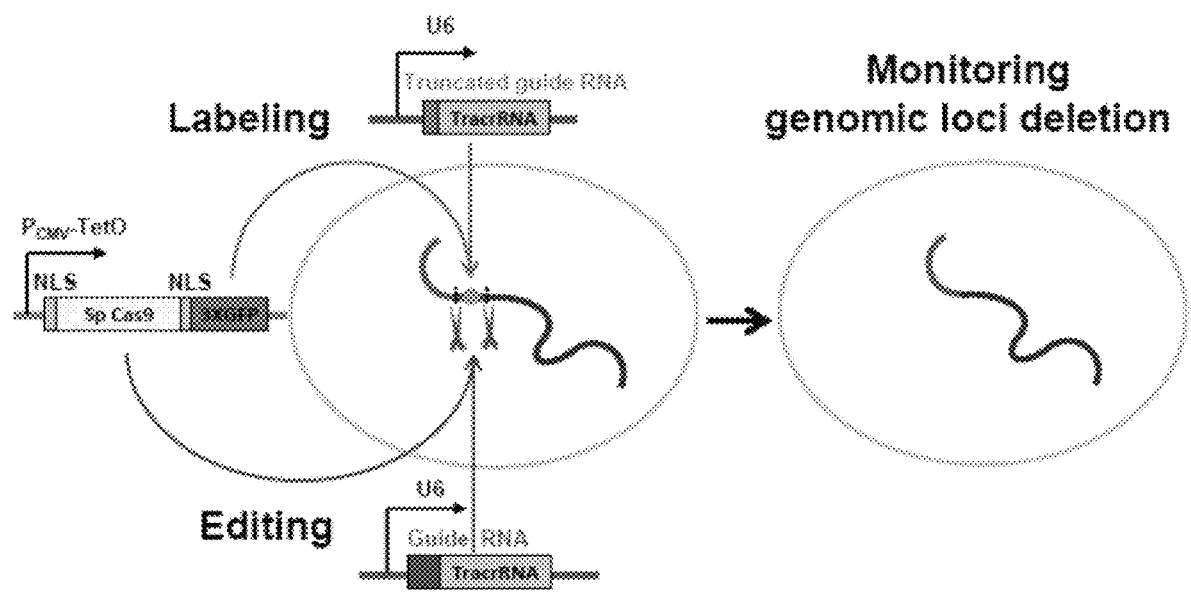
FIG. 16 shows exemplary an illustrative schematic demonstrating a switchable Cas9 DNA construct configured with either a truncated sgRNA sequence for DNA labeling or a full length sgRNA sequence for DNA editing.

B. Switchable Catalytically Active Cas9 DNA Constructs for Gene Labelling and Editing In one embodiment, the present invention contemplates a switchable CRISPR Cas9 DNA construct comprising a catalytically active nuclease. In one embodiment, the CRISPR Cas9 DNA construct comprises a catalytically active nuclease and a truncated sgRNA sequence. Although it is not necessary to understand the mechanism of an invention, it is believed that a truncated sgRNA allows the CRISPR Cas9 DNA construct to label, but not cleave the target DNA sequence thereby allowing DNA labelling. In one embodiment, the CRISPR Cas9 DNA construct comprises a catalytically active nuclease and a full-length sgRNA sequence. Although it is not necessary to understand the mechanism of an invention, it is believed that a full-length sgRNA allows a CRISPR Cas9 DNA construct to label and cleave the target DNA sequence thereby allowing DNA editing (e.g., deletion of the target DNA sequence). For purposes of clarity, this method embodiment is referred to herein as "switchable". In one embodiment, the present invention contemplates a method for treating a disease by gene editing. For example, the present invention may detect and delete disease-related DNA repeats expansion (e.g., for example, ALS-related GGGGCC repeats and myotonic dystrophy-related CTG repeats);

In one embodiment, the present invention contemplates a switchable Cas9 DNA construct comprising either: i) constructs for expression of a truncated sgRNA (a labelling switchable Cas9 DNA construct); or ii) constructs for expression of a full-length sgRNA (an editing switchable Cas9 construct). In one embodiment, labeling of a targeted genomic locus is conveyed by the action of the Cas9 and a truncated sgRNA sequence by converging green arrows and a green chromosomal signal. In one embodiment, editing of a targeted genomic locus is conveyed by the action of the Cas9 and a full length sgRNA sequence by converging red arrows and scissions flanking the targeted site. FIG. 16.

Figure 17:
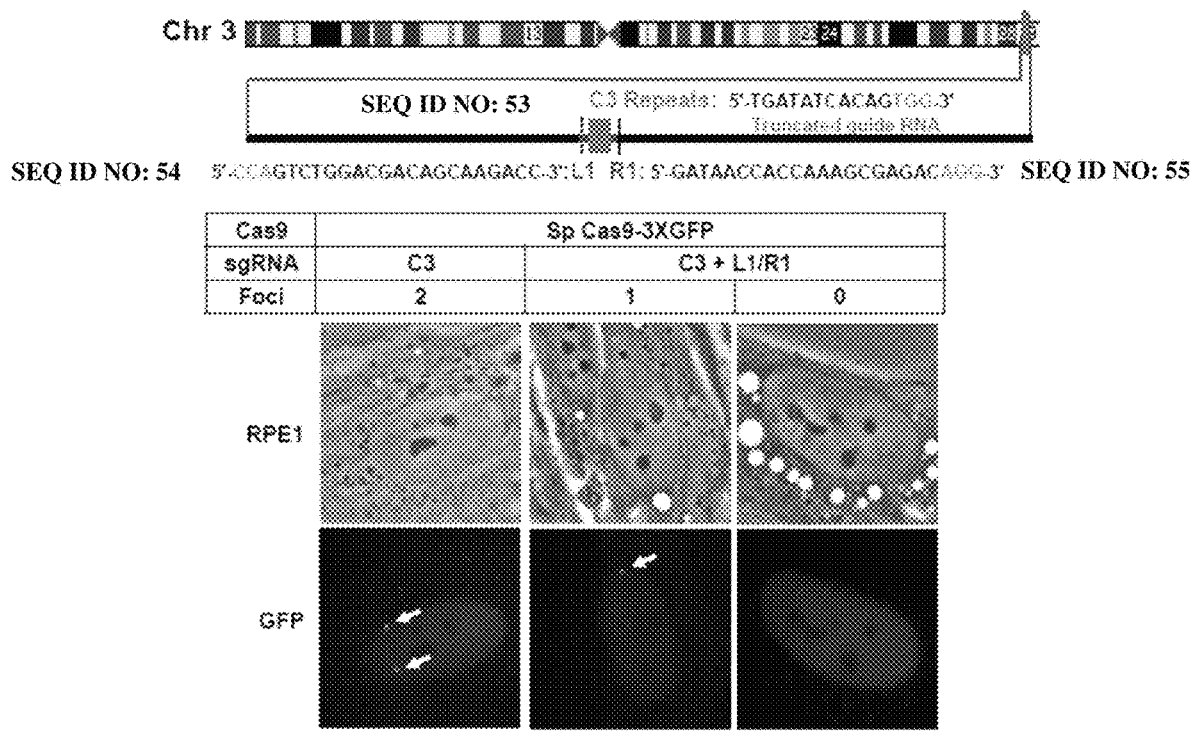
FIG. 17 presents exemplary data showing either labeling or editing using a switchable Sp Cas9 DNA construct. For labeling, a truncated sgRNA Cas9 DNA construct was used (C3). For gene editing, a full length sgRNA Cas9 DNA construct was used (L1/R1).
Figure 27:
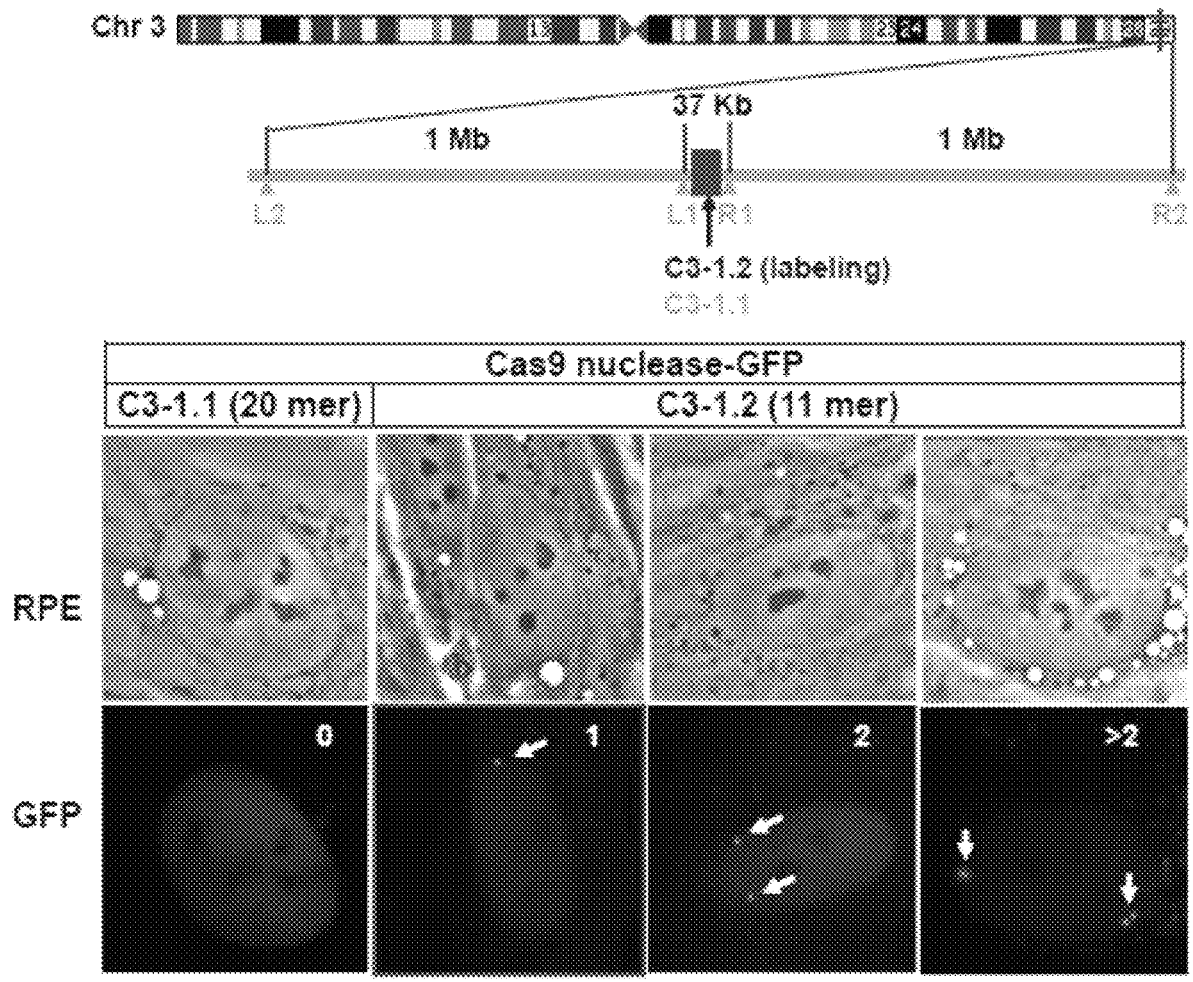
FIG. 27 presents exemplary data showing gene editing/labeling using a switchable multicolor CRISPR-Cas9 nuclease-GFP DNA complex binding to two a chromosome 3 telomeric target sequences (C3-1.1 and C3-1.2). For labeling, a truncated sgRNA Cas9 DNA construct was used. For gene editing, a full-length sgRNA Cas9 DNA construct was used.

In one embodiment, the switchable Cas9 DNA construct system labels or edits a subtelomeric site on chromosome 3 ("C3-1 repeats"). FIGS. 17 and 27. The sequence of the truncated sgRNA is shown and the full-length sgRNAs at each side of the repeats are indicated as L1 and R1. As can be seen in the live cell images, a truncated sgRNA Cas9 DNA construct (C3) resulted in labeling of the two loci in these diploid cells (left hand column). In contrast, inclusion of the full length sgRNAs (L1/R1) resulted in elimination of one or both loci (middle and right hand columns, respectively).

Figure 18:
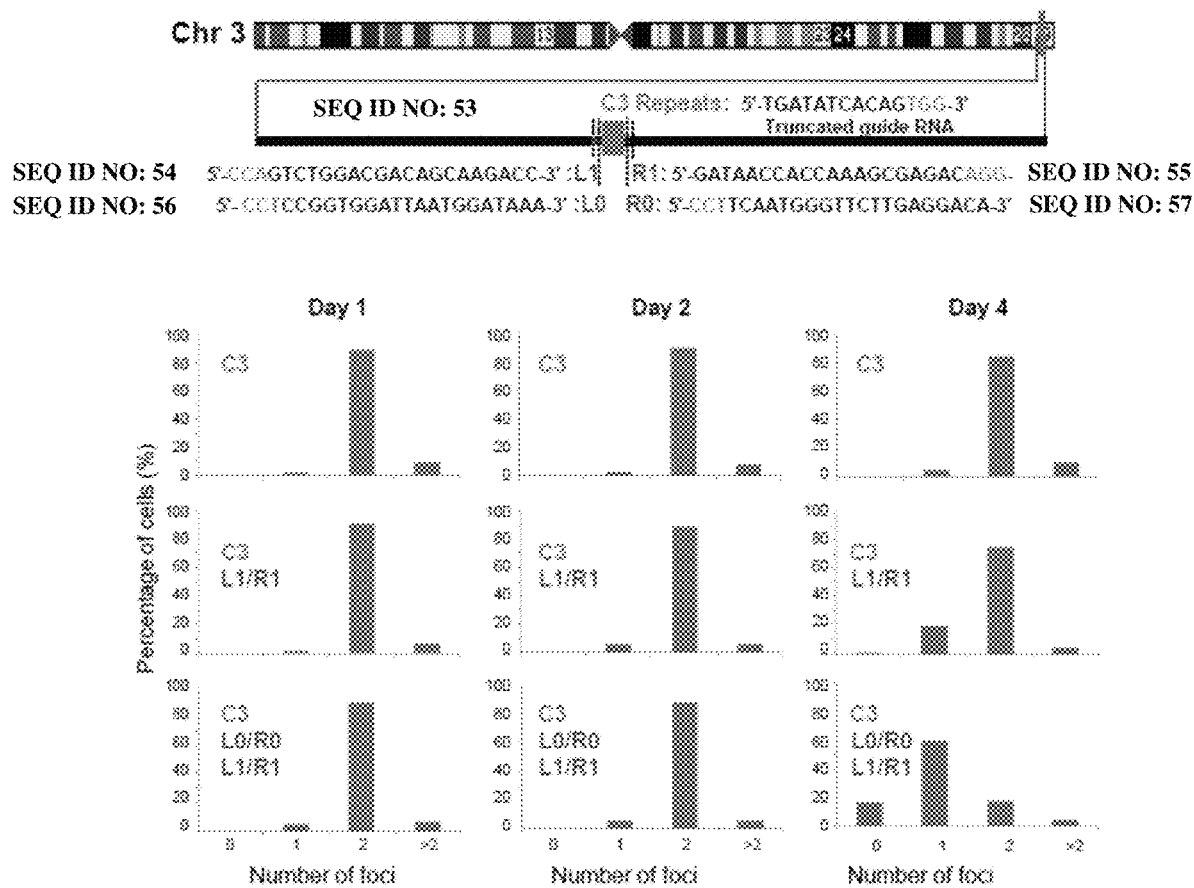
FIG. 18 presents exemplary data showing a time course of the percentage of cells in which C3-1 repeats were either labeled or edited using a switchable Cas9 DNA construct. Shown in the diagram at the top is the truncated sgRNA (C3) for labeling and two pairs of full-length sgRNAs for editing (L0/R0 and L1/R1).
Figure 28:
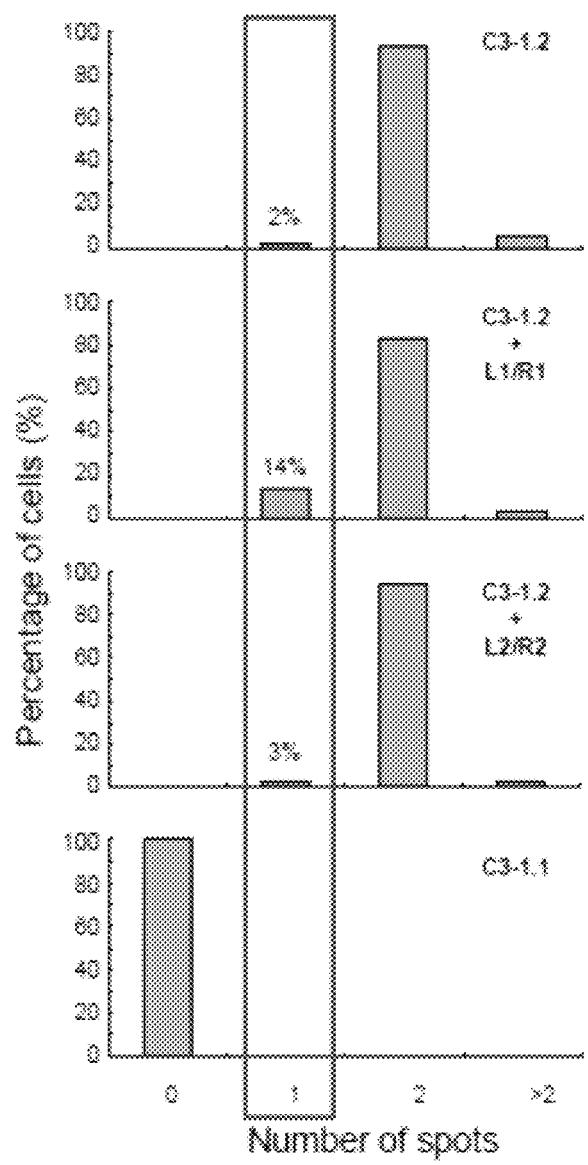
FIG. 28 presents exemplary data showing the percentage of cells in which C3-1 repeats were either labeled or edited using a switchable Cas9 DNA construct from the data of FIG. 27.

In one embodiment, the method identifies a percentage of cells in which the C3-1 repeats were labeled and/or edited was compared as a function of duration of expression. FIGS. 18 and 28. At both days 1 and 2, ~85% of cells displayed two labeled foci, irrespective of whether the truncated sgRNA was used alone, or whether one or both pairs of the full-length sgRNAs were used in addition to the truncated one. However, by day 4, a very different pattern was observed. With the truncated sgRNA ~80% of the cells displayed two foci, essentially the same as on days 1 and 2. In contrast, with one pair of full-length sgRNAs (L1/R1) there was a reduction in the percentage of cells with two foci and an increase in the percentage of those with only one. When both pairs of full-length sgRNAs were expressed, only ~20% of the cells had two foci, 60% had one and ~15% had none. Clearly, the expression of one or both pairs of full-length sgRNAs resulted in extensive editing of the targeted DNA sequence.

VII. Kits

In another embodiment, the present invention contemplates kits for the practice of the methods of this invention. In one embodiment, the kits include one or more containers containing a composition comprising a first vector encoding a nuclease-deficient Cas9 gene fused with an effector domain; and a second container comprising a second vector encoding at least one sgRNA gene; and a set of instructions for converting a pluripotent stem cell culture into a somatic cell culture. The kit can optionally include additional containers having a composition comprising an orthogonal first vector encoding a nuclease-deficient Cas9 gene fused with an effector domain and a second orthogonal vector encoding at least one sgRNA gene. In one embodiment said somatic cell culture is selected from the group consisting of a mesenchymal somatic cell, a fibroblast somatic cell, a cardiomyocyte somatic cell culture, a hematopoietic cell culture, and a pancreatic beta somatic cell culture.

In one embodiment, the kit can include one or more containers comprising a vector coding for a nuclease-deficient Cas9 (dCas9) DNA vector comprising an sgRNA targeting sequence fused with a nucleic acid sequence encoding a fluorescent protein. In one container, the fluorescent protein may include, but is not limited to, a green fluorescent protein, a red fluorescent protein, or a blue fluorescent protein.

In one embodiment, the kit can include one or more containers comprising a vector coding for a catalytically active Cas9 (switchable Cas9) DNA vector comprising a truncated sgRNA targeting sequence fused with a nucleic acid sequence encoding a fluorescent protein. In one container, the fluorescent protein may include, but is not limited to, a green fluorescent protein, a red fluorescent protein, or a blue fluorescent protein. The kit may also include a container comprising instructions for using the vector to label DNA sequences.

In one embodiment, the kit can include one or more containers comprising a vector coding for a catalytically active Cas9 (switchable Cas9) DNA vector comprising a full length sgRNA targeting sequence fused with a nucleic acid sequence encoding a fluorescent protein. In one container, the fluorescent protein may include, but is not limited to, a green fluorescent protein, a red fluorescent protein, or a blue fluorescent protein. The kit may also include a container comprising instructions for using the vector to edit DNA sequences.

The kit can optionally include enzymes capable of performing PCR (i.e., for example, DNA polymerase, Taq polymerase and/or restriction enzymes). The kit can optionally include a delivery vehicle for said vectors (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the vectors to affect the desired transcriptional regulation.

In another embodiment, the present invention contemplates kits for the practice of the methods of this invention. The kits preferably include one or more containers containing a composition comprising a first vector encoding a nuclease-deficient Cas9 gene fused with an effector domain; a second container comprising a second vector encoding at least sgRNA gene; and a set of instructions for converting a primary somatic cell culture into an induced pluripotent stem cell-derived somatic cell culture. The kit can optionally include additional containers having a composition comprising an orthogonal first vector encoding a nuclease-deficient Cas9 gene fused with an effector domain and a second orthogonal vector encoding at least one sgRNA gene. In one embodiment, said induced pluripotent stem cell derived somatic cell culture is selected from the group consisting of an induced pluripotent stem cell derived somatic neuronal cell culture, an induced pluripotent stem cell derived somatic fibroblast cell culture, an induced pluripotent stem cell derived somatic mesencymal cell culture, a midbrain dopamine somatic cell culture, a cardiomyocyte somatic cell culture, a hematopoietic cell culture and a pancreatic beta cell culture. The kit can optionally include enzymes capable of performing PCR (i.e., for example, DNA polymerase, Taq polymerase and/or restriction enzymes). The kit can optionally include a delivery vehicle for said vectors (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the vectors to affect the desired transcriptional regulation.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in affecting transcriptional regulation of cell cultures and delivery of said vectors to said cell cultures. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

The following examples are provided in order to demonstrate and further illustrate certain preferred embodiments and aspects of the present invention and are not to be construed as limiting the scope thereof.

Example 1

Cas9 Effector-Mediated Regulation of Transcription and Differentiation in Human Pluripotent Stem Cells a. sgRNA in Silico Design Candidate sgRNAs were identified by searching for (G(N) 20GG) motifs 300 bases upstream of the and 100 bases downstream of the transcriptional start site (TSS) that conform with the nucleotide requirements for U6 Pol III transcription and the spCas9 PAM recognition element (NGG) (Jinek et al., 2012 [23]; Mali et al., 2013b [4]). Bowtie2 was used to map candidate targets to the human genome (build GRCh37) (Langmead and Salzberg, 2012 [54]) with sensitive parameters (-local-f-k 10—very-sensitive-local-L 9-N 1) to detect potential off-target sites. All the sgRNAs used herein had no other genomic matches at the alignment stringency used. See, Table 3.

2013 [8])) was generated by gene synthesis (GenScript). The KRAB repressor domain (residues 1-75 from ZFN10 [*Homo sapiens*](Cong et al., 2012 [55]), Addgene 42945) was subcloned to the 3'-end of the dCas9-NLS-3×HA to generate the dCas9-KRAB lentiviral expression construct. The VP64 activation domain (from Addgene 32188, (Zhang et al., 2011 [56])) was subcloned to the 3'-end of the dCas9-NLS-3×HA to generate the dCas9-VP64 lentiviral expression construct. The sgRNA expression lentiviral vector is based on the pLKO.1 plasmid with an oligonucleotide cloning site containing two BfuAI sites for inserting guide sequences via 4 base pair 5' overhangs (ACCG & AAAC) into the sgRNA sequence (Jinek et al., 2012 [23]) (see FIG. 4).

c. Virus Production

HEK293T/17 cells were maintained in Dulbecco's Modified Eagle Medium (Gibco, 11965) supplemented with 10% fetal bovine serum (Valley Biomedical Inc., BS3033) and Glutamax (Gibco, 03505). HEK293T/17 cells were split and plated at 1.3×105 cells/cm2. Next day, packaging plasmids and dCas9, dCas9-E, or sgRNA coding plasmids were transfected using TransIT-293 transfection reagent (Mirus, 2700) in Opti-MEM (Gibco, 31985) according to the manufacturer's instruction. Virus was harvested 48 hours after transfection.

d. Human Embryonic Stem Cell Culture

H1 cell lines were maintained on Matrigel (BD Biosciences, 354277) in mTeSR1 (Stem Cell Technologies, 05850). TRE-regulated dCas9 or dCas9-E lines were supplemented with 100 ng/ml geneticin (Gibco, 10131) and EF1α-regulated dCas9-E lines with 1 µg/ml puromycin (Sigma-Aldrich). Cells were fed daily and split every 3-4 days with TrypLE Express (Gibco, 12604) in the presence of 10 µM Y-27632 (Selleck Chemicals, S1049).

TABLE 3 sgRNAs

| Name | Target Promoter | Position to TSS | Target Strand | Target Sequence (including PAM) |
|---|---|---|---|---|
| OCT4A | oct4 isoform A | -158 | template | GGGGCGCCAGTTGTGTCTCCCGG (SEQ ID No: 1) |
| OCT4A | oct4 isoform A | -12 | template | GTGGGACTGGGGAGGGAGAGAGG (SEQ ID No: 2) |
| OCT4B | oct4 isoform B | -10 | template | GGGTCCCACAAACTATAACATGG (SEQ ID No: 3) |
| OCT4B | oct4 isoform B | -15 | template | GCATGCCATGTTATAGTTTGTGG (SEQ ID No: 4) |
| SOX17 | sox17 | -126 | template | GGAGGGGCAAGGGGCGGGCGTGG (SEQ ID No: 5) |
| SOX17 | sox17 | -177 | template | GCTCCGGCTAGTTTTCCCGGGGG (SEQ ID No: 6) |
| SOX17 | sox17 | -296 | template | GGGCAAGTACGTCGATTCCAAGG (SEQ ID No: 7) |
| SOX17 | sox17 | -91 | template | GGGCGTGGGCCTAACGACGCGGG (SEQ ID No: 8) |
| CAG | CAG | | template | GTTCCGCGTTACATAACTTACGG (SEQ ID No: 9) | b. Plasmid Design and Construction

The human codon optimized, nuclease deficient Cas9 (dCas9; D10A, H840A (Jinek et al., 2012 [23]; Qi et al., Generation of stable dCas9/dCas9-E cell lines and coexpression with sgRNAs H1 cells were washed with PBS and singularized with TrypLE Express. Cells were incubated with TRE-regulated or EF1α-regulated dCas9 or dCas9-E lentivirus on low attachment plates. After 3 hours, cells were plated onto Matrigel-coated plates with 10 μM Y-27632. From 48 hours after transduction, EF1α-regulated dCas9-E transduced cells were treated with 1 μg/ml puromycin and TRE-regulated dCas9 or dCas9-E transduced cells with 100 ng/ml geneticin to select and maintain stable cell lines. For experiments utilizing sgRNAs, the appropriate stable dCas9 or dCas9-E cell lines were incubated with sgRNA lentiviruses as above and plated at 1.25×104 cells/cm2. 48 hours following transduction, TRE-regulated dCas9 or dCas9-E sgRNA transduced cells were treated with 1 μg/ml puromycin to select for cells expressing the sgRNA and 2 m/ml doxycycline (Sigma-Aldrich) to induce expression of dCas9 or dCas9-E (day 0). A sgRNA targeting the CAG (CMV-IE, chicken actin, rabbit beta globin) promoter was used as an off target control.

e. Immunofluorescence Staining

Cells were fixed with 4% paraformaldehyde for 30 minutes at room temperature then blocked for 45 minutes with 5% donkey serum (Jackson Immuno Research, 017-000-121) in PBST (PBS+0.2% Triton X-100 (Sigma-Aldrich)). Cells were incubated with primary antibodies in blocking buffer for 3 hours at room temperature, then washed 3 times with PBST. See, Table 4.

TABLE 4

Primary Antibodies

| Antibody | Source | Dilution |
|---|---|---|
| CDX2 | Mouse monoclonal, BioGenex MU392A-UC | 1:300 |
| HA | Rat monoclonal, Roche 11867431001 | 1:500 |
| NANOG | Rabbit polyclonal, Abcam ab21624 | 1:400 |
| OCT4A | Mouse monoclonal, Santa Cruz Biotechnology sc-5279 | 1:100 |
| OCT4A | Goat polyclonal, Santa Cruz Biotechnology sc-8628 | 1:500 |
| SOX17 | Goat polyclonal, R&D Systems AF1924 | 1:300 |
| T | Goat polyclonal, Santa Cruz Biotechnology sc-17743 | 1:300 |

Cells were incubated with Alexa-Fluor conjugated secondary antibodies (Invitrogen, 1:300) for 2 hours at room temperature and washed 3 times with PBST. Nuclei were stained with Hoechst (Invitrogen, H3570). Phase contrast images were acquired on Nikon Eclipse TS100 and fluorescent images on Nikon Eclipse Ti microscopes. Cells were quantitated using NIS-Elements Analysis Software. 10 random fields at 20× magnification were counted (3400-5000 cells identified through Hoechst staining) and the mean fluorescence intensity of SOX17 signal in each cell calculated based on a threshold set using the CAG-sgRNA control.

f. Quantitative PCR Analysis

RNA was isolated using Trizol Reagent (Invitrogen, 15596-018) according to the manufacturer's instructions. 2 g (SOX17 analysis) or 250 ng (OCT4 analysis) of total RNA was reverse-transcribed using SuperScript III First-Strand Synthesis System (Invitrogen, 18080-051). 30 ng (SOX17 analysis) or 3.75 ng (OCT4 analysis) of cDNA was utilized in qPCR reactions using specific primers in iTAQ Universal SYBR Green Supermix (Biorad, 172-5124) or by the following TaqMan assays: ACTB (Hs01060665_g1), SOX17 (Hs00751752_s1). Relative gene expression was calculated using the CT method; all genes were normalized to ACTB. See, Table 5.

TABLE 5 qPCR primers

| Gene | Forward Primer | Reverse Primer |
|---|---|---|
| ACTB | TGGCACCACACCTTCTACAA TGA (SEQ ID No: 10) | CAGCCTGGATAGCAACGTACAT (SEQ ID No: 11) |
| AFP | AGAACCTGTCACAAGCTGTG (SEQ ID No: 12) | GACAGCAAGCTGAGGATGTC (SEQ ID No: 13) |
| CDX2 | GGGCTCTCTGAGAGGCAGGT (SEQ ID No: 14) | CCTTTGCTCTGCGGTTCTG (SEQ ID No: 15) |
| SOX7 | ACGCCGAGCTCAGCAAGAT (SEQ ID No: 16) | TCCACGTACGGCCTCTTCTG (SEQID No: 17) |
| T | TGCTTCCCTGAGACCCAGTT (SEQ ID No: 68) | GATCACTTCTTTCCTTTGCAT CAAG (SEQ ID No: 69) | g. Epigenetic Data Analysis

FIG. 2A and FIG. 3A were generated from the Integrative Genome Viewer (IGV) (Robinson et al., 2011) using the publicly available ENCODE epigenetic sequence data for the human H1 cell line.

Example 2 dCas9-Mediated Reprogramming of Human Fibroblasts to iPSCs

Since the groundbreaking work by Yamanaka and colleagues [15] that demonstrated the feasibility of reprogramming cellular identity with OCT4, SOX2, KLF4 and cMYC (OSKM), intense scientific effort has focused on understanding the mechanism of this process and improving it through the identification of additional collaborating TFs and the substitution/inclusion of small molecules or non-coding RNAs [25]. Artificial TFs that activate expression of individual TFs within the OSKM set can substitute for a single factor (e.g. SKM with a TALE-VP64 fusion that activates OCT4 can reprogram fibroblasts to iPSCs [36]). Fibroblast reprogramming to iPSCs will be used as a framework for the initial demonstration the multi-target activation via dspCR-SIPRa can yield functional differentiation state choices. Initial experiments will focus on the iterative substitution of single OSKM factor with a dspCas9-VP64 effector targeting one of these genes (e.g. a single sgRNAs targeting OCT4 (OCT4A-158 sgRNA, Example 1) with the SKM factors delivered through lentiviral transduction). The efficiency of iPSC formation from human BJ foreskin fibroblasts will be determined based on alkaline phosphatase positive colonies followed by evaluation of expressed pluripotency markers [57] (e.g. SSEA4, NANOG, TRA1-60, and TRA1-81). Following the identification of sgRNAs with dspCas9-VP64 that can efficiently substitute for each OSKM member in reprogramming, all of these sgRNAs will be combined to examine the efficiency of dspCas9-VP64 mediated reprogramming in the absence of the Yamanaka factors (OSKM). Successful reprogramming using dspCas9-VP64 may be confirmed by teratoma formation assays in NOD-SCID mice [57]. Parameters such as MOI and the influence of small molecules that assist in silenced gene reactivation (5'-azaC and valproic acid [58]) will be examined to assess how they impact the efficiency of reprogramming, as these parameters will likely also be critical for the combinatorial experiments described later in subsequent examples.

Given the success in repressing OCT4 and SOX2 with dspCas9-KRAB (see Example 1 above), it is anticipated that there will be success in reprogramming fibroblasts when substituting CRISPRe for a single Yamanaka factor. It is possible that in some instances reprogramming may require the assistance of additional small molecules to increase the accessibility of silenced genomic regions [59]. Completely eliminating all of the Yamanaka factors for reprogramming may likely prove more challenging, primarily due to the need to achieve infection of single cells with multiple lentiviral vectors carrying the different targeting sgRNAs. However, this is a critical feature to troubleshoot before an attempt using combinatorial screens is made. Potential Problems: If reactivation of any of the Yamanaka factors at the proximal promoter proves problematic, the active enhancers associated with these genes in the pluripotent state will be targeted, as this was necessary for the functional activation of OCT4 with a TALE-VP64 TF [36]. Should the leap from single factor substitution to substituting all four factors prove challenging an iterative process may be employed where one bootstraps from one to two to three to four substitutions, optimizing the protocol as it proceeds. Should the high MOI level necessary for activating all four OSKM factors prove to be a serious problem limiting efficiency, ways to stack a plurality of sgRNAs in a single expression cassette will be examined.

Example 3

Identification of Factors Generating a Definitive Endoderm (DE) from hESCs

The first major differentiation state from ESCs to endodermal lineages may involve the transition to DE [60-62]. Monolayer cell culture conditions that efficiently generate DE through activation of the wingless (WNT) and TGFβ signaling pathways are well defined [60, 63]. This well-defined lineage will be used to test the ability of the CRISPRe/i system to program cell fate decisions (Schematic overview of the approach given in FIG. 8A). As a testing ground, directing hESCs to an endodermal fate has several benefits: First, diagnostic markers of DE have been defined (e.g. CXCR4, GATA3, FOXA3, etc.) [60, 63-66], and detection of intracellular SOX17 with FOXA2 or surface expression of CXCR4 and c-Kit have been used to distinguish DE from ESCs by FACS [60, 64, 67]. This provides a robust and sensitive assay for the identification of cells that have differentiated from hESCs to DE. Second, critical factors that promote the generation of DE, such as SOX17 [66], have been defined, although in the Example 1 experiments the activation of SOX17 in isolation via dspCas9-VP64 does not promote the generation of DE under the hESC maintenance conditions previously used. To guide the choice of factors to up and downregulate to direct DE generation from ESCs, a candidate approach will be followed. To this end directed differentiation protocols have been adopted to guide hESCs through a definitive endoderm intermediate to anterior foregut endoderm [64, 68]. Histone-modification specific chromatin immunoprecipitation have been performed on each of these states to identify specific transcription factors that become activated (Histone3 K4me2+) during the course of differentiation (FIG. 8B). Datasets that compare the expression profiles of mouse ESCs and enriched endodermal and anterior foregut derivatives have been mined to identify differentially expressed transcription factors ([64], GEO GSE42139, and unpublished Affymetrix gene ST 1.0 arrays). Data on 1500 TFs from these experiments have been analyzed in conjunction with 250 publically available expression data sets spanning different cell and tissue types employing the Jensen-Shannon divergence of a gene's expression pattern to extract a tissue specificity score [69, 70]. In combination the chromatin and expression data may allow to for a defined the change in gene transcriptional state or expression, and thereby to assign TF sets to activate (via dspCRISPRa) or repress (via dnmCRISPRi). Candidate transcription factors that have support in both sets of data analysis will be given priority in the programming efforts as those likely represent genes that are specifically turned on during the differentiation process toward endoderm and subsequently anterior foregut (see Example 4).

A library of sgRNAs will be created targeting the top 50 genes within the list. These will be partitioned between spsgRNAs and nmsgRNAs depending on whether the target gene needs to be activated (dspCas9-VP64) or repressed (dnmCas9-KRAB). Depending on the number of sgRNAs required per gene for efficient regulation, the number of target genes within the library will be adjusted and the MOI used in the screen, which will follow the layout in FIG. 8A. For example, if a single sgRNA per gene can be used for effective regulation, and it is believed that 6 critical genes need to be perturbed within the list to achieve the desired regulatory output, this as a counting problem can be approximated (with the simplifying assumption that the number of infections is uniform across the population): where the number of cells to isolate a desired combination=binomial [#targets, #critical genes]/binomial [MOI, #critical genes]. This is a simplification that ignores the distribution of infections across the population as a function of MOI, but it provides a framework for thinking about the complexity of this system. For 6 critical genes among 50 targets an MOI of 12 will yield the needed combination of 6 about every 18,000 cells. Thus in a plate of 10^6 cells there would be about 58 positives. Depending on the parameters defined, the number of targets will be adjusted and the MOI to achieve an expected 20 positives per plate for the screen, where 20 plates per screen (~1000 positives) would be covered. The validity of this approximation will be guided by the reprogramming experiments in Example 2, where the MOI necessary with the CRISPRe/i system to achieve the maximal rate of reprogramming when targeting four genes will be defined.

Positive DE cells (with CXCR4 and c-Kit coexpressed) following the time course will be isolated by FACS. Integrated sgRNA cassettes will be amplified from positive clones as a pool and subsequently identified by deep sequencing [31]. Alternatively, a recently developed endoderm progenitor culture platform [71] will be applied that will allow a similar approach as taken by Dr. Yamanaka by providing a growth advantage for the cell type of interest [15]. Overrepresented sgRNAs from positive clones will be retested as defined combinations to validate the critical sets required to drive hESCs to DE, and to verify that these sgRNA combinations do not yield cells with ectoderm or mesoderm markers. Finally, DE progenitor cell identity will be verified on molecular and functional level. First, cells will be analyzed for expression of endodermal transcription factors and cell surface markers as previously described [60]. Subsequently, directed differentiation and spontaneous differentiation approaches will be employed to test the differentiation capacity of the cells. Specifically, established in vitro differentiation protocols will be used to guide endodermal cells toward progenitors to thymic epithelial cells and pancreatic beta cells [62, 72], and employ immunocompromised mice to assess the spontaneous differentiation potential of the obtained endodermal cells as has been described previously [64].

Example 4

Identification of Factors Generating Anterior Foregut Endoderm (AFE) from DE Progenitors Recent progress had been made in guiding endoderm toward anterior foregut endoderm and its derivatives [64, 68, 72-75]. However, in comparison to other endodermal lineages (e.g. pancreatic lineage) less is known about the underlying transcriptional networks guiding this process. Based on previous studies [76, 77], conditions have been adopted and optimized that allow the generation of a nearly homogenous monolayer culture with DE progenitors cells where ~95% of the cells have the diagnostic markers (SOX17 and FOXA2) for this differentiation state [64]. Defined robust conditions have been established for differentiating endoderm towards anterior foregut (~60%) through inhibition of TGFbeta and BMP pathways as described previously [68]. In this context, sensitive detection methodology has been established that allows the detection of AFE cells by immunofluorescence and FACS analysis (FIG. 8C). Otherwise with regards to the parameters of the screen, it will be guided by the results of the screen in Example 3, where the target list will be drawn from the expression and ChIP-seq data on the two cell states (DE and AFE) that have already been generated and analyzed (FIG. 8B). TF combinations identified in the screen will be validated by demonstrating that when reintroduced into DE progenitors that they can drive efficient differentiation into AFE. Finally, AFE cell identity will be verified by transplantation into NOD-SCID mice to stain for the expected maturation markers [64].

Expected Results: a similar troubleshooting approach to that described in Example 3 will be followed. It is anticipated that this screen will successfully identify TFs that drive the directed differentiation of DE progenitors to AFE cells. If this can be achieved, this same approach could be applied to a variety of differentiation pathways of interest (mature beta cells or thymic epithelial cells) to define their key regulators.

Thus, specific compositions and configurations of Cas9 effector-mediated regulation of transcription and differentiation in stem cells have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Example 5

Construction of Cas9 Expression Plasmids

Human-codon optimized dCas9 (nuclease-dead) from S. pyogenes (18), N. meningitidis and S. thermophilus (15) were fused to 1×GFP, 2×GFP, 3×GFP, 3×mCherry or 3×TagBFP and subcloned into pHAGE-DEST lentiviral vector. Esvelt K M, et al. Orthogonal Cas9 proteins for RNA-guided gene regulation and editing. Nat. Methods 10(11): 1116-1121; and Kearns N A, et al. (2014) Cas9 effector-mediated regulation of transcription and differentiation in human pluripotent stem cells. Development 141 (1):219-223.

To optimize the promoters for U2OS and RPE1 cells, the EF1α promoter in the pHAGE-EF1α-DEST vector was replaced by EFS, SFFV and CMV-TetO promoters respectively and results in the pHAGE-EFS-DEST, pHAGE-SFFV-DEST and pHAGE-TO-DEST. To optimize the nuclear localization, 2×SV40 NLSs were fused to S. pyogenes dCas9, N. meningitidis dCas9, while up to 6×SV40 NLSs were fused to S. thermophilus dCas9. A list of Cas9 labeled fusion proteins constructed is shown in Table 6.

TABLE 6

Exemplary Cas9 Labeled Fusion Proteins

| | Promoter | dCas9 Fusion protein | NLS |
|---|---|---|---|
| 1 | EF1 α | NLS-Sp dCas9-NLS-sfGFP | 2X |
| 2 | SSFV | NLS-Sp dCas9-NLS-sfGFP | 2X |
| 3 | EFS | NLS-Sp dCas9-NLS-sfGFP | 2X |
| 4 | CMV-TetO | NLS-Sp dCas9-NLS-sfGFP | 2X |
| 5 | CMV-TetO | NLS-Sp dCas9-NLS-2XsfGFP | 2X |
| 6 | CMV-TetO | NLS-Sp dCas9-NLS-3XsfGFP | 2X |
| 7 | CMV-TetO | NLS-Sp dCas9-NLS-3XmCherry | 2X |
| 8 | CMV-TetO | NLS-Nm dCas9-NLS-3XsfGFP | 2X |
| 9 | CMV-TetO | NLS-Nm dCas9-NLS-3XmCherry | 2X |
| 10 | CMV-TetO | NLS-St1 dCas9-NLS-3XsfGFP | 2X |
| 11 | CMV-TetO | NLS-St1 dCas9-2XNLS-3XsfGFP | 3X |
| 12 | CMV-TetO | NLS-St1 dCas9-3XNLS-3XsfGFP | 4X |
| 13 | CMV-TetO | NLS-St1 dCas9-3XNLS-3XTagBFP2 | 4X |
| 14 | CMV-TetO | NLS-St1 dCas9-3XNLS-3XsfGFP-NLS | 5X |
| 15 | CMV-TetO | NLS-St1 dCas9-3XNLS-3XsfGFP-2XNLS | 6X |

All the plasmids reported here will be deposited at Addgene and are freely available to academic researchers Example 6

Construction of sgRNA Expression Vectors

The sgRNA expression vector is based on the pLKO.1 lentiviral expression plasmid containing CcdB gene between two BbsI sites for inserting guide sequences into the sgRNAs. Optimized sgRNA for S. pyogenes Cas9 was subcloned into pLKO.1-Hygro, resulting in pLH-Sp sgRNA2. Nm sgRNA mutants for N. meningitidis Cas9 were subcloned into pLKO.1-Hygro, resulting in pLH-Nm sgRNAm1 and pLHNm sgRNA1.1. St' sgRNA mutants for S. thermophilus Cas9 were subcloned into pLKO.1-Hygro, resulting in pLH-St1 sgRNAm1, pLH-St1 sgRNAm7, pLHSt1 sgRNA1.1, pLH-St1 sgRNA2.1 and pLH-St1 sgRNA3.1. A rapid guide RNA expression plasmids construction protocol was optimized as follows: a pair of oligos (2 μM) were denaturing at 95° C. for 3 min and cooling down to room temperature, and the mixture of oligos (4 nM) and sgRNA vectors (100 ng) were quickly digested by BbsI and ligated by T7 ligase at 37° C. for 10 min in the same tubes, and then directly subjected to transformation using CcdB as counter-selection. The sgRNA vectors and guide RNA sequences are listed in Tables 7 and 8 respectively.

TABLE 7

Exemplary sgRNA Vectors

| | Vector Name | sgRNA expression vector Cassette |
|---|---|---|
| 1 | pLH-Sp sgRNA2 | U6 promoter-BbsI-CcdB-BbsI-Sp sgRNA2 |
| 2 | pLH-Nm sgRNAm3 | U6 promoter-BbsI-CcdB-BbsI-Nm sgRNAm3 |

TABLE 7-continued

Exemplary sgRNA Vectors

| | Vector Name | sgRNA expression vector Cassette |
|---|---|---|
| 3 | pLH-Nm sgRNA1.1 | U6 promoter-BbsI-CcdB-BbsI-Nm sgRNA1.1 |
| 4 | pLH-St1 sgRNAm1 | U6 promoter-BbsI-CcdB-BbsI-St1 sgRNAm1 |
| 5 | pLH-St1 sgRNAm7 | U6 promoter-BbsI-CcdB-BbsI-St1 sgRNAm7 |
| 6 | pLH-St1 sgRNA1.1 | U6 promoter-BbsI-CcdB-BbsI-St1 sgRNA1.1 |
| 7 | pLH-St1 sgRNA2.1 | U6 promoter-BbsI-CcdB-BbsI-St1 sgRNA2.1 |
| 8 | pLH-St1 sgRNAS.1 | U6 promoter-BbsI-CcdB-BbsI-St1 sgRNA\3.1 |

TABLE 8

| | | dCas9 | Target | Guide RNA sequence | PAM |
|---|---|---|---|---|---|
| 1 | SEQ ID NO: 18 | S. pyogenes | DMC4 | GTGGCGTGACCTGTGGATGCTG | GG |
| 2 | SEQ ID NO: 19 | S. pyogenes | Telo-TA | GGTTAGGGTTAGGGTTAGGG | TA |
| 3 | SEQ ID NO: 23 | S. pyogenes | Telo-GT | AGGGTTAGGGTTAGGGTTAG | GT |
| 4 | SEQ ID NO: 24 | S. pyogenes | Telo-AG | GTTAGGGTTAGGGTTAGGGT | AG |
| 5 | SEQ ID NO: 25 | S. pyogenes | Sp-Telo | TTAGGGTTAGGGTTAGGGTT | GG |
| 6 | SEQ ID NO: 26 | S. pyogenes | Telo-17 | GGGTTAGGGTTAGGGTT | GG |
| 7 | SEQ ID NO: 27 | S. pyogenes | Telo-13 | TAGGGTTAGGGTT | GG |
| 8 | | S. pyogenes | Telo-10 | GTTAGGGTT | GG |
| 9 | | S. pyogenes | Telo-06 | AGGGTT | GG |
| 10 | SEQ ID NO: 28 | S. pyogenes | C9-1 | TGGAATGGAATGGAATGGAA | GG |
| 11 | SEQ ID NO: 29 | S. pyogenes | C9-2 | TGTCTGTGAGGAAGCTCCCC | GG |
| 12 | SEQ ID NO: 30 | S. pyogenes | C13-1 | TAAGCATGGACCATTCCTTC | GG |
| 13 | SEQ ID NO: 31 | S. Pyogenes | C13-2 | GGGCCAGGACCTCTAAAA | GG |
| | SEQ ID NO: 32 | | | CCGGGGAAGTGCTGAGTC | GG |
| | SEQ ID NO: 33 | | | TGGTGGGTGTAGACACGG | GG |
| 14 | SEQ ID NO: 34 | N. meningitidis | Telo-AGGG | GGTTAGGGTTAGGGTTAGGGTTAG | AGGG |
| 15 | SEQ ID NO: 35 | N. meningitidis | Telo-GGGT | GTTAGGGTTAGGGTTAGGGTTAGG | GGGT |
| 16 | SEQ ID NO: 36 | N. meningitidis | Nm-Telo | TTAGGGTTAGGGTTAGGGTTAGGG | GGTT |
| 17 | SEQ ID NO: 37 | N. meningitidis | Telo-GTTA | TAGGGTTAGGGTTAGGGTTAGGGT | GTTA |
| 18 | SEQ ID NO: 38 | N. meningitidis | C13-1 | CTCCATCCTGAAGGAATGGTCCAT | GCTT |
| 19 | SEQ ID NO: 19 | S. thermophilus | St1-Telo | GGTTAGGGTTAGGGTTAGGG | AGGG |
| 20 | SEQ ID NO: 39 | S. thermophilus | C9-1 | ATGGAATGGAATGGAATGGA | GGAA |

Example 7

Cell Culture and Transfection

U2OS cells were cultured at 37° C. in Dulbecco-modified Eagle's Minimum Essential Medium (DMEM; Life Technologies) supplemented with 10% (vol/vol) FBS. RPE1 cells were kindly provided by Dr. Yumi Uetake (Department of Cell and Developmental Biology, University of Massachusetts Medical School) and cultured at 37° C. in DMEM:F12 medium supplemented with 10% (vol/vol) FBS. For live imaging, cells were grown on 35 mm glass bottom dishes (MatTek). In experiments with U2OS cells, a total of 150 ng dCas9 and 750 ng sgRNAs plasmid were cotransfected into 35 mm glass bottom dishes using Lipofectamine 2000 (Life Technologies) and the cells were incubated for another 48 hours. For RPE1 cells, a total of 50 ng dCas9 and 250 ng sgRNAs plasmids were co-transfected into 35 mm glass bottom dishes using Lipofectamine LTX (Life Technologies).

Example 8

Fluorescence Microscopy

The microscope stage incubation chamber was maintained at 37° C. (19) and phase-contrast and fluorescence microscopy was performed as described previously. Jacobson M R, Pederson T (1997) RNA traffic and localization reported by fluorescence cytochemistry. Analysis of mRNA Formation and Function, ed Richter J D (Academic, New York), pp 341-359; and Ma H, Reyes-Gutierrez P, Pederson T (2013) Visualization of repetitive DNA sequences in human chromosomes with transcription activator-like effectors. Proc Natl Acad Sci USA 110(52):21048-21053. mCherry was excited at 556/20 nm (wavelength/bandwidth) and its emission was collected in a 630/91 nm channel. sfGFP was excited at 470/28 nm and its emission was collected in a 512/23 nm channel; TagBFP was excited at 387/11 nm and its emission collected using a 464/23 nm filter. Imaging data were acquired and analyzed by Meta-Morph acquisition software (Molecular Devices).

Example 9

Mining for Chromosome-Specific Repeats

The human reference genome hg19 was downloaded from the UCSC genome browser (genome.ucsc.edu). The gaps (regions labeled with N's) in chromosomes 9 and 13 were replaced with randomly generated nucleotides. The bioinformatics tool Tandem Repeat Finder was used to identify tandem repeats in chromosomes 9 and 13. Benson G (1999) Tandem repeats finder: a program to analyze DNA sequences. Nucleic Acids Res. 27(2):573-580.

Highly conserved repeats with copy numbers >100 were selected as candidates for CRISPR labeling. 23-mers in the tandem repeats ending with GG were used for design of Sp sgRNAs for C9-1, C9-2, C13-1, C13-2. 28-mers ending with GCTT were used for design of Nm sgRNAs for C13-1 and 26-mers ending with GGAA were used for design of St1 sgRNA for C9-1.

The detailed parameters for each targeted repeats are as follows. C9-2 is located in a subtelomeric region q34.3 of chr 9 with the location chr9: 140459676-140463065 and contains 115 copies of sgRNA target sites. C13-1 consists of 177 copies of sgRNA target sites, located in the subtelomeric region q34 of chr 13 with the location chr 13: 112930173-112968847. C13-2 consists of three neighboring tandem repeats in q34 of chr 13 chosen to achieve a combined 102 copies of sgRNA target sites with the following locations: chr13: 114793685-114795158 with 22 copies of target sites; chr13: 114848979-114852850 with 57 copies of target sites; chr13: 114903631-114905572 with 23 copies of target sites.

A BLAT alignment tool was used to verify the chromosome specificity of these sgRNA target sites in human genome Kent W J (2002) BLAT-the blast-like alignment tool. Genome Res. 12(4):656-664.

C9-1 was a tandem array of GGAAT repeats, which are highly concentrated in the pericentromeric region of chr 9. Eymery A, Souchier C, Vourc'h C, Jolly C. (2010) Heat shock factor 1 binds to and transcribes satellite II and III sequences at several pericentromeric regions in heat-shocked cells. Exp Cell Res 316(11):1845-1855.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

1. Wiedenheft, B. et al. (2012) "RNA-guided genetic silencing systems in bacteria and archaea," Nature 482(7385), 331-338.
2. Charpentier, E. and Doudna, J. A. (2013) "Biotechnology: Rewriting a genome," Nature 495(7439), 50-51.
3. Bhaya, D. et al. (2011) "CRISPR-Cas Systems in Bacteria and Archaea: Versatile Small RNAs for Adaptive Defense and Regulation," Annu. Rev. Genet. 45(1), 273-297.
4. Mali, P. et al. (2013) "RNA-guided human genome engineering via Cas9," Science 339(6121), 823-826.
5. Cho, S. W. et al. (2013) "Targeted genome engineering in human cells with the Cas9 RNA-guided endonuclease," Nat. Biotechnol. 31(3), 230-232.
6. Cong, L. et al. (2013) "Multiplex genome engineering using CRISPR/Cas systems," Science 339(6121), 819-823.
7. Jinek, M. et al. (2013) "RNA-programmed genome editing in human cells," eLife 2, e00471.
8. Qi, L. S. et al. (2013) "Repurposing CRISPR as an RNA-guided platform for sequence-specific control of gene expression," Cell 152(5), 1173-1183.
9. Bikard, D. et al. (2013) "Programmable repression and activation of bacterial gene expression using an engineered CRISPR-Cas system," Nucleic Acids Res. 41(15), 7429-7437.
10. Gilbert, L. A. et al. (2013) "CRISPR-mediated modular RNA-guided regulation of transcription in eukaryotes," Cell 154(2), 442-451.
11. Mali, P. et al. (2013) "CAS9 transcriptional activators for target specificity screening and paired nickases for cooperative genome engineering," Nat. Biotechnol. 31(9), 833-838.
12. Konermann, S. et al. (2013) "Optical control of mammalian endogenous transcription and epigenetic states," Nature 500(7463), 472-476.

13. Maeder, M. L. et al. (2013) "CRISPR RNA-guided activation of endogenous human genes," Nat. Meth. 10(10), 977-979.
14. Perez-Pinera, P. et al. (2013) "RNA-guided gene activation by CRISPR-Cas9-based transcription factors," Nat. Meth. 10(10), 973-976.
15. Takahashi, K. and Yamanaka, S. (2006) "Induction of pluripotent stem cells from mouse embryonic and adult fibroblast cultures by defined factors," Cell 126(4), 663-676.
16. Moad, M. et al. (2013) "A novel model of urinary tract differentiation, tissue regeneration, and disease: reprogramming human prostate and bladder cells into induced pluripotent stem cells," Eur. Urol. 64(5), 753-761.
17. Thomson, J. A. et al. (1998) "Embryonic Stem Cell Lines Derived from Human Blastocysts," Science 282(5391), 1145-1147.
18. Cattoglio, C. et al. (2007) "Hot spots of retroviral integration in human CD34+ hematopoietic cells," Blood 110(6), 1770-1778.
19. Montini, E. et al. (2006) "Hematopoietic stem cell gene transfer in a tumor-prone mouse model uncovers low genotoxicity of lentiviral vector integration," Nat. Biotechnol. 24(6), 687-696.
20. Ciuffi, A. et al. (2006) "Integration Site Selection by HIV-Based Vectors in Dividing and Growth-Arrested IMR-90 Lung Fibroblasts," Mol. Ther. 13(2), 366-373.
21. Marraffini, L. A. and Sontheimer, E. J. (2010) "CRISPR interference: RNA-directed adaptive immunity in bacteria and archaea," Nat. Rev. Genet. 11(3), 181-190.
22. Pennisi, E. (2013) "The CRISPR craze," Science 341 (6148), 833-836.
23. Jinek, M. et al. (2012) "A Programmable Dual-RNA-Guided DNA Endonuclease in Adaptive Bacterial Immunity," Science 337(6096), 816-821.
24. Esvelt, K. M. et al. (2013) "Orthogonal Cas9 proteins for RNA-guided gene regulation and editing," Nat. Meth. 10(11), 1116-1121.
25. Buganim, Y. et al. (2013) "Mechanisms and models of somatic cell reprogramming," Nat. Rev. Genet. 14(6), 427-439.
26. Addis, R. C. and Epstein, J. A. (2013) "Induced regeneration—the progress and promise of direct reprogramming for heart repair," Nat. Med. 19(7), 829-836.
27. Trounson, A. et al. (2012) "Human disease modeling with induced pluripotent stem cells," Curr. Opin. Genet. Dev. 22(5), 509-516.
28. Zhou, Q. et al. (2008) "In vivo reprogramming of adult pancreatic exocrine cells to b-cells," Nature 455(7213), 627-632.
29. Chambers, I. et al. (2003) "Functional expression cloning of Nanog, a pluripotency sustaining factor in embryonic stem cells," Cell 113(5), 643-655.
30. Vierbuchen, T. et al. (2010) "Direct conversion of fibroblasts to functional neurons by defined factors," Nature 463(7284), 1035-1041.
31. Sims, D. et al. (2011) "High-throughput RNA interference screening using pooled shRNA libraries and next generation sequencing," Genome Biol. 12(10), R104.
32. Moffat, J. et al. (2006) "A Lentiviral RNAi Library for Human and Mouse Genes Applied to an Arrayed Viral High-Content Screen," Cell 124(6), 1283-1298.
33. Root, D. E. et al. (2006) "Genome-scale loss-of-function screening with a lentiviral RNAi library," Nat. Meth. 3(9), 715-719.
34. Hu, G. et al. (2009) "A genome-wide RNAi screen identifies a new transcriptional module required for self-renewal," Genes Dev 23(7), 837-848.
35. Ivanova, N. et al. (2006) "Dissecting self-renewal in stem cells with RNA interference," Nature 442(7102), 533-538.
36. Gao, X. et al. (2013) "Reprogramming to Pluripotency Using Designer TALE Transcription Factors Targeting Enhancers," Stem Cell Reports 1(2), 183-197.
37. Ran, F. A. et al. (2013) "Double Nicking by RNA-Guided CRISPR Cas9 for Enhanced Genome Editing Specificity," Cell 154(6), 1380-1389.
38. Hwang, W. Y. et al. (2013) "Efficient genome editing in zebrafish using a CRISPR-Cas system," Nat. Biotechnol. 31(3), 227-229.
39. Jao, L.-E. et al. (2013) "Efficient multiplex biallelic zebrafish genome editing using a CRISPR nuclease system," P.N.A.S. 110(34), 13904-13909.
40. Yang, H. et al. (2013) "One-step generation of mice carrying reporter and conditional alleles by CRISPR/Cas-mediated genome engineering," Cell 154(6), 1370-1379.
41. Sorek, R. et al. (2013) "CRISPR-Mediated Adaptive Immune Systems in Bacteria and Archaea," Annu. Rev. Biochem. 82(1), 237-266.
42. Hsu, P. D. et al. (2013) "DNA targeting specificity of RNA-guided Cas9 nucleases," Nat. Biotechnol. 31(9), 827-832.
43. Hou, Z. et al. (2013) "Efficient genome engineering in human pluripotent stem cells using Cas9 from *Neisseria meningitidis*," P.N.A.S. 110(39), 15644-15649.
44. Zhang, Y. et al. (2013) "Processing-Independent CRISPR RNAs Limit Natural Transformation in *Neisseria meningitidis*," Mol. Cell 50(4), 488-503.
45. Cheng, A. W. et al. (2013) "Multiplexed activation of endogenous genes by CRISPR-on, an RNA-guided transcriptional activator system," Cell Res. 23(10), 1163-1171.
46. Larson, M. H. et al. (2013) "CRISPR interference (CRISPRi) for sequence-specific control of gene expression," Nat. Protoc. 8(11), 2180-2196.
47. Kanai-Azuma, M. et al. (2002) "Depletion of definitive gut endoderm in Sox17-null mutant mice," Development 129(10), 2367-2379.
48. Rada-Iglesias, A. et al. (2011) "A unique chromatin signature uncovers early developmental enhancers in humans," Nature 470(7333), 279-283.
49. Ladewig, J. et al. (2013) "Leveling Waddington: the emergence of direct programming and the loss of cell fate hierarchies," Nat. Rev. Mol. Cell Biol. 14(4), 225-236.
50. Cobaleda, C. et al. (2007) "Conversion of mature B cells into T cells by dedifferentiation to uncommitted progenitors," Nature 449(7161), 473-477.
51. Hay, D. C. et al. (2004) "Oct-4 Knockdown Induces Similar Patterns of Endoderm and Trophoblast Differentiation Markers in Human and Mouse Embryonic Stem Cells," Stem Cells 22(2), 225-235.
52. Lee, J. et al. (2006) "The Human OCT-4 Isoforms Differ in Their Ability to Confer Self-renewal," J. Biol. Chem. 281(44), 33554-33565.
53. Kagey, M. H. et al. (2010) "Mediator and cohesin connect gene expression and chromatin architecture," Nature 467(7314), 430-435.
54. Langmead, B. and Salzberg, S. L. (2012) "Fast gapped-read alignment with Bowtie 2," Nat. Meth. 9(4), 357-359.

55. Cong, L. et al. (2012) "Comprehensive interrogation of natural TALE DNA-binding modules and transcriptional repressor domains," Nature Communications 3, 968.
56. Zhang, F. et al. (2011) "Efficient construction of sequence-specific TAL effectors for modulating mammalian transcription," Nat. Biotechnol. 29(2), 149-153.
57. Maehr, R. et al. (2009) "Generation of pluripotent stem cells from patients with type 1 diabetes," P.N.A.S. 106 (37), 15768-15773.
58. Huangfu, D. et al. (2008) "Induction of pluripotent stem cells by defined factors is greatly improved by small-molecule compounds," Nat. Biotechnol. 26(7), 795-797.
59. Bultmann, S. et al. (2012) "Targeted transcriptional activation of silent oct4 pluripotency gene by combining designer TALEs and inhibition of epigenetic modifiers," Nucleic
Acids Res. 40(12), 5368-5377.
60. D'Amour, K. A. et al. (2005) "Efficient differentiation of human embryonic stem cells to definitive endoderm," Nat. Biotechnol. 23(12), 1534-1541.
61. Kubo, A. et al. (2004) "Development of definitive endoderm from embryonic stem cells in culture," Development 131(7), 1651-1662.
62. D'Amour, K. A. et al. (2006) "Production of pancreatic hormone-expressing endocrine cells from human embryonic stem cells," Nat. Biotechnol. 24(11), 1392-1401.
63. Sherwood, R. I. et al. (2011) "Wnt signaling specifies and patterns intestinal endoderm,"
Mech. Dev. 128(7-10), 387-400.
64. Kearns, N. A. et al. (2013) "Generation of organized anterior foregut epithelia from pluripotent stem cells using small molecules," Stem Cell Res. 11(3), 1003-1012.
65. Gifford, Casey A. et al. (2013) "Transcriptional and epigenetic dynamics during specification of human embryonic stem cells," Cell 153(5), 1149-1163.
66. Seguin, C. A. et al. (2008) "Establishment of Endoderm Progenitors by SOX Transcription Factor Expression in Human Embryonic Stem Cells," Cell Stem Cell 3(2), 182-195.
67. Gouon-Evans, V. et al. (2006) "BMP-4 is required for hepatic specification of mouse embryonic stem cell-derived definitive endoderm," Nat. Biotechnol. 24(11), 1402-1411.
68. Green, M. D. et al. (2011) "Generation of anterior foregut endoderm from human embryonic and induced pluripotent stem cells," Nat. Biotechnol. 29(3), 267-272.
69. Cabili, M. N. et al. (2011) "Integrative annotation of human large intergenic noncoding RNAs reveals global properties and specific subclasses," Genes Dev 25(18), 1915-1927.
70. Ravasi, T. et al. (2010) "An Atlas of Combinatorial Transcriptional Regulation in Mouse and Man," Cell 140(5), 744-752.
71. Cheng, X. et al. (2012) "Self-Renewing Endodermal Progenitor Lines Generated from Human Pluripotent Stem Cells," Cell Stem Cell 10(4), 371-384.
72. Sun, X. et al. (2013) "Directed Differentiation of Human Embryonic Stem Cells into Thymic Epithelial Progenitor-like Cells Reconstitutes the Thymic Microenvironment In Vivo," Cell Stem Cell 13(2), 230-236.
73. Mou, H. et al. (2012) "Generation of multipotent lung and airway progenitors from mouse ESCs and patient-specific cystic fibrosis iPSCs," Cell Stem Cell 10(4), 385-397.
74. Wong, A. P. et al. (2012) "Directed differentiation of human pluripotent stem cells into mature airway epithelia expressing functional CFTR protein," Nat. Biotechnol. 30(9), 876-882.
75. Parent, Audrey V. et al. (2013) "Generation of functional thymic epithelium from human embryonic stem cells that supports host T cell development," Cell Stem Cell 13(2), 219-229.
76. Kroon, E. et al. (2008) "Pancreatic endoderm derived from human embryonic stem cells generates glucose-responsive insulin-secreting cells in vivo," Nat. Biotechnol. 26(4), 443-452.
77. Rezania, A. et al. (2011) "Production of functional glucagon-secreting α-cells from human embryonic stem cells," Diabetes 60(1), 239-247.

We claim:

1. A method, comprising:
   a) providing;
      i) a live cell comprising a first genomic locus and a second genomic locus and a catalytically active Cas9;
      ii) a first deoxyribonucleic acid (DNA) construct encoding a first catalytically inactive Cas9 (dCas) protein and a first fluorescent label protein having a first color, wherein said first dCas protein binds to a first single guide ribonucleic acid (sgRNA) that comprises a first complementary sequence to said first genomic locus;
      iii) a second DNA construct encoding a second dCas and a second fluorescent label protein having a second color, wherein said second dCas protien binds to a second sgRNA that comprises a second complementary sequence to said second genomic locus;
   b) transfecting said live cell with said first DNA construct, said second DNA construct, said first sgRNA and said second sgRNA, wherein said first dCas construct and said second dCas construct are expressed;
   c) determining that said catalytically active Cas9 has edited: i) only said first genomic locus when only said first color is detected; ii) both said first genomic locus and said second genomic locus when both said first color and said second color is detected; or iii) only said second genomic locus with only said second color is detected.

2. The method of claim 1, wherein said detecting is performed by fluorescence microscopy.

3. The method of claim 1, wherein said detecting is performed by fluorescence activated cell sorting.

4. The method of claim 1, wherein said detecting is performed without a method selected from the group consisting of nucleic acid sequencing, reverse transcriptase polymerase chain reaction and gel electrophoresis.

5. The method of claim 1, wherein said first color and said second color are a different color selected from the group consisting of red, green and blue.

6. The method of claim 1, wherein said first DNA construct further comprises a first DNA binding protein.

7. The method of claim 1, wherein said second DNA construct further comprises a second DNA binding protein.

8. The method of claim 1, wherein said first dCas9 protein and said second dCas9 protein are orthogonal.

9. The method of claim 1 wherein said first dCas9 protein and said second dCas9 protein are from a bacterial species selected from the group consisting of *S. pyogenes, N. meningitidis* and *S. thermophiles*.

* * * * *